United States Patent
Lawson et al.

(10) Patent No.: US 11,174,311 B2
(45) Date of Patent: *Nov. 16, 2021

(54) ANTIBODY AGAINST TRIMERIC TNFα COMPLEX

(71) Applicants: UCB BIOPHARMA SRL, Brussels (BE); SANOFI, Paris (FR)

(72) Inventors: Alastair David Griffiths Lawson, Slough (GB); Daniel John Lightwood, Slough (GB); Rebecca Jayne Munro, Slough (GB); James Philip O'Connell, Slough (GB); John Robert Porter, Slough (GB)

(73) Assignees: UCB BIOPHARMA SRL, Brussels (BE); SANOFI, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/470,999

(22) PCT Filed: Dec. 13, 2017

(86) PCT No.: PCT/EP2017/082685
§ 371 (c)(1),
(2) Date: Jun. 19, 2019

(87) PCT Pub. No.: WO2018/114538
PCT Pub. Date: Jun. 28, 2018

(65) Prior Publication Data
US 2019/0330327 A1 Oct. 31, 2019

(30) Foreign Application Priority Data

Dec. 21, 2016 (GB) ...................... 1621907

(51) Int. Cl.
*C07K 16/24* (2006.01)
(52) U.S. Cl.
CPC ........ *C07K 16/241* (2013.01); *C07K 2317/32* (2013.01); *C07K 2317/34* (2013.01); *C07K 2317/55* (2013.01); *C07K 2317/92* (2013.01)
(58) Field of Classification Search
None
See application file for complete search history.

(56) References Cited

U.S. PATENT DOCUMENTS

| | | | |
|---|---|---|---|
| 4,908,372 A | 3/1990 | Carr et al. | |
| 5,597,899 A | 1/1997 | Banner et al. | |
| 7,691,815 B2 | 4/2010 | Liang et al. | |
| 7,993,636 B2 | 8/2011 | Mayumi et al. | |
| 8,377,441 B2 | 2/2013 | Chang | |
| 9,908,944 B2 | 3/2018 | Padkjaer et al. | |
| 10,428,148 B2 | 10/2019 | Katagiri et al. | |
| 10,705,094 B2 | 7/2020 | O'Connell et al. | |
| 10,775,385 B2 | 9/2020 | O'Connell et al. | |
| 10,883,996 B2 | 1/2021 | O'Connell et al. | |
| 10,969,393 B2 | 4/2021 | O'Connell et al. | |
| 11,022,614 B2 | 6/2021 | O'Connell et al. | |
| 2001/0018507 A1 | 8/2001 | Rathjen et al. | |
| 2002/0110868 A1 | 8/2002 | Dahiyat et al. | |
| 2003/0060461 A1 | 3/2003 | Kodama et al. | |
| 2004/0067982 A1 | 4/2004 | Zheng et al. | |
| 2006/0222624 A1 | 10/2006 | Bratt et al. | |
| 2007/0117755 A1 | 5/2007 | Liang | |
| 2009/0022659 A1 | 1/2009 | Olson et al. | |
| 2009/0269357 A1 | 10/2009 | Ke et al. | |
| 2010/0266613 A1 | 10/2010 | Harding et al. | |
| 2010/0297111 A1 | 11/2010 | Beirnaert | |
| 2011/0250130 A1 | 10/2011 | Benatuil et al. | |
| 2013/0018105 A1 | 1/2013 | Carrol et al. | |
| 2014/0112929 A1 | 4/2014 | Batuwangala et al. | |
| 2014/0165223 A1 | 6/2014 | Ntouni et al. | |
| 2020/0400678 A1 | 12/2020 | O'Connell et al. | |
| 2021/0088530 A1 | 3/2021 | O'Connell et al. | |
| 2021/0132079 A1 | 5/2021 | O'Connell et al. | |
| 2021/0140972 A1 | 5/2021 | O'Connell et al. | |

FOREIGN PATENT DOCUMENTS

| | | |
|---|---|---|
| CA | 2005053 A1 | 6/1990 |
| CN | 1204320 A | 1/1999 |
| CN | 1099802 C | 1/2003 |
| CN | 1700930 A | 11/2005 |
| CN | 104428293 A | 5/2015 |
| CN | 104619709 A | 5/2015 |
| EP | 0288088 B1 | 9/1990 |
| EP | 0492448 A1 | 3/2000 |
| JP | H0596 A | 1/1993 |
| JP | 2003-040888 A | 2/2003 |
| JP | 2008-539772 A | 11/2008 |
| JP | 2010-172307 A | 8/2010 |
| JP | 2011/519836 A | 7/2011 |
| JP | 2012-509312 A | 4/2012 |
| WO | 93/06489 A1 | 4/1993 |
| WO | 93/14083 A1 | 7/1993 |
| WO | 94/18325 A1 | 8/1994 |
| WO | 97/22587 A1 | 6/1997 |
| WO | 02/098869 A2 | 12/2002 |
| WO | 2004/012673 A2 | 2/2004 |
| WO | 2006/122786 A2 | 11/2006 |

(Continued)

OTHER PUBLICATIONS

Shi Hu et al., J Biol. Chem. 288, 27059-27067, 2013. (Year: 2013).*

(Continued)

*Primary Examiner* — Elly-Gerald Stoica
(74) *Attorney, Agent, or Firm* — Medler Ferro Woodhouse & Mills PLLC

(57) ABSTRACT

It has been demonstrated that certain compounds bind to TNF and stabilise a conformation of trimeric TNF that binds to the TNF receptor. Antibodies which selectively bind to complexes of such compounds with TNF superfamily members are disclosed. These antibodies may be used to detect further compounds with the same activity, and as target engagement biomarker.

Figure 1:
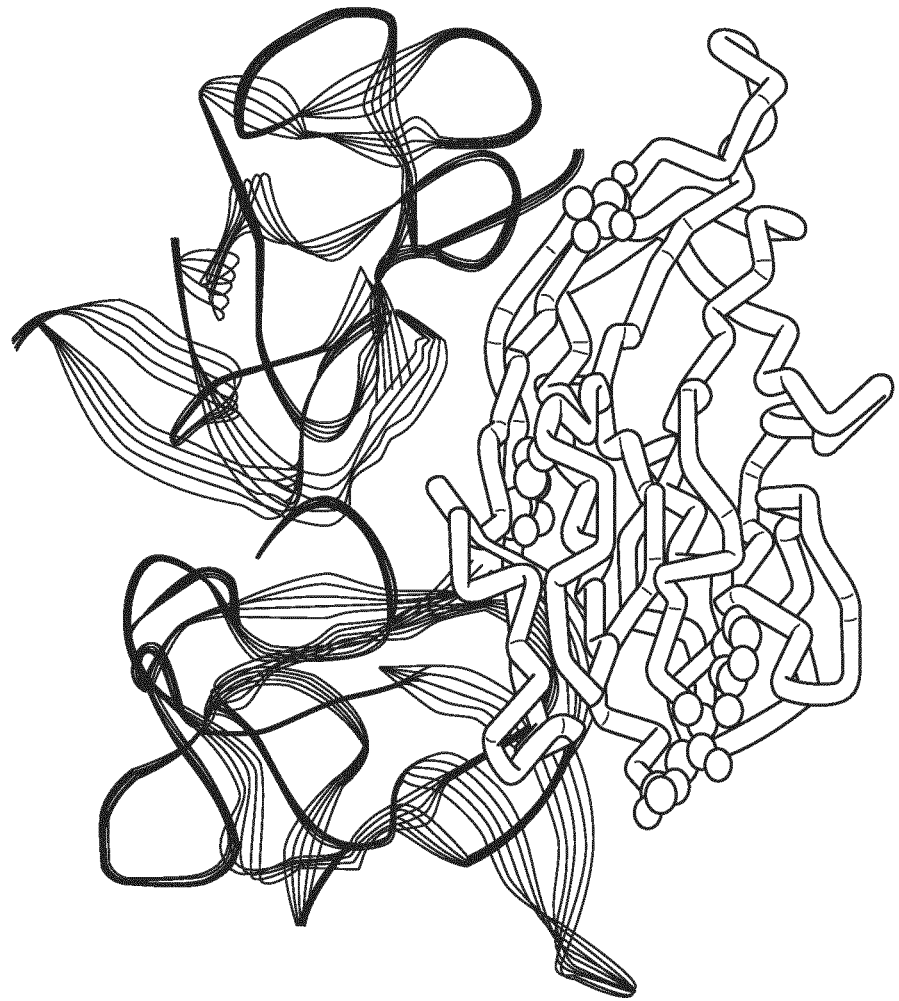

14 Claims, 16 Drawing Sheets
Specification includes a Sequence Listing.

(56) References Cited

FOREIGN PATENT DOCUMENTS

| WO | 2007/060411 A1 | | 5/2007 | |
| WO | 2008/144753 A2 | | 11/2008 | |
| WO | 2008/144757 A1 | | 11/2008 | |
| WO | 2009/020848 A2 | | 2/2009 | |
| WO | 2009/132037 A1 | | 10/2009 | |
| WO | 2009/155723 A2 | | 12/2009 | |
| WO | 2010/058419 A1 | | 5/2010 | |
| WO | 2010/118404 A2 | | 10/2010 | |
| WO | WO 2012/078878 | * | 6/2012 | ............. C12P 21/06 |
| WO | 2013/024040 A2 | | 2/2013 | |
| WO | 2013/186229 A1 | | 12/2013 | |
| WO | 2014/001557 A1 | | 1/2014 | |
| WO | 2014/009295 A1 | | 1/2014 | |
| WO | 2014/009296 A1 | | 1/2014 | |
| WO | 2014/040076 A1 | | 3/2014 | |
| WO | 2014/123696 A1 | | 8/2014 | |
| WO | 2014/165223 A1 | | 10/2014 | |
| WO | 2015/086496 A1 | | 6/2015 | |
| WO | 2015/086498 A1 | | 6/2015 | |
| WO | 2015/086499 A1 | | 6/2015 | |
| WO | 2015/086500 A1 | | 6/2015 | |
| WO | 2015/086501 A1 | | 6/2015 | |
| WO | 2015/086502 A1 | | 6/2015 | |
| WO | 2015/086503 A1 | | 6/2015 | |
| WO | 2015/086504 A1 | | 6/2015 | |
| WO | 2015/086505 A1 | | 6/2015 | |
| WO | 2015/086506 A1 | | 6/2015 | |
| WO | 2015/086507 A1 | | 6/2015 | |
| WO | 2015/086508 A1 | | 6/2015 | |
| WO | 2015/086509 A1 | | 6/2015 | |
| WO | 2015/086511 A1 | | 6/2015 | |
| WO | 2015/086512 A1 | | 6/2015 | |
| WO | 2015/086513 A1 | | 6/2015 | |
| WO | 2015/086519 A1 | | 6/2015 | |
| WO | 2015/086520 A1 | | 6/2015 | |
| WO | 2015/086521 A1 | | 6/2015 | |
| WO | 2015/086523 A1 | | 6/2015 | |
| WO | 2015/086525 A1 | | 6/2015 | |
| WO | 2015/086526 A1 | | 6/2015 | |
| WO | 2015/086527 A1 | | 6/2015 | |
| WO | 2016/050975 A1 | | 4/2016 | |
| WO | 2016/149436 A1 | | 9/2016 | |
| WO | 2016/149437 A1 | | 9/2016 | |
| WO | 2016/149439 A1 | | 9/2016 | |
| WO | 2016/168633 A1 | | 10/2016 | |
| WO | 2016/168638 A1 | | 10/2016 | |
| WO | 2016/168641 A1 | | 10/2016 | |
| WO | 2016/198398 A1 | | 12/2016 | |
| WO | 2016/198400 A1 | | 12/2016 | |
| WO | 2016/198401 A1 | | 12/2016 | |
| WO | 2016/202411 A1 | | 12/2016 | |
| WO | 2016/202412 A1 | | 12/2016 | |
| WO | 2016/202413 A1 | | 12/2016 | |
| WO | 2016/202414 A1 | | 12/2016 | |
| WO | 2016/202415 A1 | | 12/2016 | |
| WO | 2017/023902 A1 | | 2/2017 | |
| WO | 2017/023905 A1 | | 2/2017 | |
| WO | 2017/167993 A1 | | 10/2017 | |
| WO | 2017/167994 A1 | | 10/2017 | |
| WO | 2017/167995 A1 | | 10/2017 | |
| WO | 2017/167996 A1 | | 10/2017 | |

OTHER PUBLICATIONS

Notice of Allowance in U.S. Appl. No. 15/736,336 dated Jun. 4, 2020.
Non-final Office Action in U.S. Appl. No. 15/736,535 dated May 4, 2020.
Alzani et al., "Mechanism of Suramin-Induced Deoligomerization of Tumor Necrosis Factor α," (1995) Biochemistry, 34, 6344-6350.
Anderson et al., "Prediction of residues in discontinuous B-cell epitopes using protein 3D structures," (2006) Protein Science, 15, 2258-2567.
Baldwin et al., "Structural changes of tumor necrosis factor a associated with membrane insertion and channel formation," (1996) PNAS, 93, 1021-1026.
Cha et al., "High Resolution Crystal Structure of a Human Tumor Necrosis Factor-α Mutant with Low Systemic Toxicity," (1998) The Journal of Biological Chemistry, 273, 2153-2160.
Eck et al., "The Structure of Tumor Necrosis Factor-α at 2.6 Å Resolution," (1989) Journal of Biological Chemistry, 264, 17595-17605.
Fang et al., "TNF: a structure and function relationship," Foreign Medical Immunology, vol. 26, No. 2. (2003). [Machine translation].
Ganesan et al., "Exploratory computational assessment of possible binding modes for small molecule inhibitors of the CD40-CD154 co-stimulatory interaction," (2012) Pharmazie, 67, 374-379.
Garcia et al., "Roles of Soluble and Membrane TNF and Related Ligands in Mycobacterial Infections: Effects of Selective and Non-selective TNF Inhibitors During Infection," Advances in TNF Family Research pp. 187-201.
Grell et al., "The Transmembrane Form of Tumor Necrosis Factor is the Prime Acting Ligand of the 80 kDa Tumor Necrosis Factor Receptor," (1995) Cell, 83, 793-802.
He et al., "Small-Molecule Inhibition of TNF-α," (2005) Science, 310, 1022-1025.
Hoffmann et al., "New Binding Mode to TNF-Alpha Revealed by Ubiquitin-Based Artificial Binding Protein," (2012) PLOS ONE, 7, 1-10.
Hu et al., "Comparison of the Inhibition Mechanisms of Adalimumab and Infliximab in Treating Tumor Necrosis Factor α-Associated Diseases from a Molecular View," (2013) Journal of Biological Chemistry, 288, 27059-27067.
Jones et al., "The structure of tumour necrosis factor—implications for biological function," (1990) Journal of Cell Science: Supplement 13, 11-18.
Kim et al., "Comparative Analyses of Complex Formation and Binding Sites between Human Tumor Necrosis Factor-alpha and its Three Antagonists Elucidate their Different Neutralizing Mechanisms," (2007) Journal of Molecular Biology, 374, 1374-1388.
Liang et al., "Structural Basis for Treating Tumor Necrosis Factor α (TNFα)-associated Diseases with the Therapeutic Antibody Infliximab," (2013) Journal of Biological Chemistry, 288, 13799-13807.
Lloyd et al., "Modelling the human immune response: performance of a 1011 human antibody repertoire against a broad panel of therapeutically relevant antigens," (2009) Protein Engineering, Design & Selection, 22, 159-168.
Loetscher et al., "Recombinant 55-kDa Tumor Necrosis Factor (TNF) Receptor," (1991) Journal of Biological Chemistry, 266, 18324-18329.
Ma et al., "A Novel Small-molecule Tumor Necrosis Factor α Inhibitor Attenuates Inflammation in a Hepatitis Mouse Model," (2014) Journal of Biological Chemistry, 289, 12457-12466.
Mascarenhas et al., "Are different stoichiometries feasible for complexes between Tymphotoxin-alpha tumor necrosis factor receptor 1," (2012) BMC Structural Biology, 12, Art 8.
Mukai et al., "Solution of the Structure of the TNF-TNFR2 Complex," Biochemistry 3(148): 1-11 (2010).
Nesbitt et al., "Mechanism of Action of Certolizumab Pegol (CDP870): In Vitro Comparison with Other Anti-tumor Necrosis Factor α Agents," (2007) Inflamm Bowel Dis, 13, 1323-1332.
Sedger et al., "TNF and TNF-receptors: From Mediators of Cell Death and Inflammation to Therapeutic Giants—Past, Present, and Future," Cytokine & Growth Factor Reviews, 25:453-473 (2014).
Shibata et al., "Creation and X-ray Structure Analysis of the Tumor Necrosis Factor Receptor-1-selective Mutant of a Tumor Necrosis Factor-α Antagonist," J. Biol. Chem 283(2): 998-1007 (2008).
Silvian et al., "Small Molecule Inhibition of the TNF Family Cytokine CD40 Ligand through a Subunit Fracture Mechanism," (2011) ACS Chemical Biology, 6, 636-647.
Simon et al., "Determining target engagement in living systems," (2013) Nature Chemical Biology, 9, 200-205.
Sudhamsu et al., "Dimerization of LTβR by LTα$_1$β$_2$ is necessary and sufficient for signal transduction," (2013) PNAS, 110, 19896-19901.

(56) References Cited

OTHER PUBLICATIONS

Tracey et al., "Tumor necrosis factor antagonist mechanisms of action: A comprehensive review," (2007) Pharmacology and Therapeutics, 117, 244-279.
Zalevsky et al., "Dominant-Negative Inhibitors of Soluble TNF Attenuate Experimental Arthritis without Suppressing Innate Immunity to Infection," (2007) Journal of Immunology, 179, 1872-188.
Zhu et al., "Characterization of the neutralizing activity of three anti-human TNF monoclonal antibodies and prediction of their TNF epitopes by molecular modeling and mutant protein approach," (2006) Immunology Letters, 102, 177-183.
Office Action issued in U.S. Appl. No. 15/736,520, dated Feb. 28, 2019.
Office Action issued in U.S. Appl. No. 15/736,336, dated Apr. 24, 2019.
Office Action issued in U.S. Appl. No. 15/736,535, dated Apr. 25, 2019.
Office Action issued in U.S. Appl. No. 15/736,558, dated Apr. 26, 2019.
Office Action in U.S. Appl. No. 15/736,614 dated Aug. 29, 2019.
Office Action in U.S. Appl. No. 15/736,336 dated Oct. 3, 2019.
Office Action in U.S. Appl. No. 15/736,520 dated Oct. 7, 2019.
Office Action in U.S. Appl. No. 15/736,535 dated Nov. 8, 2019.
Office Action in U.S. Appl. No. 15/736,558 dated Nov. 8, 2019.
Office Action in EP 15784370.7 dated Jan. 30, 2020.
Notice of Allowance in U.S. Appl. No. 15/736,520 dated Feb. 26, 2020.
Notice of Allowance in U.S. Appl. No. 15/736,614 dated Apr. 6, 2020.
Office Action in U.S. Appl. No. 15/736,558 dated Apr. 21, 2020.
Chinese National Intellectual Property Search Report in 201580081000.1 dated Aug. 20, 2019.
Supplemental Notice of Allowance dated Sep. 25, 2020 in U.S. Appl. No. 15/736,535.
Final Office Action dated Oct. 8, 2020 in U.S. Appl. No. 15/736,558.
Notice of Allowance dated Jan. 25, 2021, issued in U.S. Appl. No. 15/736,558.

\* cited by examiner

Fig. 8

| File: | 13090601T |
|---|---|
| Item: | 1974 cyno TNF control 1 |
| Ligand: | CA185_1974 |
| Curve: | Fe=2-1 |
| Sample: | cyno |
| Temperature | 25 °C |

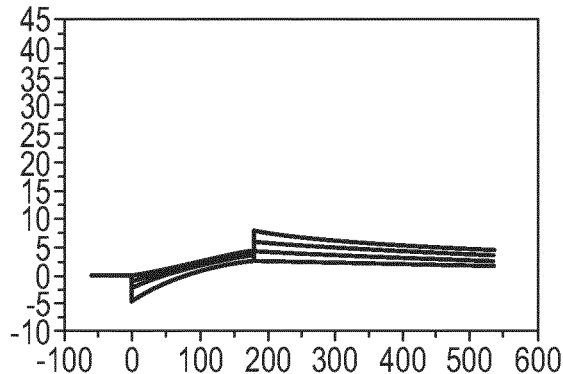

| Fit: | 1:1: Binding |
|---|---|
| Ka(1/Ms): | 1.025E+5 |
| Kd (1/s): | 0.001872 |

| File: | 13090601T |
|---|---|
| Item: | 1974 cyno TNF control 2 |
| Ligand: | CA185_1974 |
| Curve: | Fe=2-1 |
| Sample: | cyno |
| Temperature | 25 °C |

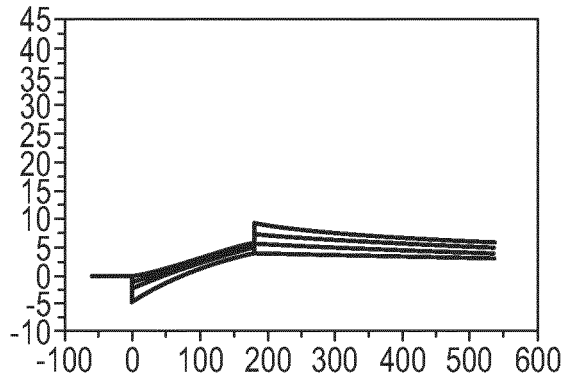

| Fit: | 1:1: Binding |
|---|---|
| Ka(1/Ms): | 1.253E+5 |
| Kd (1/s): | 0.001923 |

| File: | 13090601T |
|---|---|
| Item: | 1974 cyno TNF+2080 1 |
| Ligand: | CA185_1974 |
| Curve: | Fe=2-1 |
| Sample: | cyno+NCE |
| Temperature | 25 °C |

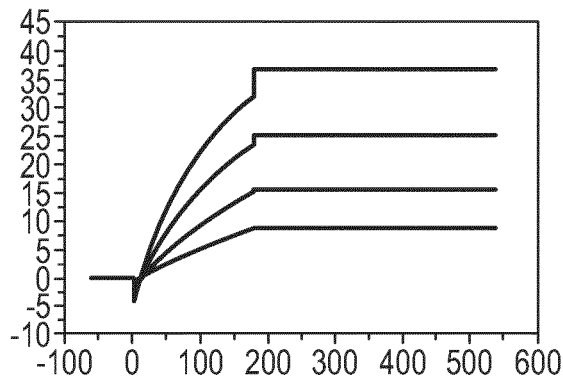

| Fit: | 1:1: Binding |
|---|---|
| Ka(1/Ms): | 1.842E+5 |
| Kd (1/s): | 1.457E-5 |

| File: | 13090601T |
|---|---|
| Item: | 1974 cyno TNF+2080 2 |
| Ligand: | CA185_1974 |
| Curve: | Fe=2-1 |
| Sample: | cyno+NCE |
| Temperature | 25 °C |

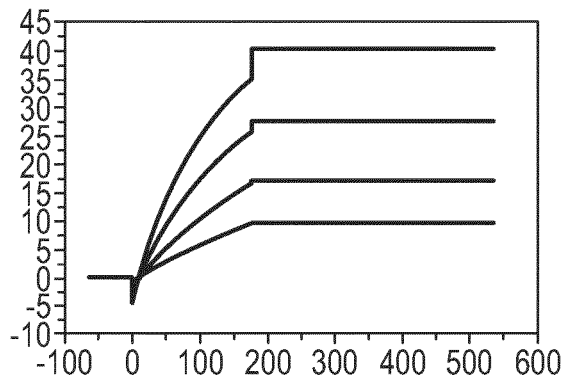

| Fit: | 1:1: Binding |
|---|---|
| Ka(1/Ms): | 2.008E+5 |
| Kd (1/s): | 2.053E-5 |

Fig. 9

| File: | 13090601T | File: | 13090601T |
|---|---|---|---|
| Item: | 1974 human TNF control 1 | Item: | 1974 human TNF control 2 |
| Ligand: | CA185_1974 | Ligand: | CA185_1974 |
| Curve: | Fe=4-3 | Curve: | Fe=4-3 |
| Sample: | human | Sample: | human |
| Temperature | 25 °C | Temperature | 25 °C |

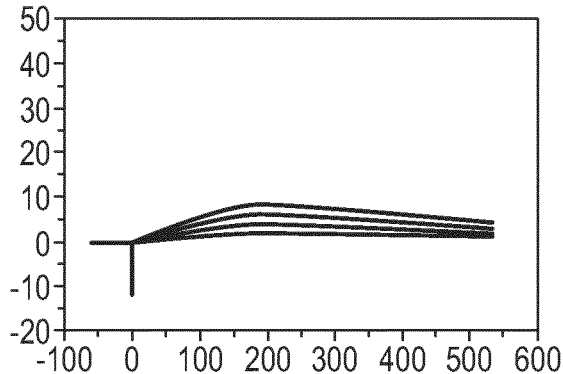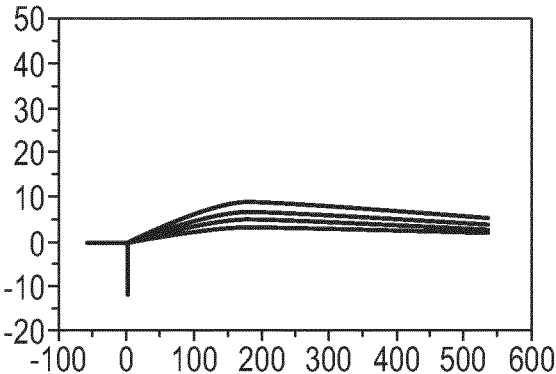

| Fit: | 1:1: Binding | Fit: | 1:1: Binding |
|---|---|---|---|
| Ka(1/Ms): | 8.023E+4 | Ka(1/Ms): | 1.051E+5 |
| Kd (1/s): | 0.001773 | Kd (1/s): | 0.001671 |

| File: | 13090601T | File: | 13090601T |
|---|---|---|---|
| Item: | 1974 human TNF+2080 1 | Item: | 1974 human TNF+2080 2 |
| Ligand: | CA185_1974 | Ligand: | CA185_1974 |
| Curve: | Fe=4-3 | Curve: | Fe=4-3 |
| Sample: | human+NCE | Sample: | human+NCE |
| Temperature | 25 °C | Temperature | 25 °C |

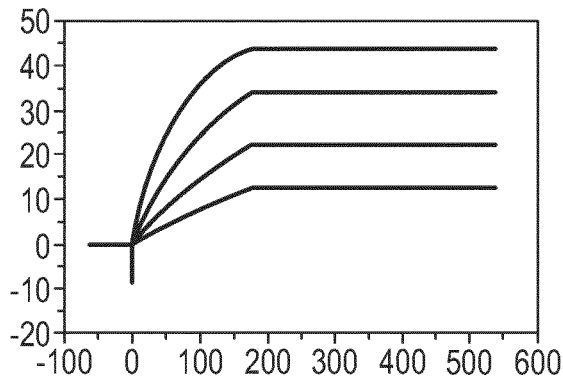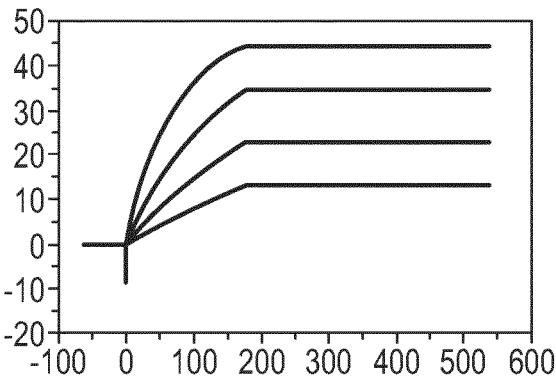

| Fit: | 1:1: Binding | Fit: | 1:1: Binding |
|---|---|---|---|
| Ka(1/Ms): | 3.053E+5 | Ka(1/Ms): | 3.069E+5 |
| Kd (1/s): | 1.477E-7 | Kd (1/s): | 2.726E-5 |

Fig. 10

| Compound | Structure |
|---|---|
| 1 | (chemical structure) |
| 2 | (chemical structure) |
| 3 | (chemical structure) |
| 4 | (chemical structure) |

Fig. 10 (Cont.)
| Compound | Structure |
|---|---|
| 5 | 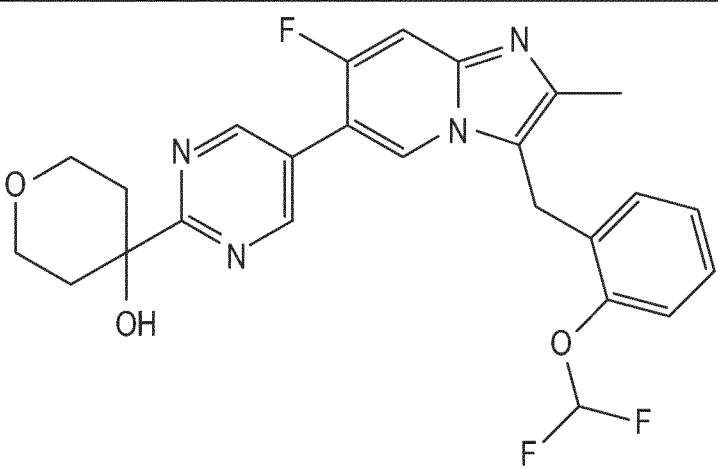 |
| 6 | 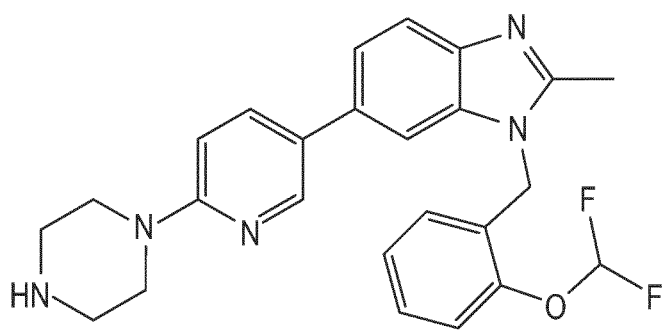 |
| 7 | 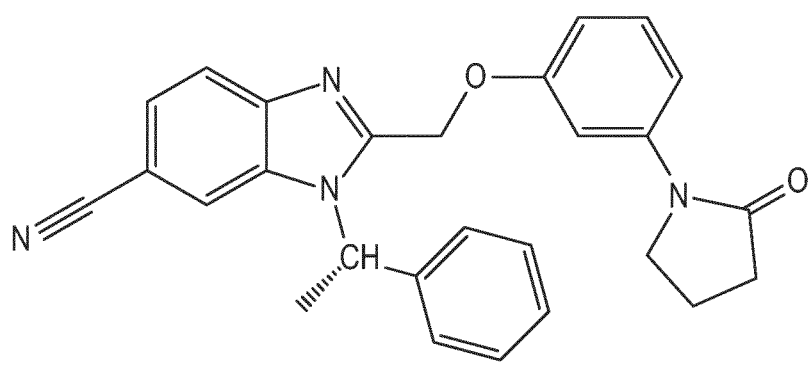 |

Fig. 15
(a)
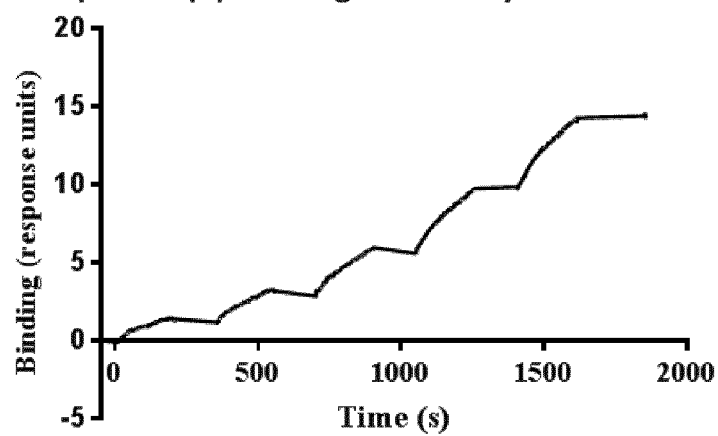
(b)
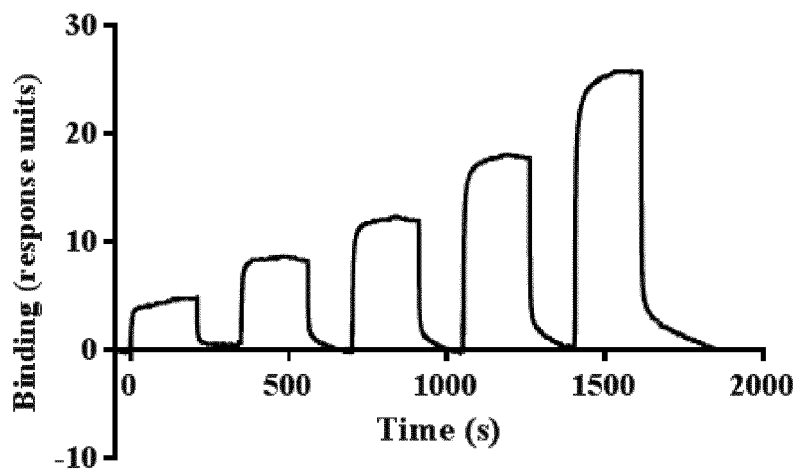

SEQUENCE LISTING

<160> NUMBER OF SEQ IDS NOS: 38

<210> SEQ ID NO 1
<211> LENGTH: 8
<212> TYPE: PRT

```
<213> ORGANISM: Artificial Sequence
<220> FEATURE:
<223> OTHER INFORMATION: LCDR1 of 1974

<400> SEQUENCE: 1

Gln Ala Ser Gln Asp Ile Gly Asn
1               5

<210> SEQ ID NO 2
<211> LENGTH: 7
<212> TYPE: PRT
<213> ORGANISM: Artificial Sequence
<220> FEATURE:
<223> OTHER INFORMATION: LCDR2 of 1974

<400> SEQUENCE: 2

Gly Ala Thr Ser Leu Ala Asp
1               5

<210> SEQ ID NO 3
<211> LENGTH: 9
<212> TYPE: PRT
<213> ORGANISM: Artificial Sequence
<220> FEATURE:
<223> OTHER INFORMATION: LCDR3 of 1974

<400> SEQUENCE: 3

Leu Gln Gly Gln Ser Thr Pro Tyr Thr
1               5

<210> SEQ ID NO 4
<211> LENGTH: 5
<212> TYPE: PRT
<213> ORGANISM: Artificial Sequence
<220> FEATURE:
<223> OTHER INFORMATION: HCDR1 of 1974

<400> SEQUENCE: 4

Ala Tyr Tyr Met Ala
1               5

<210> SEQ ID NO 5
<211> LENGTH: 18
<212> TYPE: PRT
<213> ORGANISM: Artificial Sequence
<220> FEATURE:
<223> OTHER INFORMATION: HCDR2 of 1974

<400> SEQUENCE: 5

Ala Ser Ile Asn Tyr Asp Gly Ala Asn Thr Phe Tyr Arg Asp Ser Val
1               5                   10                  15

Lys Gly

<210> SEQ ID NO 6
<211> LENGTH: 12
<212> TYPE: PRT
<213> ORGANISM: Artificial Sequence
<220> FEATURE:
<223> OTHER INFORMATION: HCDR3 of 1974

<400> SEQUENCE: 6

Glu Ala Tyr Gly Tyr Asn Ser Asn Trp Phe Gly Tyr
1               5                   10

<210> SEQ ID NO 7
<211> LENGTH: 107
```

```
<212> TYPE: PRT
<213> ORGANISM: Artificial Sequence
<220> FEATURE:
<223> OTHER INFORMATION: LCVR of 1974

<400> SEQUENCE: 7

Asp Ile Gln Met Thr Gln Ser Pro Ala Ser Leu Pro Ala Ser Pro Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Ala
    50                  55                  60

Ser Arg Ser Gly Thr Gln Tyr Ser Leu Lys Ile Ser Arg Leu Gln Val
65                  70                  75                  80

Glu Asp Phe Gly Ile Phe Tyr Cys Leu Gln Gly Gln Ser Thr Pro Tyr
                85                  90                  95

Thr Phe Gly Ala Gly Thr Lys Leu Glu Leu Lys
            100                 105

<210> SEQ ID NO 8
<211> LENGTH: 121
<212> TYPE: PRT
<213> ORGANISM: Artificial Sequence
<220> FEATURE:
<223> OTHER INFORMATION: HCVR of 1974

<400> SEQUENCE: 8

Asp Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Ala Tyr
            20                  25                  30

Tyr Met Ala Trp Val Arg Gln Ala Pro Thr Lys Gly Leu Glu Trp Val
        35                  40                  45

Ala Ser Ile Asn Tyr Asp Gly Ala Asn Thr Phe Tyr Arg Asp Ser Val
    50                  55                  60

Lys Gly Arg Phe Thr Val Ser Arg Asp Asn Ala Arg Ser Ser Leu Tyr
65                  70                  75                  80

Leu Gln Met Asp Ser Leu Arg Ser Glu Asp Thr Ala Thr Tyr Tyr Cys
                85                  90                  95

Thr Thr Glu Ala Tyr Gly Tyr Asn Ser Asn Trp Phe Gly Tyr Trp Gly
            100                 105                 110

Gln Gly Thr Leu Val Thr Val Ser Ser
        115                 120

<210> SEQ ID NO 9
<211> LENGTH: 321
<212> TYPE: DNA
<213> ORGANISM: Artificial Sequence
<220> FEATURE:
<223> OTHER INFORMATION: LCVR DNA of 1974

<400> SEQUENCE: 9
gacatccaga tgacccagtc tcctgcctcc ctgcctgcat ccccggaaga aattgtcacc      60
atcacatgcc aggcaagcca ggacattggt aattggttat catggtatca gcagaaacca     120
gggaaatcgc ctcagctcct gatctatggt gcaaccagct ggcagatgg ggtcccatca      180 aggttcagcg ccagtagatc tggcacacag tactctctta agatcagcag actgcaggtt     240
```

```
gaagattttg gaatctttta ctgtctacag ggtcaaagta ctccgtacac gtttggagct    300
gggaccaagc tggaactgaa a                                              321
```

<210> SEQ ID NO 10
<211> LENGTH: 363
<212> TYPE: DNA
<213> ORGANISM: Artificial Sequence
<220> FEATURE:
<223> OTHER INFORMATION: HCVR DNA of 1974

<400> SEQUENCE: 10

```
gacgtgcagc tggtggaatc tgaggaggc ttagtgcagc ctggaaggtc cctgaaactc     60
tcctgtgcag cctcaggatt cactttcagt gcctattaca tggcctgggt ccgccaggct   120
ccaacgaagg gtctggagtg gtcgcatcc attaattatg atggtgctaa cactttctat   180
cgcgactccg tgaagggccg attcactgtc tccagagata tgcaagaag cagcctatac   240 ctacaaatgg acagtctgag gtctgaggac acggccactt attactgtac aacagaggct   300
tacggatata actcaaattg gtttggttac tggggccaag gcactctggt cactgtctcg   360
agc                                                                 363
```

<210> SEQ ID NO 11
<211> LENGTH: 214
<212> TYPE: PRT
<213> ORGANISM: Artificial Sequence
<220> FEATURE:
<223> OTHER INFORMATION: 1974 LC kappa full

<400> SEQUENCE: 11

Asp Ile Gln Met Thr Gln Ser Pro Ala Ser Leu Pro Ala Ser Pro Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Ala
    50                  55                  60

Ser Arg Ser Gly Thr Gln Tyr Ser Leu Lys Ile Ser Arg Leu Gln Val
65                  70                  75                  80

Glu Asp Phe Gly Ile Phe Tyr Cys Leu Gln Gly Ser Thr Pro Tyr
                85                  90                  95

Thr Phe Gly Ala Gly Thr Lys Leu Glu Leu Lys Arg Thr Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

-continued

210

<210> SEQ ID NO 12
<211> LENGTH: 445
<212> TYPE: PRT
<213> ORGANISM: Artificial Sequence
<220> FEATURE:
<223> OTHER INFORMATION: 1974 HC mIgG1 full

<400> SEQUENCE: 12

Asp Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Ala Tyr
            20                  25                  30

Tyr Met Ala Trp Val Arg Gln Ala Pro Thr Lys Gly Leu Glu Trp Val
        35                  40                  45

Ala Ser Ile Asn Tyr Asp Gly Ala Asn Thr Phe Tyr Arg Asp Ser Val
    50                  55                  60

Lys Gly Arg Phe Thr Val Ser Arg Asp Asn Ala Arg Ser Ser Leu Tyr
65                  70                  75                  80

Leu Gln Met Asp Ser Leu Arg Ser Glu Asp Thr Ala Thr Tyr Tyr Cys
                85                  90                  95

Thr Thr Glu Ala Tyr Gly Tyr Asn Ser Asn Trp Phe Gly Tyr Trp Gly
            100                 105                 110

Gln Gly Thr Leu Val Thr Val Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr

```
                355                 360                 365
Asp Phe Phe Pro Glu Asp Ile Thr Val Glu Trp Gln Trp Asn Gly Gln
            370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445

<210> SEQ ID NO 13
<211> LENGTH: 223
<212> TYPE: PRT
<213> ORGANISM: Artificial Sequence
<220> FEATURE:
<223> OTHER INFORMATION: 1974 HC mFabno hinge full

<400> SEQUENCE: 13

Asp Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Ala Tyr
            20                  25                  30

Tyr Met Ala Trp Val Arg Gln Ala Pro Thr Lys Gly Leu Glu Trp Val
        35                  40                  45

Ala Ser Ile Asn Tyr Asp Gly Ala Asn Thr Phe Tyr Arg Asp Ser Val
    50                  55                  60

Lys Gly Arg Phe Thr Val Ser Arg Asp Asn Ala Arg Ser Ser Leu Tyr
65                  70                  75                  80

Leu Gln Met Asp Ser Leu Arg Ser Glu Asp Thr Ala Thr Tyr Tyr Cys
                85                  90                  95

Thr Thr Glu Ala Tyr Gly Tyr Asn Ser Asn Trp Phe Gly Tyr Trp Gly
            100                 105                 110

Gln Gly Thr Leu Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys
    210                 215                 220

<210> SEQ ID NO 14
<211> LENGTH: 642
<212> TYPE: DNA
<213> ORGANISM: Artificial Sequence
<220> FEATURE:
<223> OTHER INFORMATION: 1974 LC DNA kappa full

<400> SEQUENCE: 14
```

```
gacatccaga tgacccagtc tcctgcctcc ctgcctgcat ccccggaaga aattgtcacc        60
atcacatgcc aggcaagcca ggacattggt aattggttat catggtatca gcagaaacca       120
gggaaatcgc tcagctcct  gatctatggt gcaaccagct tggcagatgg ggtcccatca       180
aggttcagcg ccagtagatc tggcacacag tactctctta agatcagcag actgcaggtt       240
gaagattttg gaatctttta ctgtctacag ggtcaaagta ctccgtacac gtttggagct       300
gggaccaagc tggaactgaa acgtacggat gctgcaccaa ctgtatccat cttcccacca       360
tccagtgagc agttaacatc tggaggtgcc tcagtcgtgt gcttcttgaa caacttctac       420
cccaaagaca tcaatgtcaa gtggaagatt gatggcagtg aacgacaaaa tggcgtcctg       480
aacagttgga ctgatcagga cagcaaagac agcacctaca gcatgagcag caccctcacg       540
ttgaccaagg acgagtatga acgacataac agctatacct gtgaggccac tcacaagaca       600
tcaacttcac ccattgtcaa gagcttcaac aggaatgagt gt                          642

<210> SEQ ID NO 15
<211> LENGTH: 1335
<212> TYPE: DNA
<213> ORGANISM: Artificial Sequence
<220> FEATURE:
<223> OTHER INFORMATION: 1974 HC DNA mIgG1 full

<400> SEQUENCE: 15
gacgtgcagc tggtggaatc tggaggaggc ttagtgcagc ctggaaggtc cctgaaactc        60
tcctgtgcag cctcaggatt cactttcagt gcctattaca tggcctgggt ccgccaggct       120
ccaacgaagg gtctggagtg ggtcgcatcc attaattatg atggtgctaa cacttttctat      180 cgcgactccg tgaagggccg attcactgtc tccagagata tgcaagaag  cagcctatac       240 ctacaaatgg acagtctgag gtctgaggac acggccactt attactgtac aacagaggct       300
tacggatata actcaaattg gtttggttac tggggccaag gcactctggt cactgtctcg       360
agtgccaaaa cgacaccccc atctgtctat ccactggccc ctggatctgc tgcccaaact       420
aactccatgg tgaccctggg atgcctggtc aagggctatt tccctgagcc agtgacagtg       480
acctggaact ctggatccct gtccagcggt gtgcacacct tcccagctgt cctgcagtct       540
gacctctaca ctctgagcag ctcagtgact gtcccctcca gcacctggcc cagcgagacc       600
gtcacctgca acgttgccca cccggccagc agcaccaagg tggacaagaa aattgtgccc       660
agggattgtg gttgtaagcc ttgcatatgt acagtcccag aagtatcatc tgtcttcatc       720
ttccccccaa agcccaagga tgtgctcacc attactctga ctcctaaggt cacgtgtgtt       780
gtggtagaca tcagcaagga tgatcccgag gtccagttca gctggtttgt agatgatgtg       840
gaggtgcaca cagctcagac gcaaccccgg gaggagcagt tcaacagcac tttccgctca       900
gtcagtgaac ttcccatcat gcaccaggac tggctcaatg gcaaggagtt caaatgcagg       960
gtcaacagtg cagcttttcc tgccccatc  gagaaaacca tctccaaaac caaaggcaga      1020
ccgaaggctc cacaggtgta caccattcca cctcccaagg agcagatggc caaggataaa      1080
gtcagtctga cctgcatgat aacagacttc ttccctgaag acattactgt ggagtggcag      1140
tggaatgggc agccagcgga gaactacaag aacactcagc ccatcatgga cacagatggc      1200
tcttacttcg tctacagcaa gctcaatgtg cagaagagca ctgggaggc  aggaaatact      1260 ttcacctgct ctgtgttaca tgagggcctg cacaaccacc atactgagaa gagcctctcc      1320
cactctcctg gtaaa                                                       1335
```

<210> SEQ ID NO 16
<211> LENGTH: 669
<212> TYPE: DNA
<213> ORGANISM: Artificial Sequence
<220> FEATURE:
<223> OTHER INFORMATION: 1974 HC DNA mFabno hinge full

<400> SEQUENCE: 16

```
gacgtgcagc tggtggaatc tggaggaggc ttagtgcagc tggaaggtc cctgaaactc      60
tcctgtgcag cctcaggatt cactttcagt gcctattaca tggcctgggt ccgccaggct    120
ccaacgaagg gtctggagtg ggtcgcatcc attaattatg atggtgctaa cactttctat    180
cgcgactccg tgaagggccg attcactgtc tccagagata tgcaagaag cagcctatac     240
ctacaaatgg acagtctgag gtctgaggac acggccactt attactgtac aacagaggct    300
tacggatata actcaaattg gtttggttac tggggccaag gcactctggt cactgtctcg    360
agtgccaaaa cgacaccccc atctgtctat ccactggccc ctggatctgc tgcccaaact    420
aactccatgg tgaccctggg atgcctggtc aagggctatt ccctgagcc agtgacagtg     480
acctggaact ctggatccct gtccagcggt gtgcacacct tcccggctgt cctgcaatct    540
gacctctaca ctctgagcag ctcagtgact gtccccctcca gcacctggcc cagcgagacc   600
gtcacctgca acgttgccca cccggccagc agcaccaagg tggacaagaa aattgtgccc    660
agggattgt                                                            669
```

<210> SEQ ID NO 17
<211> LENGTH: 7
<212> TYPE: PRT
<213> ORGANISM: Artificial Sequence
<220> FEATURE:
<223> OTHER INFORMATION: LCDR2 of 1979

<400> SEQUENCE: 17

Gly Thr Thr Ser Leu Ala Asp
1               5

<210> SEQ ID NO 18
<211> LENGTH: 10
<212> TYPE: PRT
<213> ORGANISM: Artificial Sequence
<220> FEATURE:
<223> OTHER INFORMATION: LCDR3 of 1979

<400> SEQUENCE: 18

Leu Gln Ala Tyr Ser Thr Pro Phe Thr Phe
1               5                   10

<210> SEQ ID NO 19
<211> LENGTH: 5
<212> TYPE: PRT
<213> ORGANISM: Artificial Sequence
<220> FEATURE:
<223> OTHER INFORMATION: HCDR1 of 1979

<400> SEQUENCE: 19

Asn Ser Tyr Trp Asp
1               5

<210> SEQ ID NO 20
<211> LENGTH: 16
<212> TYPE: PRT
<213> ORGANISM: Artificial Sequence
<220> FEATURE:
<223> OTHER INFORMATION: HCDR2 of 1979

<400> SEQUENCE: 20

Tyr Ile Asn Tyr Ser Gly Ser Thr Gly Tyr Asn Pro Ser Leu Lys Ser
1               5                   10                  15

<210> SEQ ID NO 21
<211> LENGTH: 12
<212> TYPE: PRT
<213> ORGANISM: Artificial Sequence
<220> FEATURE:
<223> OTHER INFORMATION: HCDR3 of 1979

<400> SEQUENCE: 21

Gly Thr Tyr Gly Tyr Asn Ala Tyr His Phe Asp Tyr
1               5                   10

<210> SEQ ID NO 22
<211> LENGTH: 107
<212> TYPE: PRT
<213> ORGANISM: Artificial Sequence
<220> FEATURE:
<223> OTHER INFORMATION: LCVR of 1979

<400> SEQUENCE: 22

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
                20                  25                  30

Leu Ser Trp Tyr Gln Gln Lys Pro Gly Lys Ser Pro His Leu Leu Ile
            35                  40                  45

Tyr Gly Thr Thr Ser Leu Ala Asp Gly Val Pro Ser Arg Phe Ser Gly
        50                  55                  60

Ser Arg Ser Gly Thr Gln Tyr Ser Leu Lys Ile Ser Gly Leu Gln Val
65                  70                  75                  80

Ala Asp Ile Gly Ile Tyr Val Cys Leu Gln Ala Tyr Ser Thr Pro Phe
                85                  90                  95

Thr Phe Gly Ser Gly Thr Lys Leu Glu Ile Lys
            100                 105

<210> SEQ ID NO 23
<211> LENGTH: 120
<212> TYPE: PRT
<213> ORGANISM: Artificial Sequence
<220> FEATURE:
<223> OTHER INFORMATION: HCVR of 1979

<400> SEQUENCE: 23

Glu Val His Leu Val Glu Ser Gly Pro Gly Leu Val Lys Pro Ser Gln
1               5                   10                  15

Ser Leu Ser Leu Thr Cys Ser Val Thr Gly Tyr Ser Ile Thr Asn Ser
                20                  25                  30

Tyr Trp Asp Trp Ile Arg Lys Phe Pro Gly Asn Lys Met Glu Trp Met
            35                  40                  45

Gly Tyr Ile Asn Tyr Ser Gly Ser Thr Gly Tyr Asn Pro Ser Leu Lys
        50                  55                  60

Ser Arg Ile Ser Ile Ser Arg Asp Thr Ser Asn Gln Phe Phe Leu
65                  70                  75                  80

Gln Leu Asn Ser Ile Thr Thr Glu Asp Thr Ala Thr Tyr Tyr Cys Ala
                85                  90                  95

Arg Gly Thr Tyr Gly Tyr Asn Ala Tyr His Phe Asp Tyr Trp Gly Arg

Gly Val Met Val Thr Val Ser Ser
            115                 120

<210> SEQ ID NO 24
<211> LENGTH: 321
<212> TYPE: DNA
<213> ORGANISM: Artificial Sequence
<220> FEATURE:
<223> OTHER INFORMATION: LCVR DNA of 1979

<400> SEQUENCE: 24
gacatccaaa tgacacagtc tcctgcctcc ctgtctgcat ctctgggaaga aattgtcacc    60 attacatgcc aggcaagcca ggacattggt aattggttat catggtatca gcagaaacca   120
gggaaatctc ctcacctcct gatctatggt accaccagct tggcagatgg ggtcccatca   180
aggttcagcg gcagtagatc tggtacacag tattctctta agatcagcgg actacaggtt   240
gcagatattg gaatctatgt ctgtctacag gcttatagta ctccattcac gttcggctca   300
gggacaaagc tggaaataaa a                                              321

<210> SEQ ID NO 25
<211> LENGTH: 360
<212> TYPE: DNA
<213> ORGANISM: Artificial Sequence
<220> FEATURE:
<223> OTHER INFORMATION: HCVR DNA of 1979

<400> SEQUENCE: 25
gaggtgcacc tggtggagtc tggacctggc cttgtgaaac cctcacagtc actctccctc    60
acctgttctg tcactggtta ctccatcact aatagttact gggactggat ccggaagttc   120
ccaggaaata aaatggagtg gatgggatac ataaactaca gtggtagcac tggctacaac   180
ccatctctca aaagtcgaat ctccattagt agagacacat cgaacaatca gttcttcctg   240
cagctgaact ctataactac tgaggacaca gccacatatt actgtgcacg agggacctat   300
gggtataacg cctaccactt tgattactgg ggccgaggag tcatggtcac agtctcgagc   360

<210> SEQ ID NO 26
<211> LENGTH: 214
<212> TYPE: PRT
<213> ORGANISM: Artificial Sequence
<220> FEATURE:
<223> OTHER INFORMATION: 1979 LC Kappa full

<400> SEQUENCE: 26

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro His Leu Leu Ile
        35                  40                  45

Tyr Gly Thr Thr Ser Leu Ala Asp Gly Val Pro Ser Arg Phe Ser Gly
    50                  55                  60

Ser Arg Ser Gly Thr Gln Tyr Ser Leu Lys Ile Ser Gly Leu Gln Val
65                  70                  75                  80

Ala Asp Ile Gly Ile Tyr Val Cys Leu Gln Ala Tyr Ser Thr Pro Phe
                85                  90                  95

Thr Phe Gly Ser Gly Thr Lys Leu Glu Ile Lys Arg Thr Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
        210

<210> SEQ ID NO 27
<211> LENGTH: 444
<212> TYPE: PRT
<213> ORGANISM: Artificial Sequence
<220> FEATURE:
<223> OTHER INFORMATION: 1979 HC mIgG1 full

<400> SEQUENCE: 27

Glu Val His Leu Val Glu Ser Gly Pro Gly Leu Val Lys Pro Ser Gln
1               5                   10                  15

Ser Leu Ser Leu Thr Cys Ser Val Thr Gly Tyr Ser Ile Thr Asn Ser
            20                  25                  30

Tyr Trp Asp Trp Ile Arg Lys Phe Pro Gly Asn Lys Met Glu Trp Met
        35                  40                  45

Gly Tyr Ile Asn Tyr Ser Gly Thr Gly Tyr Asn Pro Ser Leu Lys
    50                  55                  60

Ser Arg Ile Ser Ile Ser Arg Asp Thr Ser Asn Asn Gln Phe Phe Leu
65                  70                  75                  80

Gln Leu Asn Ser Ile Thr Thr Glu Asp Thr Ala Thr Tyr Tyr Cys Ala
                85                  90                  95

Arg Gly Thr Tyr Gly Tyr Asn Ala Tyr His Phe Asp Tyr Trp Gly Arg
            100                 105                 110

Gly Val Met Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
        130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
        210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

```
Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
275                 280                 285

Arg Glu Glu Gln Phe Asn Ser Thr Phe Arg Ser Val Ser Glu Leu Pro
        290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440

<210> SEQ ID NO 28
<211> LENGTH: 222
<212> TYPE: PRT
<213> ORGANISM: Artificial Sequence
<220> FEATURE:
<223> OTHER INFORMATION: 1979 HC mFabno hinge full

<400> SEQUENCE: 28

Glu Val His Leu Val Glu Ser Gly Pro Gly Leu Val Lys Pro Ser Gln
1               5                   10                  15

Ser Leu Ser Leu Thr Cys Ser Val Thr Gly Tyr Ser Ile Thr Asn Ser
            20                  25                  30

Tyr Trp Asp Trp Ile Arg Lys Phe Pro Gly Asn Lys Met Glu Trp Met
        35                  40                  45

Gly Tyr Ile Asn Tyr Ser Gly Ser Thr Gly Tyr Asn Pro Ser Leu Lys
    50                  55                  60

Ser Arg Ile Ser Ile Ser Arg Asp Thr Ser Asn Asn Gln Phe Phe Leu
65                  70                  75                  80

Gln Leu Asn Ser Ile Thr Thr Glu Asp Thr Ala Thr Tyr Tyr Cys Ala
                85                  90                  95

Arg Gly Thr Tyr Gly Tyr Asn Ala Tyr His Phe Asp Tyr Trp Gly Arg
            100                 105                 110

Gly Val Met Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175
```

Leu Gln Ser Asp Leu Tyr Thr Leu Ser Ser Val Thr Val Pro Ser
                180                 185                 190

Ser Thr Trp Pro Ser Glu Thr Val Thr Cys Asn Val Ala His Pro Ala
            195                 200                 205

Ser Ser Thr Lys Val Asp Lys Lys Ile Val Pro Arg Asp Cys
        210                 215                 220

<210> SEQ ID NO 29
<211> LENGTH: 642
<212> TYPE: DNA
<213> ORGANISM: Artificial Sequence
<220> FEATURE:
<223> OTHER INFORMATION: 1979 LC DNA Kappa full

<400> SEQUENCE: 29

| | | | | | |
|---|---|---|---|---|---|
| gacatccaaa | tgacacagtc | tcctgcctcc | ctgtctgcat | ctctggaaga | aattgtcacc | 60 |
| attacatgcc | aggcaagcca | ggacattggt | aattggttat | catggtatca | gcagaaacca | 120 |
| gggaaatctc | ctcacctcct | gatctatggt | accaccagct | tggcagatgg | ggtcccatca | 180 |
| aggttcagcg | gcagtagatc | tggtacacag | tattctctta | agatcagcgg | actacaggtt | 240 |
| gcagatattg | aatctatgt  | ctgtctacag | gcttatagta | ctccattcac | gttcggctca | 300 |
| gggacaaagc | tggaaataaa | acgtacggat | gctgcaccaa | ctgtatccat | cttcccacca | 360 |
| tccagtgagc | agttaacatc | tggaggtgcc | tcagtcgtgt | gcttcttgaa | caacttctac | 420 |
| cccaaagaca | tcaatgtcaa | gtggaagatt | gatggcagtg | aacgacaaaa | tggcgtcctg | 480 |
| aacagttgga | ctgatcagga | cagcaaagac | agcacctaca | gcatgagcag | caccctcacg | 540 |
| ttgaccaagg | acgagtatga | acgacataac | agctatacct | gtgaggccac | tcacaagaca | 600 |
| tcaacttcac | ccattgtcaa | gagcttcaac | aggaatgagt | gt | | 642 |

<210> SEQ ID NO 30
<211> LENGTH: 1332
<212> TYPE: DNA
<213> ORGANISM: Artificial Sequence
<220> FEATURE:
<223> OTHER INFORMATION: 1979 HC DNA mIgG1 full

<400> SEQUENCE: 30

| | | | | | |
|---|---|---|---|---|---|
| gaggtgcacc | tggtggagtc | tggacctggc | cttgtgaaac | cctcacagtc | actctccctc | 60 |
| acctgttctg | tcactggtta | ctccatcact | aatagttact | gggactggat | ccggaagttc | 120 |
| ccaggaaata | aaatggagtg | gatgggatac | ataaactaca | gtggtagcac | tggctacaac | 180 |
| ccatctctca | aaagtcgaat | ctccattagt | agagacacat | cgaacaatca | gttcttcctg | 240 |
| cagctgaact | ctataactac | tgaggacaca | gccacatatt | actgtgcacg | agggacctat | 300 |
| ggtataacg  | cctaccactt | tgattactgg | ggccgaggag | tcatggtcac | agtctcgagt | 360 |
| gccaaaacga | cacccccatc | tgtctatcca | ctggcccctg | gatctgctgc | ccaaactaac | 420 |
| tccatggtga | ccctgggatg | cctggtcaag | ggctatttcc | ctgagccagt | gacagtgacc | 480 |
| tggaactctg | gatccctgtc | cagcggtgtg | cacaccttcc | cagctgtcct | gcagtctgac | 540 |
| ctctacactc | tgagcagctc | agtgactgtc | cctccagca  | cctggcccag | cgagaccgtc | 600 |
| acctgcaacg | ttgcccaccc | ggccagcagc | accaaggtgg | acaagaaaat | tgtgcccagg | 660 |
| gattgtggtt | gtaagccttg | catatgtaca | gtcccagaag | tatcatctgt | cttcatcttc | 720 |
| cccccaaagc | ccaaggatgt | gctcaccatt | actctgactc | ctaaggtcac | gtgtgttgtg | 780 |
| gtagacatca | gcaaggatga | tcccgaggtc | cagttcagct | ggtttgtaga | tgatgtggag | 840 |

```
gtgcacacag ctcagacgca accccgggag gagcagttca acagcacttt ccgctcagtc    900
agtgaacttc ccatcatgca ccaggactgg ctcaatggca aggagttcaa atgcagggtc    960
aacagtgcag cttccctgc ccccatcgag aaaccatct ccaaaaccaa aggcagaccg   1020
aaggctccac aggtgtacac cattccacct cccaaggagc agatggccaa ggataaagtc   1080
agtctgacct gcatgataac agacttcttc cctgaagaca ttactgtgga gtggcagtgg   1140
aatgggcagc cagcggagaa ctacaagaac actcagccca tcatggacac agatggctct   1200
tacttcgtct acagcaagct caatgtgcag aagagcaact gggaggcagg aaatactttc   1260
acctgctctg tgttacatga gggcctgcac aaccaccata ctgagaagag cctctcccac   1320
tctcctggta aa   1332
```

```
<210> SEQ ID NO 31
<211> LENGTH: 666
<212> TYPE: DNA
<213> ORGANISM: Artificial Sequence
<220> FEATURE:
<223> OTHER INFORMATION: 1979 HC DNA mFabno hinge full

<400> SEQUENCE: 31
gaggtgcacc tggtggagtc tggacctggc cttgtgaaac cctcacagtc actctccctc     60
acctgttctg tcactggtta ctccatcact aatagttact gggactggat ccggaagttc    120
ccaggaaata aaatggagtg gatgggatac ataaactaca gtggtagcac tggctacaac    180
ccatctctca aaagtcgaat ctccattagt agagacacat cgaacaatca gttcttcctg    240
cagctgaact ctataactac tgaggacaca gccacatatt actgtgcacg agggacctat    300
gggtataacg cctaccactt tgattactgg ggccgaggag tcatggtcac agtctcgagt    360
gccaaaacga cacccccatc tgtctatcca ctggcccctg gatctgctgc ccaaactaac    420
tccatggtga ccctgggatg cctggtcaag ggctatttcc ctgagccagt gacagtgacc    480
tggaactctg gatccctgtc cagcggtgtg cacaccttcc cggctgtcct gcaatctgac    540
ctctacactc tgagcagctc agtgactgtc ccctccagca cctggcccag cgagaccgtc    600
acctgcaacg ttgcccaccc ggccagcagc accaaggtgg acaagaaaat tgtgcccagg    660
gattgt    666
```

```
<210> SEQ ID NO 32
<211> LENGTH: 235
<212> TYPE: PRT
<213> ORGANISM: Rattus norvegicus

<400> SEQUENCE: 32

Met Ser Thr Glu Ser Met Ile Arg Asp Val Glu Leu Ala Glu Ala
1               5                   10                  15

Leu Pro Lys Lys Met Gly Gly Leu Gln Asn Ser Arg Arg Cys Leu Cys
            20                  25                  30

Leu Ser Leu Phe Ser Phe Leu Leu Val Ala Gly Ala Thr Thr Leu Phe
        35                  40                  45

Cys Leu Leu Asn Phe Gly Val Ile Gly Pro Asn Lys Glu Glu Lys Phe
    50                  55                  60

Pro Asn Gly Leu Pro Leu Ile Ser Ser Met Ala Gln Thr Leu Thr Leu
65                  70                  75                  80

Arg Ser Ser Ser Gln Asn Ser Ser Asp Lys Pro Val Ala His Val Val
                85                  90                  95
```

Ala Asn His Gln Ala Glu Glu Gln Leu Glu Trp Leu Ser Gln Arg Ala
            100                 105                 110

Asn Ala Leu Leu Ala Asn Gly Met Asp Leu Lys Asp Asn Gln Leu Val
            115                 120                 125

Val Pro Ala Asp Gly Leu Tyr Leu Ile Tyr Ser Gln Val Leu Phe Lys
130                 135                 140

Gly Gln Gly Cys Pro Asp Tyr Val Leu Leu Thr His Thr Val Ser Arg
145                 150                 155                 160

Phe Ala Ile Ser Tyr Gln Glu Lys Val Ser Leu Leu Ser Ala Ile Lys
                165                 170                 175

Ser Pro Cys Pro Lys Asp Thr Pro Glu Gly Ala Glu Leu Lys Pro Trp
            180                 185                 190

Tyr Glu Pro Met Tyr Leu Gly Gly Val Phe Gln Leu Glu Lys Gly Asp
            195                 200                 205

Leu Leu Ser Ala Glu Val Asn Leu Pro Lys Tyr Leu Asp Ile Thr Glu
210                 215                 220

Ser Gly Gln Val Tyr Phe Gly Val Ile Ala Leu
225                 230                 235

<210> SEQ ID NO 33
<211> LENGTH: 235
<212> TYPE: PRT
<213> ORGANISM: Mus musculus

<400> SEQUENCE: 33

Met Ser Thr Glu Ser Met Ile Arg Asp Val Glu Leu Ala Glu Glu Ala
1               5                   10                  15

Leu Pro Gln Lys Met Gly Gly Phe Gln Asn Ser Arg Arg Cys Leu Cys
            20                  25                  30

Leu Ser Leu Phe Ser Phe Leu Leu Val Ala Gly Ala Thr Thr Leu Phe
            35                  40                  45

Cys Leu Leu Asn Phe Gly Val Ile Gly Pro Gln Arg Asp Glu Lys Phe
50                  55                  60

Pro Asn Gly Leu Pro Leu Ile Ser Ser Met Ala Gln Thr Leu Thr Leu
65                  70                  75                  80

Arg Ser Ser Ser Gln Asn Ser Ser Asp Lys Pro Val Ala His Val Val
                85                  90                  95

Ala Asn His Gln Val Glu Glu Gln Leu Glu Trp Leu Ser Gln Arg Ala
            100                 105                 110

Asn Ala Leu Leu Ala Asn Gly Met Asp Leu Lys Asp Asn Gln Leu Val
            115                 120                 125

Val Pro Ala Asp Gly Leu Tyr Leu Val Tyr Ser Gln Val Leu Phe Lys
130                 135                 140

Gly Gln Gly Cys Pro Asp Tyr Val Leu Leu Thr His Thr Val Ser Arg
145                 150                 155                 160

Phe Ala Ile Ser Tyr Gln Glu Lys Val Asn Leu Leu Ser Ala Val Lys
                165                 170                 175

Ser Pro Cys Pro Lys Asp Thr Pro Glu Gly Ala Glu Leu Lys Pro Trp
            180                 185                 190

Tyr Glu Pro Ile Tyr Leu Gly Gly Val Phe Gln Leu Glu Lys Gly Asp
            195                 200                 205

Gln Leu Ser Ala Glu Val Asn Leu Pro Lys Tyr Leu Asp Phe Ala Glu
210                 215                 220

Ser Gly Gln Val Tyr Phe Gly Val Ile Ala Leu
225                 230                 235

<210> SEQ ID NO 34
<211> LENGTH: 233
<212> TYPE: PRT
<213> ORGANISM: Homo sapiens

<400> SEQUENCE: 34

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 35
<211> LENGTH: 158
<212> TYPE: PRT
<213> ORGANISM: Homo sapiens

<400> SEQUENCE: 35

Ser Val Arg Ser Ser Arg Thr Pro Ser Asp Lys Pro Val Ala His
1               5                   10                  15

Val Val Ala Asn Pro Gln Ala Glu Gly Gln Leu Gln Trp Leu Asn Arg
                20                  25                  30

Arg Ala Asn Ala Leu Leu Ala Asn Gly Val Glu Leu Arg Asp Asn Gln
            35                  40                  45

Leu Val Val Pro Ser Glu Gly Leu Tyr Leu Ile Tyr Ser Gln Val Leu
        50                  55                  60

Phe Lys Gly Gln Gly Cys Pro Ser Thr His Val Leu Leu Thr His Thr
65                  70                  75                  80

Ile Ser Arg Ile Ala Val Ser Tyr Gln Thr Lys Val Asn Leu Leu Ser
                85                  90                  95

```
Ala Ile Lys Ser Pro Cys Gln Arg Glu Thr Pro Glu Gly Ala Glu Ala
            100                 105                 110

Lys Pro Trp Tyr Glu Pro Ile Tyr Leu Gly Gly Val Phe Gln Leu Glu
        115                 120                 125

Lys Gly Asp Arg Leu Ser Ala Glu Ile Asn Arg Pro Asp Tyr Leu Asp
    130                 135                 140

Phe Ala Glu Ser Gly Gln Val Tyr Phe Gly Ile Ile Ala Leu
145                 150                 155

<210> SEQ ID NO 36
<211> LENGTH: 157
<212> TYPE: PRT
<213> ORGANISM: Homo sapiens

<400> SEQUENCE: 36

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 37
<211> LENGTH: 144
<212> TYPE: PRT
<213> ORGANISM: Artificial Sequence
<220> FEATURE:
<223> OTHER INFORMATION: Extracellular domain of human TNFR1 with N54D
      and C182S mutations

<400> SEQUENCE: 37

Gly Ser Val Cys Pro Gln Gly Lys Tyr Ile His Pro Gln Asp Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45
```

```
Phe Thr Ala Ser Glu Asn His Leu Arg His Cys Leu Ser Cys Ser Lys
    50                  55                  60
Cys Arg Lys Glu Met Gly Gln Val Glu Ile Ser Ser Cys Thr Val Asp
65                  70                  75                  80
Arg Asp Thr Val Cys Gly Cys Arg Lys Asn Gln Tyr Arg His Tyr Trp
                85                  90                  95
Ser Glu Asn Leu Phe Gln Cys Phe Asn Cys Ser Leu Cys Leu Asn Gly
                100                 105                 110
Thr Val His Leu Ser Cys Gln Glu Lys Gln Asn Thr Val Cys Thr Cys
            115                 120                 125
His Ala Gly Phe Phe Leu Arg Glu Asn Glu Cys Val Ser Ser Ser Asn
        130                 135                 140

<210> SEQ ID NO 38
<211> LENGTH: 143
<212> TYPE: PRT
<213> ORGANISM: Artificial Sequence
<220> FEATURE:
<223> OTHER INFORMATION: Extracellular domain of human TNFR1 with N54D
      and C182S mutations

<400> SEQUENCE: 38

Ser Val Cys Pro Gln Gly Lys Tyr Ile His Pro Gln Asp Asn Ser Ile
1               5                   10                  15
Cys Cys Thr Lys Cys His Lys Gly Thr Tyr Leu Tyr Asn Asp Cys Pro
            20                  25                  30
Gly Pro Gly Gln Asp Thr Asp Cys Arg Glu Cys Glu Ser Gly Ser Phe
        35                  40                  45
Thr Ala Ser Glu Asn His Leu Arg His Cys Leu Ser Cys Ser Lys Cys
    50                  55                  60
Arg Lys Glu Met Gly Gln Val Glu Ile Ser Ser Cys Thr Val Asp Arg
65                  70                  75                  80
Asp Thr Val Cys Gly Cys Arg Lys Asn Gln Tyr Arg His Tyr Trp Ser
                85                  90                  95
Glu Asn Leu Phe Gln Cys Phe Asn Cys Ser Leu Cys Leu Asn Gly Thr
                100                 105                 110
Val His Leu Ser Cys Gln Glu Lys Gln Asn Thr Val Cys Thr Cys His
            115                 120                 125
Ala Gly Phe Phe Leu Arg Glu Asn Glu Cys Val Ser Ser Ser Asn
        130                 135                 140
```

ANTIBODY AGAINST TRIMERIC TNFα COMPLEX

REFERENCE TO AN ELECTRONIC SEQUENCE LISTING

The contents of the electronic sequence listing (1089-0008US1_SL.txt; Size: 44 KB; and Date of Creation Jun. 17, 2019) is herein incorporated by reference in its entirety.

FIELD OF THE INVENTION

This invention relates to antibodies, particularly antibodies recognising a specific epitope, which may be used to screen for small molecule modulators of TNFα. The invention relates to antibodies which selectively bind to such TNFα small molecule modulator complexes, and uses of such antibodies. The present invention also relates to assays for identifying new modulators of TNFα using said antibodies.

BACKGROUND OF THE INVENTION

The Tumour Necrosis Factor (TNF) superfamily is a family of proteins that share a primary function of regulating cell survival and cell death. Members of the TNF superfamily share a common core motif, which consists of two antiparallel β-pleated sheets with antiparallel β-strands, forming a "jelly roll" β-structure. Another common feature shared by members of the TNF superfamily is the formation of homo- or heterotrimeric complexes. It is these trimeric forms of the TNF superfamily members that bind to, and activate, specific TNF superfamily receptors.

TNFα is the archetypal member of the TNF superfamily. Dysregulation of TNFα production has been implicated in a number of pathological conditions of significant medical importance. For example, TNFα has been implicated in rheumatoid arthritis, inflammatory bowel diseases (including Crohn's disease), psoriasis, Alzheimer's disease (AD), Parkinson's disease (PD), pain, epilepsy, osteoporosis, asthma, systemic lupus erythematosus (SLE) and multiple sclerosis (MS). Other members of the TNF superfamily have also been implicated in pathological conditions, including autoimmune disease.

Conventional antagonists of TNF superfamily members are macromolecular and act by inhibiting the binding of the TNF superfamily member to its receptor. Examples of conventional antagonists include anti-TNFα antibodies, particularly monoclonal antibodies, such as infliximab (Remicade®), adalimumab (Humira®) and certolizumab pegol (Cimzia®), or soluble TNFα receptor fusion proteins, such as etanercept (Enbrel®).

SUMMARY OF THE INVENTION

The present inventors have identified classes of small molecular entities (SME) that modulate TNFα. These compounds act by binding to the homotrimeric form of TNFα, and inducing and/or stabilising a conformational change in the homotrimer of TNFα. For example, homotrimers of TNFα with the compound bound can bind to TNFα receptors, but are less able, or unable, to initiate signalling downstream of the TNFα receptor. These compounds can be used in the treatment of conditions mediated by TNFα.

The present inventors have developed antibodies that bind selectively to complexes comprising such compounds and TNFα. These antibodies may be used to identify further compounds that are capable of inhibiting TNFα in this manner, and may also be used as target engagement biomarkers.

Accordingly, the present invention provides an antibody which binds to an epitope comprising at least the following residues of trimeric TNFα:
(a) Y115
(b) Q149; and
(c) N137 or K98 or both,
wherein Y115 and Q149 are present on the C chain of trimeric TNFα, and N137 and K98 are present on the A chain of trimeric TNFα, and wherein the residue numbering is according to SEQ ID NO: 36.

The present invention also provides:
An antibody which competes for binding to TNFα with an antibody as defined above.
An isolated polynucleotide encoding an antibody of the invention.
An antibody of the invention for use in a method of treatment of the human or animal body by therapy.
A pharmaceutical composition comprising an antibody of the invention and a pharmaceutically acceptable adjuvant and/or carrier.
Use of an antibody of the invention as a target engagement biomarker for the detection of a compound-trimer complex in a sample obtained from a subject; wherein said antibody is detectable and said complex comprises trimeric TNFα and a compound that is capable of binding to trimeric TNFα, whereby the compound-trimer complex binds to the requisite receptor and modulates the signalling induced by the trimer through the receptor.
A method of detecting target engagement of a compound to trimeric TNFα, whereby the compound-trimer complex binds to the requisite receptor and modulates the signalling induced by the trimer through the receptor, said method comprising:
(a) obtaining a sample from a subject administered said compound;
(b) contacting an antibody of the invention to said sample and a control sample, wherein said antibody is detectable;
(c) determining the amount of binding of said detectable antibody to said sample and said control sample,
wherein binding of said detectable antibody to said sample greater than binding of said detectable antibody to said control sample indicates target engagement of said compound to said trimeric TNFα.
Use of an antibody of the invention in screening for a compound that elicits a conformational change in a TNFα trimer, wherein said conformational change modulates the signalling of the requisite receptor on binding of the trimeric TNFα.
A complex comprising a TNFα trimer and a compound that is bound thereto, whereby the compound-trimer complex binds to the requisite receptor and modulates the signalling induced by the trimer through the receptor, wherein said complex binds to an antibody of the invention with a $K_{D\text{-}ab}$ of 1 nM or less.
A compound that is capable of binding to a TNFα trimer to form a complex, whereby the compound-trimer complex binds to the requisite receptor and modulates the signalling induced by the trimer through the receptor, wherein the compound-trimer complex binds to an antibody of the invention with a $K_{D\text{-}ab}$ of 1 nM or less.

A method of identifying a compound that is capable of binding to a TNFα trimer and modulating signalling of the trimer through the requisite receptor, comprising the steps of:
(a) performing a binding assay to measure the binding affinity of a test compound-trimer complex comprising a TNFα trimer and a test compound to an antibody of the invention that selectively binds to said complex;
(b) comparing the binding affinity as measured in step (a) with the binding affinity of a different compound-trimer complex known to bind with high affinity to the antibody referred to in step (a); and
(c) selecting the compound present in the compound-trimer complex of step (a) if its measured binding affinity is acceptable when considered in the light of the comparison referred to in step (b).

BRIEF DESCRIPTION OF THE FIGURES

FIG. 1 highlights residues N168, I194, F220 and A221 on the crystal structure of human TNFα.

FIG. 2 shows results of HPLC experiments with the CA185_01974 mFab and compound (1). Peaks corresponding to excess Fab appear at a 1.5× and 2.0× excess. The stoichiometry was therefore determined to be 1 Fab: 1 TNFα trimer.

FIG. 3 shows results of HPLC experiments with the CA185_01979 mFab and compound (1). Again, peaks corresponding to excess Fab appear at a 1.5× and 2.0× excess. The stoichiometry was therefore also determined to be 1 Fab: 1 TNFα trimer.

FIG. 4 presents results of total TNFα ELISA with compounds (3), (4) and (5) using a commercial anti-TNFα polyclonal antibody.

FIG. 5 presents results of conformation specific TNFα ELISA with CA185_01974.0 and compounds (3), (4) and (5). Apo TNFα gave no signal in this assay, demonstrating the specific nature of the binding of antibody CA185_01974 to compound-bound TNFα.

FIG. 6 shows FACS histogram plots of staining with CA185_01974 and CA185_01979 at 1 and 10 μg/ml. These plots demonstrate that the antibodies only recognise TNFα which has been pre-incubated with compound (1). There is no staining with the DMSO control.

FIG. 7 shows FACS histogram plots of staining with CA185_01974 for a parental NS0 cell line and an engineered NS0 cell line, which overexpresses membrane TNFα. Cells were incubated with compound (1) or DMSO and stained with the antibody Fab fragment. Again, results indicate no staining for the DMSO control (for either the parental or engineered cell line). In the presence of compound (1) staining is, however, observed for the engineered cell line.

FIG. 8 shows sensograms for the determination of affinity values for CA185_01974 using cynomolgus TNFα. Controls (top panels) contained cynomolgus TNFα and DMSO. The bottom panels then present duplicated experiments for cynomolgus TNFα complexed with compound (4).

FIG. 9 shows sensograms for the determination of affinity values for CA185_01974 using human TNFα. Controls (top panels) contained human TNFα and DMSO. The bottom panels then present duplicated experiments for human TNFα complexed with compound (4).

FIG. 10 shows the structures of compounds (1)-(7).

FIG. 11 shows the structure of the Fab1974 bound to a complex of human TNFα asymmetric trimer, compound (2) and 2 human TNFR1 receptors.

FIG. 12 shows the same structure as FIG. 11, but with a symmetrical trimer (i.e. in the absence of compound) modelled in computationally. With this symmetric trimer, the A chain of the trimer retains the interaction with the Fab fragment. However, there is a steric clash between the Fab fragment and the C chain of the trimer.

FIG. 13 shows as spheres the experimentally determined epitope on the A and C chains of the TNFα trimer with CA185_1974.

FIG. 14 shows that CA185_1974 represents a suitable reagent for measuring target occupancy in a complex biological matrix. CA185_1974 was used as capture reagent to measure TNFα complexed with compound (2) using a high sensitivity ELISA, with a commercial anti-TNFα antibody as the detection reagent. TNFα pre-incubated with either excess compound of DMSO was spiked into neat human plasma (depleted or endogenous TNFα) and diluted to various concentrations. Signal generated by TNFα-small molecule inhibitor complex clearly increased proportionally with TNFα spike concentration. There was no significant detection of TNFα pre-incubate with DMSO (apo-TNF) at any TNFα spike concentrations tested. The TNFα-small molecule complex signal was significantly higher than apo-TNFα background with probability of at least 0.999 at TNFα concentrations of 25 pg/ml and above.

FIG. 15 shows single cycle kinetics of compound (1) binding to human TNFα directly immobilised (a) or via capture with CA185_1974 (b). Kinetics change from "slow on-slow off" with directly immobilised apo-TNF to "fast on-fast off" when captured via the conformation-selective antibody CA1974.

BRIEF DESCRIPTION OF THE SEQUENCE LISTING

SEQ ID NO: 1 shows the LCDR1 of CA185_01974.0.

SEQ ID NO: 2 shows the LCDR2 of CA185_01974.0.

SEQ ID NO: 3 shows the LCDR3 of CA185_01974.0.

SEQ ID NO: 4 shows the HCDR1 of CA185_01974.0.

SEQ ID NO: 5 shows the HCDR2 of CA185_01974.0.

SEQ ID NO: 6 shows the HCDR3 of CA185_01974.0.

SEQ ID NO: 7 shows the amino acid sequence of the LCVR of CA185_01974.0.

SEQ ID NO: 8 shows the amino acid sequence of the HCVR of CA185_01974.0.

SEQ ID NO: 9 shows the DNA sequence of the LCVR of CA185_01974.0.

SEQ ID NO: 10 shows the DNA sequence of the HCVR of CA185_01974.0.

SEQ ID NO: 11 shows the amino acid sequence of the kappa light chain of CA185_01974.0.

SEQ ID NO: 12 shows the amino acid sequence of the mIgG1 heavy chain of CA185_01974.0.

SEQ ID NO: 13 shows the amino acid sequence of the mFab (no hinge) heavy chain of CA185_01974.0.

SEQ ID NO: 14 shows the DNA sequence of the kappa light chain of CA185_01974.0.

SEQ ID NO: 15 shows the DNA sequence of the mIgG1 heavy chain of CA185_01974.0.

SEQ ID NO: 16 shows the DNA sequence of the mFab (no hinge) heavy chain of CA185_01974.0.

SEQ ID NO: 17 shows the LCDR2 of CA185_01979.0.

SEQ ID NO: 18 shows the LCDR3 of CA185_01979.0.

SEQ ID NO: 19 shows the HCDR1 of CA185_01979.0.

SEQ ID NO: 20 shows the HCDR2 of CA185_01979.0.

SEQ ID NO: 21 shows the HCDR3 of CA185_01979.0.

SEQ ID NO: 22 shows the amino acid sequence of the LCVR of CA185_01979.0.

SEQ ID NO: 23 shows the amino acid sequence of the HCVR of CA185_01979.0.

SEQ ID NO: 24 shows the DNA sequence of the LCVR of CA185_01979.0.

SEQ ID NO: 25 shows the DNA sequence of the HCVR of CA185_01979.0.

SEQ ID NO: 26 shows the amino acid sequence of the kappa light chain of CA185_01979.0.

SEQ ID NO: 27 shows the amino acid sequence of the mIgG1 heavy chain of CA185_01979.0.

SEQ ID NO: 28 shows the amino acid sequence of the mFab (no hinge) heavy chain of CA185_01979.0.

SEQ ID NO: 29 shows the DNA sequence of the kappa light chain of CA185_01979.0.

SEQ ID NO: 30 shows the DNA sequence of the mIgG1 heavy chain of CA185_01979.0.

SEQ ID NO: 31 shows the DNA sequence of the mFab (no hinge) heavy chain of CA185_01979.0.

SEQ ID NO: 32 shows the amino acid sequence of rat TNFα.

SEQ ID NO: 33 shows the amino acid sequence of mouse TNFα.

SEQ ID NO: 34 shows the amino acid sequence of human TNFα.

SEQ ID NO: 35 shows the amino acid sequence of the soluble form of human TNFα.

SEQ ID NO: 36 shows the amino acid sequence of the soluble form of human TNFα, but without the initial "S" (which is a cloning artefact in SEQ ID NO: 35).

SEQ ID NO: 37 shows the amino acid sequence of the extracellular domain of human TNFR1 with N54D and C182S mutations.

SEQ ID NO: 38 shows the amino acid sequence of SEQ ID NO: 37, but without the initial "G", which is a cloning artefact.

DETAILED DESCRIPTION OF THE INVENTION

Modulators of TNF Superfamily Members

Test compounds that bind to trimeric forms of TNF superfamily members have been identified. The following disclosure relates generally to binding of these compounds to any TNF superfamily member. An embodiment of the invention relates specifically to binding of such compounds to TNFα.

The test compounds are small molecular entities (SMEs) that have a molecular weight of 1000 Da or less, 750 Da or less, or 600 Da or less. The molecular weight may be in the range of about 50-about 1000 Da or about 100-about 1000 Da. These compounds stabilise a conformation of the trimeric TNF superfamily member that binds to the requisite TNF superfamily receptor and modulates the signalling of the receptor. Examples of such compounds include compounds of formulae (1)-(7).

The stabilising effect of compounds on trimeric forms of TNF superfamily members may be quantified by measuring the thermal transition midpoint (Tm) of the trimers in the presence and absence of the compound. Tm signifies the temperature at which 50% of the biomolecules are unfolded. Compounds which stabilise TNF superfamily member trimers will increase the Tm of the trimers. Tm may be determined using any appropriate technique known in the art, for example using differential scanning calorimetry (DSC) or fluorescence probed thermal denaturation assays.

The compounds may bind inside the central space present within the TNF superfamily member trimer (i.e. the core of the trimer).

These compounds may turn the TNF superfamily member into a TNF superfamily receptor antagonist. These compounds are therefore capable of blocking the TNF superfamily member signalling without having to compete with the high affinity interaction between the TNF superfamily member and its receptor.

Alternatively, the compounds may stabilise a conformation of the trimeric TNF superfamily member that binds to the requisite TNF superfamily receptor and enhances the signalling of the receptor. These compounds are therefore capable of increasing the TNF superfamily member signalling without having to compete with the high affinity interaction between the TNF superfamily member and its receptor.

Where herein the compounds are described as antagonists, it will be understood that the compounds may equally be agonists and increase signalling by a TNF superfamily receptor that is bound to a complex of a TNF superfamily member trimer and such an agonist compound. Similarly, where other disclosure refers to antagonistic compounds, methods of identifying such compounds and uses of such compounds, this disclosure may refer equally to agonist compounds.

The compounds described herein are allosteric modulators that bind to the natural agonists of the TNF superfamily receptors, i.e. to trimeric forms of TNF superfamily members and drive these trimers to adopt a conformation that still binds to the requisite TNF superfamily receptor and modulates signalling by the receptor. By modulating, it will be understood that the compound may have an antagonistic effect and so decrease signalling by a TNF superfamily receptor, or else a stimulatory effect and so increase or enhance signalling by a TNF superfamily receptor.

These compounds may convert the natural TNF superfamily member agonists into antagonists. In contrast, conventional TNF superfamily member antagonists bind to the TNF superfamily member or the TNF superfamily receptor and prevent the binding of the TNF superfamily member to the requisite receptor. In the alternative, the compounds may increase signalling by a TNF superfamily receptor when the TNF superfamily member is bound compared to the level of signalling by the TNF superfamily receptor when the TNF superfamily member is bound in the absence of the compound. The compounds may therefore convert the natural TNF superfamily member agonists into so-called "superagonists". The compounds may therefore also be known as allosteric modulators of ligand activity (AMLAs).

The compounds are not limited in terms of their chemical formula or structure, provided that they bind to at least one TNF superfamily member and stabilise a conformation of the trimeric TNF superfamily member that binds to the requisite TNF superfamily receptor and modulates the signalling of the TNF superfamily receptor. The compounds can therefore be identified using the antibodies and methods described herein. A non-limiting example is compounds that may comprise a benzimidazole moiety or an isostere thereof.

The compounds may increase the binding affinity of TNF superfamily members (in the form of a compound-trimer complex) to the requisite receptor compared to the binding affinity of the TNF superfamily members to the requisite receptor in the absence of the compounds.

The compounds bind to the trimeric forms of TNF superfamily members. Such compounds may bind specifically (or selectively) to the trimeric forms of one or more TNF superfamily members. A compound may bind specifically (or selectively) to only one of the TNF superfamily members, but not to any other TNF superfamily members. A compound may also bind specifically to two, three, four or up to all of the TNF superfamily members. By specific (or selective), it will be understood that the compounds bind to the molecule or molecules of interest, in this case the trimeric form of the TNF superfamily member, with no significant cross-reactivity to any other molecule, which may include other members of the TNF superfamily. Cross-reactivity may be assessed by any suitable method, for example surface plasmon resonance. Cross-reactivity of a compound for the trimeric form of a TNF superfamily member with a molecule other than the trimeric form of that particular TNF superfamily member may be considered significant if the compound binds to the other molecule at least about 5%, 10%, 15%, 20%, 25%, 30%, 35%, 40%, 45%, 50%, 55%, 60%, 65%, 70%, 75%, 80%, 85%, 90%, 95% or 100% as strongly as it binds to the trimeric form of the TNF superfamily member of interest. For example, cross reactivity may be considered significant if the compound binds to the other molecule about 5%-about 100%, typically about 20%-about 100%, or about 50%-about 100% as strongly as it binds to the trimeric form of the TNF superfamily member of interest. A compound that is specific (or selective) for the trimeric form of a TNF superfamily member may bind to another molecule at less than about 95%, 90%, 85%, 80%, 75%, 70%, 65%, 60%, 55%, 50%, 45%, 40%, 35%, 30%, 25% or 20% the strength that it binds to the trimeric form of the TNF superfamily member (down to zero binding). The compound may bind to the other molecule at less than about 20%, less than about 15%, less than about 10% or less than about 5%, less than about 2% or less than about 1% the strength that it binds to the trimeric form of the TNF superfamily member (down to zero binding).

The rates at which a test compound binds to a TNF superfamily member is referred to herein as the "on" rate" $k_{on-c}$ and the rate at which the test compound dissociates from the TNF superfamily member is referred to herein as the "off" rate or $k_{off-c}$. As used herein, the symbol "$K_{D-c}$" denotes the binding affinity (dissociation constant) of a test compound for a TNF superfamily member. $K_{D-c}$ is defined as $k_{off-c}/k_{on-c}$. Test compounds may have slow "on" rates, which can be measured in minutes by mass spectral analysis of the TNF superfamily member and compound-trimer complex peak intensities. $K_{D-c}$ values for a test compound can be estimated by repeating this measurement at different TNF superfamily member: compound-trimer complex ratios. As a non limiting example, binding of compounds to TNF superfamily trimers can be characterized by fast "on" rates, about $10^7$ $M^{-1}s^{-1}$, with slow "off" rate, for example values of $10^{-3}$ $s^{-1}$, $10^{-4}$ $s^{-1}$, or no measurable "off" rate.

As used herein, the symbol "$k_{on-r}$" denotes the rate (the "on" rate) at which a compound-trimer complex binds to a TNF superfamily receptor. As used herein, the symbol "$k_{off-r}$" denotes the rate (the "off" rate) at which a compound-trimer complex dissociates from a TNF superfamily receptor. As used herein, the symbol "$K_{D-r}$" denotes the binding affinity (dissociation constant) of a compound-trimer complex for a superfamily receptor. $K_{D-r}$ is defined as $k_{off-r}/k_{on-r}$.

The $K_{D-r}$ value of the TNF superfamily member for binding to its receptor in the presence of the test compound (i.e. in the form of a compound-trimer complex) may be at least about 1.5 times, 2 times, 3 times, 4 times, 5 times, 10 times, 20 times, 30 times, 40 times, 50 times, 60 times, 70 times, 80 times, 90 times, 100 times lower than the $K_{D-r}$ value of the TNF superfamily member for binding to its receptor in the absence of the test compound. The $K_{D-r}$ value of the compound-trimer complex for binding to the TNF superfamily member may be decreased at least about 1.5 times, or at least about 3 times, or at least about 4 times the $K_{D-r}$ value of the TNF superfamily trimer binding to the TNF superfamily receptor in the absence of the test compound, i.e. the binding affinity of the compound-trimer complex for the TNF superfamily receptor may be increased at least about 1.5-fold, at least about three-fold, at least about four-fold compared to the binding affinity of the TNF superfamily trimer to the TNF superfamily receptor in the absence of test compound.

A compound described herein may increase the binding affinity of the TNF superfamily member to its receptor by about 2 times, 3 times, 4 times, 5 times, 10 times, 20 times, 30 times, 40 times, 50 times, 60 times, 70 times, 80 times, 90 times, 100 times or more compared to the binding affinity of the TNF superfamily member to its receptor in the absence of the compound.

The binding affinity may be given in terms of binding affinities ($K_{D-r}$) and may be given in any appropriate units, such as μM, nM or pM. The smaller the $K_{D-r}$ value, the larger the binding affinity of the TNF superfamily member to its receptor.

The $K_{D-r}$ value of the TNF superfamily member for binding to its receptor in the presence of the compound may be at least about 1.5 times, 2 times, 3 times, 4 times, 5 times, 10 times, 20 times, 30 times, 40 times, 50 times, 60 times, 70 times, 80 times, 90 times, 100 times lower than the $K_{D-r}$ value of the TNF superfamily member for binding to its receptor in the absence of the test compound.

The decrease in the $K_{D-r}$ value of the compound-trimer complex for binding to the TNF superfamily receptor compared to the $K_{D-r}$ value of the TNF superfamily trimer alone binding to the TNF superfamily receptor may result from an increase in the on rate ($k_{on-r}$) of the compound-trimer complex binding to the TNF superfamily receptor compared to the TNF superfamily trimer alone, and/or a decrease in the off rate ($k_{off-r}$) compared to the TNF superfamily trimer alone. The on rate ($k_{on-r}$) of the compound-trimer complex binding to the TNF superfamily receptor is generally increased compared to the TNF superfamily trimer alone. The off rate ($k_{off-r}$) of the compound-trimer complex binding to the TNF superfamily receptor is generally decreased compared to the TNF superfamily trimer alone. Most suitably, the on rate ($k_{on-r}$) of the compound-trimer complex binding to the TNF superfamily receptor is increased, and the off-rate ($k_{off-r}$) of the compound-trimer complex binding to the TNF superfamily receptor is decreased, compared to the TNF superfamily trimer alone. The $k_{on-r}$ value of the compound-trimer complex to the requisite TNF superfamily receptor may be increased by at least about 1.5-fold or at least about two or at least about three fold compared to the $k_{on-r}$ value of the TNF superfamily trimer binding to its receptor in the absence of the compound and/or the $k_{off-r}$ value of the compound-trimer complex to the requisite TNF superfamily receptor may be decreased by at least about 1.2-fold, at least about 1.6-fold, at least about two-fold, more suitably at least about 2.4-fold compared to the $k_{off-r}$ value of the TNF superfamily trimer binding to its receptor in the absence of the compound.

The on-rate for compound binding to TNF superfamily trimer ($k_{on-c}$) is typically faster than the on-rate for compound-trimer complex binding to TNF superfamily receptor ($k_{on-r}$). The off-rate for compound-trimer complex binding to TNF superfamily receptor ($k_{off-r}$) is also typically faster than the off-rate for compound binding to TNF superfamily trimer ($k_{off-c}$). In an embodiment of the invention, the on-rate for compound binding to TNF superfamily trimer ($k_{on-c}$) is faster than the on-rate for compound-trimer complex binding to TNF superfamily receptor ($k_{on-r}$), and the off-rate for compound-trimer complex binding to TNF superfamily receptor ($k_{off-r}$) is faster than the off-rate for compound binding to TNF superfamily trimer ($k_{off-c}$). The $K_{D-c}$ value of the compound for binding to TNF superfamily trimer is generally lower than the $K_{D-r}$ value of the compound-trimer complex for binding to TNF superfamily receptor, i.e. the compound has a higher affinity for the trimer than the compound-trimer complex has for the receptor.

The $k_{on-r}$, $k_{off-r}$, and $K_{D-r}$ values for both the compound-trimer complex and the TNF superfamily trimer to the requisite TNF superfamily receptor may be determined using any appropriate technique, for example surface plasmon resonance, mass spectrometry and isothermal calorimetry. The $K_{D-r}$ value of the TNF superfamily member for binding to its receptor in the presence of the test compound may be 1 µM, 100 nM, 10 nM, 5 nM, 1 nM, 100 pM, 10 pM or less (down to a lower value of about 1 pM). The $K_{D-r}$ value of the TNF superfamily member for binding to its receptor in the presence of the test compound (i.e. in a compound-trimer complex) may be 1 nM or less. The $K_{D-r}$ value of a compound-trimer complex for binding to the requisite TNF superfamily receptor may be less than 600 pM, less than 500 pM, less than 400 pM, less than 300 pM, less than 200 pM, less than 100 pM or less than 50 pM (again down to a lower value of about 1 pM). The $K_{D-r}$ value of a compound-trimer complex for binding to the requisite TNF superfamily receptor may be less than about 200 pM (to about 1 pM).

Compounds may be identified by an assay which comprises determining the $K_{D-r}$ of the trimeric form of the TNF superfamily member in a sample of the TNF superfamily member and the compound; comparing the $K_{D-r}$ of the trimeric form of the TNF superfamily member in the sample with a control sample; and selecting a compound. A control may be a positive control, which is known to increase the binding affinity of the TNF superfamily member to its receptor. Here, the test compound may have a $K_{D-r}$ equal to or less than (better than) the positive control.

The compounds stabilise the trimeric form of the TNF superfamily member. Stabilisation is considered to occur if a test compound increases the proportion of trimer compared to the amount of trimer observed for a sample containing the TNF superfamily member and the destabilising agent in the absence of the test compound. The test compound may increase the amount of trimer by about 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400% or more compared to the amount of trimer present in a sample containing the TNF superfamily member and the destabilising agent in the absence of the test compound.

The test compound may also increase the amount of trimer compared to that observed for a sample of the TNF superfamily member in the absence of both the destabilising agent and the test compound. The test compound may increase the amount of trimer by about 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400% or more compared to the amount of trimer present in a sample containing the TNF superfamily member in the absence of both the destabilising agent and the test compound.

The test compound may increase the amount of the TNF superfamily member bound to its receptor by about 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400% or more compared to the amount of the TNF superfamily member bound to its receptor in a sample containing the TNF superfamily member in the absence of the test compound.

The test compounds may enhance the stability of the trimeric form of the TNF superfamily member. Enhanced stability of the trimeric form of the TNF superfamily member is considered to occur if a test compound increases the thermal transition midpoint ($T_m$) of the trimeric form of the TNF superfamily member compared to the $T_m$ of the trimeric form of the TNF superfamily member observed for a sample containing the TNF superfamily member and the destabilising agent in the absence of the test compound. The $T_m$ of the trimeric form of the TNF superfamily member is the temperature at which 50% of the biomolecules are unfolded. The $T_m$ of the trimeric form of the TNF superfamily member in the presence and/or absence of the test compound may be measured using any appropriate technique known in the art, for example using differential scanning calorimetry (DSC) or fluorescence probed thermal denaturation assays.

The test compound may increase the $T_m$ of the trimeric form of the TNF superfamily member by at least 1° C., at least 2° C., at least 5° C., at least 10° C., at least 15° C., at least 20° C. or more compared to the $T_m$ of the trimeric form of the TNF superfamily member in a sample containing the TNF superfamily member in the absence of the test compound. The test compound may increase the $T_m$ of the trimeric form of the TNF superfamily member by at least 1° C., by at least 10° C. and by between 10° C. and 20° C.

The compounds may completely or partially inhibit signalling through a TNF receptor when a TNF superfamily member in the form of a compound-trimer complex binds to the receptor. The compound may act to reduce signalling through a TNF superfamily receptor by at least about 10%, 20%, 30%, 40%, 50%, 60%, 70%, 80%, 90% or 100%. Alternatively, the compounds may increase signalling through a TNF receptor when a TNF superfamily member in the form of a compound-trimer complex binds to the receptor. The compound may act to increase signalling through a TNF superfamily receptor by at least about 10%, 20%, 30%, 40%, 50%, 60%, 70%, 80%, 90%, 100% or 200%. Any change in the level of signalling may be measured by any appropriate technique, including but not limited to measuring reporter gene activity by alkaline phosphatase or luciferase, NF-κB translocation using machines such as the Cellomics Arrayscan, phosphorylation of downstream effectors, recruitment of signalling molecules, or cell death.

The compounds may modulate at least one of the downstream effects of signalling through a TNF receptor when a TNF superfamily member in the form of a compound-trimer complex binds to the receptor. Such effects are discussed herein and include TNF superfamily-induced IL-8, IL17A/F, IL2 and VCAM production, TNF superfamily-induced NF-κB activation and neutrophil recruitment. Standard techniques are known in the art for measuring the downstream effects of TNF superfamily members. The compounds may modulate at least 1, 2, 3, 4, 5, 10 or up to all of the downstream effects of signalling through a TNF receptor.

The activity of the compounds may be quantified using standard terminology, such as $IC_{50}$ or half maximal effective concentration ($EC_{50}$) values. $IC_{50}$ values represent the concentration of a compound that is required for 50% inhibition of a specified biological or biochemical function. $EC_{50}$ values represent the concentration of a compound that is required for 50% of its maximal effect. The compounds may have $IC_{50}$ or $EC_{50}$ values of 500 nM, 400 nM, 300 nM, 200 nM, 100 nM, 90 nM, 80 nM, 70 nM, 60 nM, 50 nM, 40 nM, 30 nM, 20 nM, 10 nM, 5 nM, 1 nM, 100 pM or less (down to a lower value of about 10 pM or 1 pM). $IC_{50}$ and $EC_{50}$ values may be measured using any appropriate technique, for example cytokine production can be quantified using ELISA. $IC_{50}$ and $EC_{50}$ values can then be generated using a standard 4-parameter logistic model also known as the sigmoidal dose response model.

As mentioned above, examples of compounds which are capable of binding to TNF and modulating signalling are compounds of formulae (1)-(7).

Modulator-TNF Superfamily Member Complexes

An embodiment of the present invention identified that binding of the compounds described herein to trimeric forms of TNF superfamily members results in a conformational change in the TNF superfamily trimer. In a further embodiment, the TNF superfamily member trimer takes on a deformed or distorted conformation when bound by a compound as disclosed herein.

For example, when compounds (1)-(7) are bound the soluble domain of human TNFα the TNF retains its trimeric structure but the A and C subunits move away from each other and C rotates to generate a cleft between these subunits.

Without being bound by theory, it is believed that, in the absence of a compound, trimeric TNF superfamily members, including trimeric TNFα, are capable of binding to three separate dimeric TNF superfamily member receptors. Each of the dimeric TNF superfamily member receptors is capable of binding to two separate TNF superfamily trimers. This results in the aggregation of multiple TNF superfamily member trimers and TNF superfamily member receptor dimers, creating signalling rafts that initiate downstream signalling.

When trimeric TNFα is bound to the compound, the conformation of the resulting complex is deformed. Accordingly, without being bound by theory, it is believed that, in the presence of a compound as disclosed herein, trimeric TNF superfamily members, including trimeric TNFα, are only capable of binding to two separate dimeric TNF superfamily member receptors. The fact that only two, rather than three, separate dimeric TNF superfamily member receptors bind to the trimeric TNF superfamily member reduces or inhibiting the aggregation of multiple TNF superfamily member trimers and TNF superfamily member receptor dimers. This reduces or inhibits the formation of signalling rafts and so reduces or inhibits downstream signalling.

The antibodies of the invention may be used to detect TNFα with a distorted conformation as a result of the binding of a compound as disclosed herein. Typically the TNFα with a distorted or deformed conformation is trimeric TNFα. However, antibodies of the invention may also bind to other forms of the TNFα. For example, antibodies of the invention may bind to TNFα monomers.

The TNFα is typically trimeric TNFα and may be $TNFα_s$ (or trimeric $TNFα_s$).

Accordingly, the invention provides a complex comprising a TNFα trimer and a compound that is bound thereto, whereby the compound-trimer complex binds to the requisite TNFα receptor and modulates the signalling induced by the trimer through the receptor, wherein said complex binds to an antibody of the invention with an affinity of at least 1 nM (i.e. 1 nM or less, down to about 1 pM). The TNF superfamily member is typically $TNFα_s$.

Furthermore, the antibody generally binds to the complex with an affinity that is at least about 100 times lower (the affinity is improved at least about 100 times), about 200 times lower, relative to the affinity for binding to the compound in the absence of the TNFα timer and/or for binding to the TNFα trimer in the absence of compound.

The present invention further provides a compound that is capable of binding to a TNFα trimer to form a complex, whereby the compound-trimer complex binds to the requisite TNFα receptor and modulates the signalling induced by the trimer through the receptor, wherein the compound-trimer complex binds to an antibody of the invention with a $K_{D-ab}$ of 1 nM or less (down to about 1 pM). The TNFα is typically $TNF\alpha_s$.

The antibody may bind to the complex with an affinity that is at least about 100 times lower (the affinity is improved at least about 100 times), about 200 times lower, relative to the affinity for binding to the compound in the absence of the TNFα timer and/or for binding to the TNFα trimer in the absence of compound.

The compound-trimer complex may bind to any antibody of the invention.

A compound or complex described herein may be used in the treatment and/or prophylaxis of a pathological condition. Accordingly, provided is a compound or complex of the invention for use in a method of therapy practiced on the human or animal body. The invention also provides a method of therapy comprising the administration of a compound or complex of the invention to a subject. The compound or complex of the invention may be used in any therapeutic indication and/or pharmaceutical composition described herein.

Antibodies

The invention provides antibodies that selectively bind to at least one compound-trimer complex comprising at least one compound disclosed herein and a TNFα trimer.

Typically, selective binding of an antibody of the invention to a compound-(trimer) complex is measured relative to the binding of the antibody to the compound in the absence of the TNFα, or to the TNFα in the absence of the compound or to other (different) compound-(trimer) complexes.

The compound may be any compound described herein, including compounds (1)-(7) (or salts or solvates thereof). A TNF superfamily member is TNFα. Tithe TNFα may be human TNFα, particularly soluble TNFα ($TNF\alpha_s$). The $TNF\alpha_s$ may have the sequence of SEQ ID NO: 35 or SEQ ID NO: 36 (which lacks the N-terminal "S" from SEQ ID NO:35) or may be a variant thereof. Such variants typically retain at least about 60%, 70%, 80%, 90%, 91%, 92%, 93%, 94% or 95% identity to SEQ ID NO:35 or SEQ ID NO:36 (or even about 96%, 97%, 98% or 99% identity). In other words, such variants may retain about 60%-about 99% identity to SEQ ID NO:35 or SEQ ID NO:36, about 80%-about 99% identity to SEQ ID NO:35 or SEQ ID NO:36, about 90%-about 99% identity to SEQ ID NO:35 or SEQ ID NO:36 and about 95%-about 99% identity to SEQ ID NO:35 or SEQ ID NO:36. Variants are described further below.

Antibodies of the invention may also bind to other forms of TNFα. To illustrate, the Examples of the present application demonstrate that the CA185_0179 antibody binds to trimeric TNFα. However, as shown in FIG. 1 (crystal structure of the CA185_0179 antibody bound to a TNFα monomer in the presence of compound (1)) the antibody also appears to bind to monomeric TNFα. Without being bound by theory, in the presence of the compound it is believed that the soluble domain of the TNF retains its trimeric structure. However, the A and C subunits move away from each other (and the C subunit rotates) to generate a cleft between these two subunits. Thus although antibodies of the invention bind to distorted trimers, it is also possible that the antibodies can still bind if the trimeric structure is forced apart into monomers. (See below for further discussion of the "A" and "C" subunits.)

The term "antibody" as referred to herein includes whole antibodies and any antigen binding fragment (i.e., "antigen-binding portion") or single chains thereof. An antibody refers to a glycoprotein comprising at least two heavy (H) chains and two light (L) chains inter-connected by disulfide bonds, or an antigen-binding portion thereof. Each heavy chain is comprised of a heavy chain variable region (abbreviated herein as HCVR or $V_H$) and a heavy chain constant region. Each light chain is comprised of a light chain variable region (abbreviated herein as LCVR or $V_L$) and a light chain constant region. The variable regions of the heavy and light chains contain a binding domain that interacts with an antigen. The $V_H$ and $V_L$ regions can be further subdivided into regions of hypervariability, termed complementarity determining regions (CDR), interspersed with regions that are more conserved, termed framework regions (FR).

The constant regions of the antibodies may mediate the binding of the immunoglobulin to host tissues or factors, including various cells of the immune system (e.g., effector cells) and the first component (Clq) of the classical complement system.

An antibody of the invention may be a monoclonal antibody or a polyclonal antibody, and will typically be a monoclonal antibody. An antibody of the invention may be a chimeric antibody, a CDR-grafted antibody, a nanobody, a human or humanised antibody or an antigen-binding portion of any thereof. For the production of both monoclonal and polyclonal antibodies, the experimental animal is typically a non-human mammal such as a goat, rabbit, rat or mouse but the antibody may also be raised in other species.

Polyclonal antibodies may be produced by routine methods such as immunisation of a suitable animal, with the antigen of interest. Blood may be subsequently removed from the animal and the IgG fraction purified.

Antibodies generated against compound-trimer complexes of the invention may be obtained, where immunisation of an animal is necessary, by administering the polypeptides to an animal, e.g. a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies of the invention may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15): 7843-78481; WO92/02551; WO2004/051268 and WO2004/106377.

The antibodies of the present invention can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

Fully human antibodies are those antibodies in which the variable regions and the constant regions (where present) of both the heavy and the light chains are all of human origin, or substantially identical to sequences of human origin, but not necessarily from the same antibody. Examples of fully human antibodies may include antibodies produced, for example by the phage display methods described above and antibodies produced by mice in which the murine immunoglobulin variable and optionally the constant region genes have been replaced by their human counterparts e.g. as described in general terms in EP 0546073, U.S. Pat. Nos. 5,545,806, 5,569,825, 5,625,126, 5,633,425, 5,661,016, 5,770,429, EP 0438474 and EP 0463151.

Alternatively, an antibody according to the invention may be produced by a method comprising: immunising a non-human mammal with an immunogen comprising a compound-trimer complex of a trimeric TNFα and a compound disclosed herein; obtaining an antibody preparation from said mammal; deriving therefrom monoclonal antibodies that selectively recognise said complex and screening the population of monoclonal antibodies for monoclonal antibodies that bind to TNFα only in the presence of the compound.

The antibody molecules of the present invention may comprise a complete antibody molecule having full length heavy and light chains or a fragment or antigen-binding portion thereof. The term "antigen-binding portion" of an antibody refers to one or more fragments of an antibody that retain the ability to selectively bind to an antigen. It has been shown that the antigen-binding function of an antibody can be performed by fragments of a full-length antibody. The antibodies and fragments and antigen binding portions thereof may be, but are not limited to Fab, modified Fab, Fab', modified Fab', F(ab')2, Fv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9): 1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO 2005/003169, WO 2005/003170 and WO 2005/003171 and Fab-dAb fragments described in International patent application WO2009/040562. Multi-valent antibodies may comprise multiple specificities or may be monospecific (see for example WO 92/22853 and WO 05/113605). These antibody fragments may be obtained using conventional techniques known to those of skill in the art, and the fragments may be screened for utility in the same manner as intact antibodies.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required.

An antibody of the invention may be prepared, expressed, created or isolated by recombinant means, such as (a) antibodies isolated from an animal (e.g., a mouse) that is transgenic or transchromosomal for the immunoglobulin genes of interest or a hybridoma prepared therefrom, (b) antibodies isolated from a host cell transformed to express the antibody of interest, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

An antibody of the invention may be a human antibody or a humanised antibody. The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

Such a human antibody may be a human monoclonal antibody. Such a human monoclonal antibody may be produced by a hybridoma that includes a B cell obtained from a transgenic nonhuman animal, e.g., a transgenic mouse, having a genome comprising a human heavy chain transgene and a light chain transgene fused to an immortalized cell.

Human antibodies may be prepared by in vitro immunisation of human lymphocytes followed by transformation of the lymphocytes with Epstein-Barr virus.

The term "human antibody derivatives" refers to any modified form of the human antibody, e.g., a conjugate of the antibody and another agent or antibody.

The term "humanized antibody" is intended to refer to CDR-grafted antibody molecules in which CDR sequences derived from the germline of another mammalian species, such as a mouse, have been grafted onto human framework sequences. Additional framework region modifications may be made within the human framework sequences.

As used herein, the term 'CDR-grafted antibody molecule' refers to an antibody molecule wherein the heavy and/or light chain contains one or more CDRs (including, if desired, one or more modified CDRs) from a donor antibody (e.g. a murine or rat monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Suitably, the CDR-grafted antibody according to the present invention has a variable domain comprising human acceptor framework regions as well as one or more of the CDRs or specificity determining residues described above. Thus, provided in one embodiment is a neutralising CDR-grafted antibody wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available for example at: http://www.vbase2.org/ (see Retter et al, Nucl. Acids Res. (2005) 33 (supplement 1), D671-D674).

In a CDR-grafted antibody of the present invention, the acceptor heavy and light chains do not necessarily need to be derived from the same antibody and may, if desired, comprise composite chains having framework regions derived from different chains.

Also, in a CDR-grafted antibody of the present invention, the framework regions need not have exactly the same sequence as those of the acceptor antibody. For instance, unusual residues may be changed to more frequently occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705: 129-134, 1995).

In one embodiment the antibody heavy chain comprises a CH1 domain and the antibody light chain comprises a CL domain, either kappa or lambda.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or surface carries no net electrical charge. In one embodiment the antibody or fragment according to the present disclosure has an isoelectric point (pI) of at least 7. In one embodiment the antibody or fragment has an isoelectric point of at least 8, such as 8.5, 8.6, 8.7, 8.8 or 9. In one embodiment the pI of the antibody is 8. Programs such as ** ExPASY http://www.expasy.ch/tools/pi_tool.html (see Walker, The Proteomics Protocols Handbook, Humana Press (2005), 571-607) may be used to predict the isoelectric point of the antibody or fragment.

Antibodies which bind to the epitope disclosed herein may comprise at least one, at least two or all three heavy chain CDR sequences of SEQ ID NOS: 4 to 6 (HCDR1/HCDR2/HCDR3 respectively). These are the HCDR1/HCDR2/HCDR3 sequences of the CA185_01974 antibody of the Examples. In some instances, the antibody does not comprise CDRs of SEQ ID NOS: 4 to 6 (i.e. the antibody does not comprise CDRs of any one of, or all of, SEQ ID NOs: 4-6).

Furthermore, such antibodies may comprise at least one, at least two or all three light chain CDR sequences of SEQ ID NOS: 1 to 3 (LCDR1/LCDR2/LCDR3 respectively). These are the LCDR1/LCDR2/LCDR3 sequences of the CA185_01974 antibody of the Examples. In some instances, the antibody does not comprise CDRs of SEQ ID NOs: 1 to 3 (i.e. the antibody does not comprise CDRs of any one of, or all of, SEQ ID NOs: 1 to 3).

The antibody comprises at least a HCDR3 sequence of SEQ ID NO: 6. In one embodiment, the antibody comprises at least one heavy chain CDR sequence selected from SEQ ID NOS: 4 to 6 and at least one light chain CDR sequence selected from SEQ ID NOS 1 to 3. The antibody may comprise at least two heavy chain CDR sequences selected from SEQ ID NOS: 4 to 6 and at least two light chain CDR sequences selected from SEQ ID NOS: 1 to 3. The antibody comprises all three heavy chain CDR sequences of SEQ ID NOS: 4 to 6 (HCDR1/HCDR2/HCDR3 respectively) and all three light chain CDR sequences SEQ ID NOS: 1 to 3 (LCDR1/LCDR2/LCDR3 respectively). The antibodies may be chimeric, human or humanised antibodies. In some instances, the antibody does not comprise CDRs of any one of, or all of, SEQ ID NOs: 1 to 6.

The antibody may also comprise at least one, at least two or all three heavy chain CDR sequences of SEQ ID NOS: 19 to 21 (HCDR1/HCDR2/HCDR3 respectively). These are the HCDR1/HCDR2/HCDR3 sequences of the CA185_01979 antibody of the Examples. In some instances, the antibody does not comprise CDRs of SEQ ID NOs: 19 to 21 (i.e. CDRs of any one of, or all of, SEQ ID NOs: 19-21).

The antibody comprises a HCDR3 sequence of SEQ ID NO: 21.

The antibody may also comprise at least one, at least two or all three light chain CDR sequences of SEQ ID NOS: 1, 17, 18 (LCDR1/LCDR2/LCDR3 respectively). These are the LCDR1/LCDR2/LCDR3 sequences of the CA185_01979 antibody of the Examples. In some instances, the antibody does not comprise CDRs of SEQ ID NOs: 1, 17 or 18 (i.e. CDRs of any one of, or all of, SEQ ID NOs: 1, 17 or 18.)

In one embodiment of the invention, the antibody comprises at least one heavy chain CDR sequence selected from SEQ ID NOS: 19 to 21 and at least one light chain CDR sequence selected from SEQ ID NOS: 1, 17, 18. The antibody may comprise at least two heavy chain CDR sequences selected from SEQ ID NOS: 19 to 21 and at least two light chain CDR sequences selected from SEQ ID NOS: 1, 17, 18. The antibody may comprise all three heavy chain CDR sequences of SEQ ID NOS: 19 to 21 (HCDR1/HCDR2/HCDR3 respectively) and all three light chain CDR sequences SEQ ID NOS: 1, 17, 18 (LCDR1/LCDR2/LCDR3 respectively). The antibodies may be chimeric, human or humanised antibodies. In some instances, the antibody does not comprise CDRs of any one of, or all of, SEQ ID NOs: 1, 17, 18, 19, 20 or 21.

The antibody may comprise any combination of CDR sequences of the CA185_01974 antibody and the CA185_01979 antibody. In particular, the antibody may comprise least one HCDR sequence selected from SEQ ID NOs: 4-6 and 19-21 and/or at least one LCDR sequence selected from SEQ ID NOs: 1-3, 17 and 18.

The antibody may comprise:
a HCDR1 selected from SEQ ID NOs: 4 and 19; and/or
a HCDR2 selected from SEQ ID NOs: 5 and 20; and/or
a HCDR3 selected from SEQ ID NOs: 6 and 21; and/or
a LCDR1 of SEQ ID NO: 1; and/or
a LCDR2 selected from SEQ ID NOs: 2 and 17; and/or
a LCDR3 selected from SEQ ID NOs: 3 and 18.

In some instances, the antibody does not comprise CDRs of any one of the following sequences: SEQ ID NOs: 1 to 6 and 17-21.

The antibody may comprise a heavy chain variable region (HCVR) sequence of SEQ ID NO: 8 (the HCVR of CA185_01974). The antibody may comprise a light chain variable region (LCVR) sequence of SEQ ID NO: 7 (the LCVR of CA185_01974). The antibody suitably comprises the heavy chain variable region sequence of SEQ ID NO: 8 and the light chain variable region sequence of SEQ ID NO: 7.

In some instances, the antibody does not comprise a HCVR of SEQ ID NO: 8 and/or an LCVR of SEQ ID NO: 7.

The antibody may also comprise a heavy chain variable region (HCVR) sequence of SEQ ID NO: 23 (the HCVR of CA185_01979). The antibody may comprise a light chain variable region (LCVR) sequence of SEQ ID NO: 22 (the LCVR of CA185_01979). The antibody suitably comprises the heavy chain variable region sequence of SEQ ID NO: 23 and the light chain variable region sequence of SEQ ID NO: 22. In some instances, the antibody does not comprise a HCVR of SEQ ID NO: 23 and/or an LCVR of SEQ ID NO: 22.

The antibody may comprise a combination of heavy and light chain variable regions from the CA185_01974 and CA185_01979 antibodies. In other words, the antibody may comprise a heavy chain variable region of SEQ ID NO: 8 or 23 and/or a light chain variable region of SEQ ID NO: 7 or 22.

In some instances, the antibody does not comprise a heavy chain variable region of SEQ ID NO: 8 or 23 and/or a light chain variable region of SEQ ID NO: 7 or 22.

The antibody may comprise a heavy chain (H-chain) sequence of SEQ ID NO: 12 (CA185_01974 mIgG1) or 13 (CA185_01974 mFab (no hinge)). The antibody may comprise a light chain (L-chain) sequence of SEQ ID NO: 11 (CA185_01974 kappa light chain). The antibody may comprise the heavy chain sequence of SEQ ID NO: 12/13 and the light chain sequence of SEQ ID NO: 11. The antibodies may be chimeric, human or humanised antibodies. In some instances, the antibody does not comprise heavy and/or light chains of these sequences.

The antibody may comprise a heavy chain sequence of SEQ ID NO: 27 (CA185_01979 mIgG1) or 28 (CA185_01979 mFab (no hinge)). The antibody may comprise a light chain sequence of SEQ ID NO: 26 (CA185_01979 kappa light chain). The antibody comprises the heavy chain sequence of SEQ ID NO: 27/28 and the light chain sequence of SEQ ID NO: 26. The antibodies may be chimeric, human or humanised antibodies. Again, sequences from CA185_01974 and CA185_01979 may be combined. In some instances, the antibody does not comprise heavy and/or light chains of these sequences.

The antibody may alternatively be or may comprise a variant of one of the specific sequences recited above. For example, a variant may be a substitution, deletion or addition variant of any of the above amino acid sequences.

A variant antibody may comprise 1, 2, 3, 4, 5, up to 10, up to 20 or more (typically up to a maximum of 50) amino acid substitutions and/or deletions from the specific sequences discussed above. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Substitution" variants typically involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

"Derivatives" or "variants" generally include those in which instead of the naturally occurring amino acid the amino acid which appears in the sequence is a structural analog thereof. Amino acids used in the sequences may also be derivatized or modified, e.g. labelled, providing the function of the antibody is not significantly adversely affected.

Derivatives and variants as described above may be prepared during synthesis of the antibody or by post-production modification, or when the antibody is in recombinant form using the known techniques of site-directed mutagenesis, random mutagenesis, or enzymatic cleavage and/or ligation of nucleic acids.

Variant antibodies may have an amino acid sequence which has more than about 60%, or more than about 70%, e.g. 75 or 80%, more than about 85%, e.g. more than about 90 or 95% amino acid identity to the amino acid sequences disclosed herein (particularly the HCVR/LCVR sequences and the H- and L-chain sequences). Furthermore, the antibody may be a variant which has more than about 60%, or more than about 70%, e.g. 75 or 80%, more than about 85%, e.g. more than about 90 or 95% amino acid identity to the HCVR/LCVR sequences and the H- and L-chain sequences disclosed herein, whilst retaining the exact CDRs disclosed for these sequences. Variants may retain at least about 90%, 91%, 92%, 93%, 94%, 95%, 96%, 97%, 98% or 99% identity to the HCVR/LCVR sequences and to the H- and L-chain sequences disclosed herein (in some circumstances whilst retaining the exact CDRs). In some instances, the antibody is not a variant with more than 60, 70, 75, 80, 85, 90 or 95% identity to any of the sequences described herein (i.e. the antibody does not have 60, 70, 75, 80, 85, 90 or 95% identity to the HCVR and/or LCVR sequences, or the H- and/or L-chain sequences described herein).

Variants retain about 60%-about 99% identity, about 80%-about 99% identity, about 90%-about 99% identity or about 95%-about 99% identity. This level of amino acid identity may be seen across the full length of the relevant SEQ ID NO sequence or over a part of the sequence, such as across about 20, 30, 50, 75, 100, 150, 200 or more amino acids, depending on the size of the full length polypeptide.

In connection with amino acid sequences, "sequence identity" refers to sequences which have the stated value when assessed using ClustalW (Thompson et al., 1994, supra) with the following parameters:

Pairwise alignment parameters—Method: accurate, Matrix: PAM, Gap open penalty: 10.00, Gap extension penalty: 0.10;

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatized.

Antibodies having specific sequences and variants which maintain the function or activity of these chains are therefore provided.

The present invention also provides an isolated DNA sequence encoding the heavy and/or light chain variable regions(s) of an antibody molecule of the present invention.

An isolated DNA sequence of SEQ ID NO: 10 encodes the heavy chain variable region of SEQ ID NO: 8. An isolated DNA sequence of SEQ ID NO: 9 encodes the light chain variable region of SEQ ID NO: 7.

An isolated DNA sequence of SEQ ID NO: 25 encodes the heavy chain variable region of SEQ ID NO: 23. An isolated DNA sequence of SEQ ID NO: 24 encodes the light chain variable region of SEQ ID NO: 22.

The present invention also provides an isolated DNA sequence encoding the heavy and/or light chain(s) of any antibody molecule of the present invention. Suitably, the DNA sequence encodes the heavy or the light chain of an antibody molecule of the present invention.

The isolated DNA sequences of SEQ ID NOs: 15 or 16 encode the heavy chains of SEQ ID NOs: 12 and 13 respectively. The isolated DNA sequence of SEQ ID NO: 14 encodes the light chain of SEQ ID NO: 11.

The isolated DNA sequences of SEQ ID NOs: 30 or 31 encode the heavy chains of SEQ ID NOs: 27 and 28 respectively. The isolated DNA sequence of SEQ ID NO: 29 encodes the light chain of SEQ ID NO: 26.

A suitable polynucleotide sequence may alternatively be a variant of one of these specific polynucleotide sequences. For example, a variant may be a substitution, deletion or addition variant of any of the above nucleic acid sequences. A variant polynucleotide may comprise 1, 2, 3, 4, 5, up to 10, up to 20, up to 30, up to 40, up to 50, up to 75 or more nucleic acid substitutions and/or deletions from the sequences given in the sequence listing. Generally, a variant has 1-20, 1-50, 1-75 or 1-100 substitutions and/or deletions.

Suitable variants may be at least about 70% homologous to a polynucleotide of any one of nucleic acid sequences disclosed herein, typically at least about 80 or 90% and at least about 95%, 97% or 99% homologous thereto. Variants may retain at least about 90%, 91%, 92%, 93%, 94%, 95%, 96%, 97%, 98% or 99% identity. Variants retain about 60%-about 99% identity, about 80%-about 99% identity, about 90%-about 99% identity or about 95%-about 99% identity. Homology and identity at these levels is generally present at least with respect to the coding regions of the polynucleotides. Methods of measuring homology are well known in the art and it will be understood by those of skill in the art that in the present context, homology is calculated on the basis of nucleic acid identity. Such homology may exist over a region of at least about 15, at least about 30, for instance at least about 40, 60, 100, 200 or more contiguous nucleotides (depending on the length). Such homology may exist over the entire length of the unmodified polynucleotide sequence.

Methods of measuring polynucleotide homology or identity are known in the art. For example the UWGCG Package provides the BESTFIT program which can be used to calculate homology (e.g. used on its default settings) (Devereux et al (1984) Nucleic Acids Research 12, p 387-395).

The PILEUP and BLAST algorithms can also be used to calculate homology or line up sequences (typically on their default settings), for example as described in Altschul S. F. (1993) J Mol Evol 36:290-300; Altschul, S, F et al (1990) J Mol Biol 215:403-10.

Software for performing BLAST analysis is publicly available through the National Centre for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89:10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90:5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, typically less than about 0.1, suitably less than about 0.01, and most suitably less than about 0.001. For example, the smallest sum probability may be in the range of about 1-about 0.001, often about 0.01-about 0.001.

The homologue may differ from a sequence in the relevant polynucleotide by less than about 3, 5, 10, 15, 20 or more mutations (each of which may be a substitution, deletion or insertion). For example, the homologue may differ by 3-50 mutations, often 3-20 mutations. These mutations may be measured over a region of at least 30, for instance at least about 40, 60 or 100 or more contiguous nucleotides of the homologue.

In one embodiment, a variant sequence may vary from the specific sequences given in the sequence listing by virtue of the redundancy in the genetic code. The DNA code has 4 primary nucleic acid residues (A, T, C and G) and uses these to "spell" three letter codons which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. A variant polynucleotide of the invention may therefore encode the same polypeptide sequence as another polynucleotide of the invention, but may have a different nucleic acid sequence due to the use of different codons to encode the same amino acids.

The DNA sequence of the present invention may comprise synthetic DNA, for instance produced by chemical processing, cDNA, genomic DNA or any combination thereof.

DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example *E. coli*, and other microbial systems may be used or eukaryotic, for example mammalian, host cell expression systems may also be used. Suitable mammalian host cells include CHO, myeloma or hybridoma cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

Screening methods as described herein may be used to identify suitable antibodies that are capable of binding to a compound-trimer complex. Thus, the screening methods described herein may be carried out to test antibodies of interest.

Antibodies of the invention can be tested for binding to a compound-trimer complex by, for example, standard ELISA or Western blotting. An ELISA assay can also be used to screen for hybridomas that show positive reactivity with the target protein. The binding selectivity of an antibody may also be determined by monitoring binding of the antibody to cells expressing the target protein, for example by flow cytometry. Thus, a screening method of the invention may comprise the step of identifying an antibody that is capable of binding a compound-trimer complex by carrying out an ELISA or Western blot or by flow cytometry.

Antibodies of the invention selectively (or specifically) recognise a TNFα trimer-compound complex, i.e. an epitope within the compound-trimer complex. An antibody, or other compound, "selectively binds" or "selectively recognises" a protein when it binds with preferential or high affinity to the protein for which it is selective but does not substantially bind, or binds with low affinity, to other proteins. The selectivity of an antibody of the invention for a target a compound-trimer complex may be further studied by determining whether or not the antibody binds to other related compound-trimer complexes as discussed above or whether it discriminates between them.

An antibody may bind specifically (or selectively) to compound-trimer complexes comprising other trimeric forms of one or more TNF superfamily members. For example, an antibody may bind to compound-trimer complexes comprising TNFα, compound-trimer complexes comprising TNFβ and compound-trimer complexes comprising CD40L. Alternatively, an antibody may bind specifically (or selectively) to compound-trimer complexes comprising only TNFα, but not to compound-trimer complexes comprising any other TNF superfamily members. For example, an antibody may bind to compound-trimer complexes comprising TNFα, but not to compound-trimer complexes comprising TNFβ or compound-trimer complexes comprising CD40L. An antibody may bind specifically (or selectively) to compound-trimer complexes comprising up to two, three, four or up to all of the TNF superfamily members.

By specific (or selective), it will be understood that the antibody binds to the compound-trimer complexes of interest with no significant cross-reactivity to any other molecule, which may include test compounds in the absence of a TNF superfamily trimer or TNF superfamily member trimers in the absence of a test compound. Cross-reactivity may be assessed by any suitable method described herein. Cross-reactivity of an antibody for a compound-trimer complex with a molecule other than the compound-trimer complex may be considered significant if the antibody binds to the other molecule at least about 5%, 10%, 15%, 20%, 25%, 30%, 35%, 40%, 45%, 50%, 55%, 60%, 65%, 70%, 75%, 80%, 85%, 90% 95% or 100% as strongly as it binds to the compound-trimer complex of interest. An antibody that is specific (or selective) for the compound-trimer complex may bind to another molecule at less than about 90%, 85%, 80%, 75%, 70%, 65%, 60%, 55%, 50%, 45%, 40%, 35%, 30%, 25% or 20% the strength that it binds to the compound-trimer complex. The antibody may bind to the other molecule at less than about 20%, less than about 15%, less than about 10% or less than about 5%, less than about 2% or less than about 1% the strength that it binds to the compound-trimer complex. The antibody specifically (or selectively) binds to a compound-trimer complex compared with (i) the trimeric form of the TNFα in the absence of the compound and/or (ii) the compound in the absence of the TNFα trimer.

The rates at which an antibody binds to a compound-trimer complex is referred to herein as the "on" rate" $k_{on\text{-}a}b$ and the rate at which the antibody dissociates from the compound-trimer complex is referred to herein as the "off" rate or $k_{off\text{-}ab}$. As used herein, the symbol "$K_{D\text{-}ab}$" denotes the binding affinity (dissociation constant) of an antibody for a compound-trimer complex. $K_{D\text{-}ab}$ is defined as $k_{off\text{-}ab}/k_{on\text{-}ab}$. Antibodies may have slow "on" rates, which can be measured in minutes by mass spectral analysis of the compound-trimer complex and antibody peak intensities. $K_{D\text{-}ab}$ values for an antibody can be estimated by repeating this measurement at different antibody: compound-trimer complex ratios.

The $K_{D\text{-}ab}$ value of the antibody for binding to a compound-trimer complex may be at least about 1.5 times, 2 times, 3 times, 4 times, 5 times, 10 times, 20 times, 30 times, 40 times, 50 times, 60 times, 70 times, 80 times, 90 times, 100 times, 200 times, 300 times or 400 times lower, or lower, than the $K_{D\text{-}a}b$ value of the antibody for binding to the trimeric TNF superfamily member in the absence of the compound and/or the $K_{D\text{-}ab}$ value of the antibody for binding to the compound in the absence of the trimeric TNF superfamily member. The $K_{D\text{-}ab}$ value of the antibody for binding to a compound-trimer complex may be decreased at least about 10 times, at least about 100 times, at least about 200 times, or at least about 300 times the $K_{D\text{-}ab}$ value of the TNF superfamily trimer binding to the TNF superfamily receptor in the absence of the test compound, i.e. the binding affinity of the antibody for the compound-trimer complex is typically increased at least about 10-fold, suitably at least about 100-fold, more suitably at least about 200-fold, most suitably at least about 300-fold compared to the binding affinity of the antibody to the trimeric TNF superfamily member in the absence of the compound and/or the binding affinity of the antibody to the compound in the absence of the trimeric TNF superfamily member.

The binding affinity may be given in terms of binding affinities ($K_{D\text{-}ab}$) and may be given in any appropriate units, such as μM, nM or pM. The smaller the $K_{D\text{-}ab}$ value, the larger the binding affinity of the antibody to the compound-trimer complex.

The $K_{D\text{-}a}b$ value of the antibody for binding to the compound-trimer complex may be at least about 1.5 times, 2 times, 3 times, 4 times, 5 times, 10 times, 20 times, 30 times, 40 times, 50 times, 60 times, 70 times, 80 times, 90 times, 100 times lower, or even lower than the $K_{D\text{-}ab}$ value of the antibody for binding to the trimeric TNF superfamily member in the absence of the compound and/or the $K_{D\text{-}ab}$ value of the antibody for binding to the compound in the absence of the trimeric TNF superfamily member.

The decrease in the $K_{D\text{-}ab}$ value of the antibody for binding to the compound-trimer complex compared to the $K_{D\text{-}ab}$ value of the antibody binding to the trimeric TNF superfamily member in the absence of the compound and/or the $K_{D\text{-}ab}$ value of the antibody for binding to the compound in the absence of the trimeric TNF superfamily member may result from an increase in the on rate ($k_{on\text{-}a}b$) of the antibody binding to the compound-trimer complex compared to the antibody binding to the trimeric TNF superfamily member in the absence of the compound and/or the antibody binding to the compound in the absence of the trimeric TNF superfamily member; and/or a decrease in the off rate ($k_{off\text{-}ab}$) compared to the antibody binding to the trimeric TNF superfamily member in the absence of the compound and/or the antibody binding to the compound in the absence of the trimeric TNF superfamily member.

The on rate ($k_{on\text{-}ab}$) of the antibody binding to the compound-trimer complex is increased compared to the on rate of the antibody binding to the trimeric TNF superfamily member in the absence of the compound and/or the antibody binding to the compound in the absence of the trimeric TNF superfamily member. The off rate ($k_{off\text{-}ab}$) of the antibody binding to the compound-trimer complex is decreased compared to the off rate of the antibody binding to the trimeric TNF superfamily member in the absence of the compound and/or the antibody binding to the compound in the absence of the trimeric TNF superfamily member. The on rate ($k_{on\text{-}ab}$) of the antibody binding to the compound-trimer complex is increased, and the off-rate ($k_{off\text{-}ab}$) of the antibody binding to the compound-trimer complex is decreased, compared to the antibody binding to the trimeric TNF superfamily member in the absence of the compound and/or the antibody binding to the compound in the absence of the trimeric TNF superfamily member.

The $k_{on\text{-}ab}$ value of the antibody binding to the compound-trimer complex may be increased by at least about 1.5-fold or at least two-fold and at least about three fold compared to the $k_{on\text{-}ab}$ value of the antibody binding to the trimeric TNF superfamily member in the absence of the compound and/or the antibody binding to the compound in the absence of the trimeric TNF superfamily member and/or the $k_{off\text{-}ab}$ value of the antibody binding to the compound-trimer complex may be decreased by at least about two-fold, at least about 10-fold, at least about 20-fold, at least about 30-fold, at least about 40-fold, at least about 50-fold, at least about 60-fold, at least about 70-fold, at least about 80-fold more suitably at least about 90-fold compared to the $k_{off\text{-}ab}$ value of the antibody binding to the trimeric TNF superfamily member in the absence of the compound and/or the antibody binding to the compound in the absence of the trimeric TNF superfamily member.

The $k_{on\text{-}ab}$, $k_{off\text{-}ab}$, and $K_{D\text{-}ab}$ values may be determined using any appropriate technique, for example surface plasmon resonance, mass spectrometry and isothermal calorimetry.

The $K_{D\text{-}ab}$ value of the antibody binding to a compound-trimer complex may be 1 nM, 900 pM, 700 pM, 500 pM, 100 pM, 10 pM or less (typically down to about 1 pM). Antibodies of the invention will bind to the compound-trimer complexes of the invention with high affinity, for example in the picomolar range. The $K_{D\text{-}ab}$ value of the antibody binding to a compound-trimer complex may be 1 nM or less, 900 pM or less, 700 pM or less, 500 pM or less, 400 pM or less, 300 pM or less, 200 pM or less, 100 pM or less, 90 pM or less, 80 pM or less, 70 pM or less, 60 pM or less, 50 pM or less, 40 pM or less, 30 pM or less, 20 pM or less, 10 pM or less (again, down to about 1 pM).

Once a suitable antibody has been identified and selected, the amino acid sequence of the antibody may be identified by methods known in the art. The genes encoding the antibody can be cloned using degenerate primers. The antibody may be recombinantly produced by routine methods.

Antibodies may compete for binding to TNFα with, or bind to the same epitope as, those defined above in terms of H-chain/L-chain, HCVR/LCVR or CDR sequences. In particular, an antibody may compete for binding to TNFα with, or bind to the same epitope as, an antibody which comprises a HCDR1/HCDR2/HCDR3/LCDR1/LCDR2/LCDR3 sequence combination of SEQ ID NOs: 4/5/6/1/2/3 or SEQ ID NOs: 19/20/21/1/17/18. An antibody may compete for binding to TNFα with, or bind to the same epitope as, an antibody which comprises a HCVR and LCVR sequence pair of SEQ ID NOs: 8/7 or SEQ ID NOs: 23/22.

The term "epitope" is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

One can determine whether an antibody binds to the same epitope as, or competes for binding with, a reference antibody by using routine methods known in the art. For example, to determine if a test antibody binds to the same epitope as a reference antibody of the invention, the reference antibody is allowed to bind to a protein or peptide under saturating conditions. Next, the ability of a test antibody to bind to the protein or peptide is assessed. If the test antibody is able to bind to the protein or peptide following saturation binding with the reference antibody, it can be concluded that the test antibody binds to a different epitope than the reference antibody. On the other hand, if the test antibody is not able to bind to protein or peptide following saturation binding with the reference antibody, then the test antibody may bind to the same epitope as the epitope bound by the reference antibody of the invention.

To determine if an antibody competes for binding with a reference antibody, the above-described binding methodology is performed in two orientations. In a first orientation, the reference antibody is allowed to bind to a protein/peptide under saturating conditions followed by assessment of binding of the test antibody to the protein/peptide molecule. In a second orientation, the test antibody is allowed to bind to the protein/peptide under saturating conditions followed by assessment of binding of the reference antibody to the protein/peptide. If, in both orientations, only the first (saturating) antibody is capable of binding to the protein/peptide, then it is concluded that the test antibody and the reference antibody compete for binding to the protein/peptide. As will be appreciated by the skilled person, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50%, 75%, 90% or even 99% as measured in a competitive binding assay (see, e.g., Junghans et al., Cancer Res, 1990: 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

The antibodies of the invention bind to an epitope which comprises at least the following residues of trimeric TNFα: (a) Y115; (b) Q149; and (c) N137 and/or K98 (i.e. N137 or K98 or both N137 and K98), wherein Y115 and Q149 are present on the C chain of trimeric TNFα, and N137 and K98 are present on the A chain of trimeric TNFα, and wherein the residue numbering corresponds to (is according to) TNFα of SEQ ID NO: 36. As discussed further below, SEQ ID NO: 36 represents the sequence of human soluble TNFα. In some instances, the antibody binds an epitope comprising all of Y115, Q149, N137 and K98.

Although these residues are provided for a particular sequence of human soluble TNFα, the skilled person could readily extrapolate the positions of these residues to other TNFα sequences (mouse or rat) using routine techniques. Antibodies binding to epitopes comprising the corresponding residues within these other TNF sequences are therefore also provided by the invention.

Y115 and Q149 are hidden (and non-accessible) within the TNFα trimer in the absence of compound. However, when the TNF trimer is bound by a compound disclosed herein, these residues become accessible within the distorted conformation of the trimer. Accordingly, antibodies of the invention which bind an epitope comprising at least Y115 and Q149 will recognise the distorted conformation of the trimer (which modulates TNF signalling), but not the normal conformation of the trimer in the absence of compound. K98 is also buried to an extent in the symmetrical TNF trimer.

The "A" and "C" chains refer to the first and third monomers, which make up the TNF trimer. The antibodies of the invention therefore recognise a conformational epitope spanning two monomers of the TNF trimer.

In more detail, when looking at a crystal structure of a TNFα trimer from the side it is approximately shaped like a pyramid/cone. When you look down the trimer axis with the N- and C-termini of the monomer ends pointing towards you then you are looking at the "fat" end of the trimer. In the distorted structure with compound, a cleft opens between A and C subunits in which, without being bound by theory, the antibody-of the invention binds.

Which chain is A, B or C may be ascertained by measuring three distances between three C-alpha atoms of three identical residues—e.g. P117 in each chain (G121 is also appropriate).

The three distances form a triangle which is equilateral in apo TNF but distorted when compound is bound. The shortest distance is between BC and the longest between AC (for instance AC=13.8 Å, AB=12.3 Å, BC=10.2 Å); thus looking down through the axis of the molecule with N/C termini pointing towards you the longest distance defines C then A chains going anti-clockwise, then B and C again continuing anti-clockwise.

The antibodies of the invention may bind to an epitope which additionally comprises E146 on the C chain of trimeric TNFα, P117 on the C chain of trimeric TNFα, or both E146 and P117. P117 is also substantially buried in the apo form of the TNF trimer (in the absence of compound). In some instances, an antibody of the invention binds an epitope comprising both E146 and P117.

The antibodies of the invention may also bind to an epitope further comprising A145, which residue present on the C chain of trimeric TNFα.

The antibodies of the invention may also bind to an epitope further comprising Q88, which residue is present on the A chain of TNFα.

The epitope may also further comprise one or more residues selected from the group consisting of:

(a) L63;
(b) L94;
(c) S95; and
(d) A96;

wherein L63 is present on the C chain of trimeric TNFα and L94, S95 and A96 are present on the A chain of trimeric TNFα. These residues are all buried to some extent in the apo form of the TNF trimer.

In some instances, antibodies of the invention bind an epitope further comprising all of L63, L94, S95 and A96.

The epitope may also further comprise one or more residues selected from the group consisting of:

(a) I97;
(b) L93; and
(c) S81, wherein I97, L93 and S81 are all present on the A chain of trimeric TNFα. In some instances, the antibody binds to an epitope further comprising all of these residues.

In addition, the antibody may bind to an epitope further comprising one or more residues selected from the following group:

(a) K65;
(b) Q67;
(c) P113;
(d) D143;
(e) T77;
(f) T79;
(g) I83;
(h) T89;
(g) K90;
(i) V91;
(j) N92;
(k) E135;
(l) I136; and
(m) R138;

wherein K65, Q67, P113 and D143 are present on the C chain of trimeric TNFα and T77, T79, I83, T89, K90, V91, N92, E135, I136 and R138 are present on the A chain of trimeric TNFα. In some instances, an antibody of the invention binds to an epitope further comprising all of these residues.

An antibody of the invention, may also bind to an epitope further comprising one or more residues selected from the following group:

(a) Y119;
(b) Q47; and
(c) S133, wherein all of Y119, Q47 and S133 are present on the A chain of trimeric TNFα. In some instances, an antibody of the invention may bind an epitope further comprising all of these residues.

In some instances, an antibody of the invention may bind an epitope which further comprises either Q27 or R131, or both Q27 and R131, wherein these residues are present on the A chain of trimeric TNFα.

As discussed above, the residue numbering is presented according to SEQ ID NO: 36.

An antibody of the invention may bind to an epitope comprising all of the following residues of TNFα of SEQ ID NO: 36:

(a) T77, T79, T89, K90, V91, N92, L93, L94, S95, A96, I97, E135, I136, N137 and R138, which residues are present on the A chain of trimeric TNFα and K65, Q67, Y115, A145, E146 and Q149, which residues are present on the C chain of trimeric TNFα;

(b) T77, T79, I83, T89, K90, V91, N92, L93, L94, S95, A96, I97, K98, E135, I136, N137 and R138, which residues are present on the A chain of trimeric TNFα and L63, K65, Q67, P113, Y115, D143, A145, E146 and Q149, which residues are present on the C chain of trimeric TNFα;

(c) T77, T79, S81, I83, Q88, T89, K90, V91, N92, L93, L94, S95, A96, I97, K98, E135, I136, N137 and R138, which residues are present on the A chain of trimeric TNFα and L63, K65, Q67, P113, Y115, P117, D143, A145, E146 and Q149, which residues are present on the C chain of trimeric TNFα;

(d) Q27, Q47, T77, T79, S81, I83, Q88, T89, K90, V91, N92, L93, L94, S95, A96, I97, K98, Y119, R131, S133, E135, I136, N137 and R138, which residues are present on the A chain of trimeric TNFα and L63, K65, Q67, P113, Y115, P117, D143, A145, E146 and Q149, which residues are present on the C chain of trimeric TNFα.

To screen for antibodies that bind to a particular epitope, a routine cross-blocking assay such as that described in Antibodies, Harlow and Lane (Cold Spring Harbor Press, Cold Spring Harb., N.Y.) can be performed. Other methods include alanine scanning mutants, peptide blots (Reineke (2004) Methods Mol Biol 248:443-63), or peptide cleavage analysis. In addition, methods such as epitope excision, epitope extraction and chemical modification of antigens can be employed (Tomer (2000) Protein Science 9: 487-496). Such methods are well known in the art.

Antibody epitopes may also be determined by x-ray crystallography analysis. Antibodies of the present invention may therefore be assessed through x-ray crystallography analysis of the antibody bound to the TNFα trimer. Epitopes may, in particular, be identified in this way by determining residues on TNFα within 4 Å of an antibody paratope residue. A 5 Å limit may also be used to determine residues.

Antibodies of the invention may also compete with antibodies which bind an epitope comprising the TNFα residues described herein. Methods of identifying such antibodies are discussed in the present invention.

The antibodies of the invention may be used to identify compounds of the invention as described herein. The antibodies of the invention may also be used as target engagement biomarkers. A target engagement biomarker can be used to detect the engagement, i.e. the binding of a ligand to a target of interest. In the present case, the antibodies of the invention only bind to the complexes of compounds of the invention with trimeric TNFα. Therefore, if an antibody of the invention is able to bind to a compound-trimer complex, this is evidence that the ligand (compound) has bound to the target of interest (TNFα trimer). Antibodies of the invention can be modified to add a detectable marker as described herein. Therefore, engagement of a compound of the invention with a target TNFα may be detected using such an antibody.

The use of antibodies of the invention as target engagement biomarkers is potentially useful in a clinical or preclinical environment, where a sample may be taken from a subject being treated according to the present invention. The sample obtained from the subject may be treated with an antibody of the invention in order to determine whether the compound used to treat the subject has bound to the target TNFα. The sample obtained from the subject may be any appropriate tissue or fluid, such as blood, plasma or urine. The subject may be any mammal including human.

Accordingly, the invention provides the use of an antibody of the invention as a target engagement biomarker for the detection of a compound-trimer complex comprising trimeric TNFα and a compound that is capable of binding to trimeric TNFα, whereby the compound-trimer complex binds to the requisite TNFα receptor and modulates the signalling induced by the trimer through the receptor in a sample obtained from a subject. The modulation is suitably antagonism of TNFR1 signalling.

Similarly, the present invention provides a method of detecting target engagement of a compound to trimeric TNFα, whereby the compound-trimer complex binds to the requisite receptor and modulates the signalling induced by the trimer through the receptor, said method comprising:

(a) obtaining a sample from a subject administered said compound;

(b) contacting an antibody of the invention to said sample and a control sample, wherein said antibody is detectable;

(c) determining the amount of binding of said detectable antibody to said sample and said control sample, wherein binding of said detectable antibody to said sample greater than binding of said detectable antibody to said control sample indicates target engagement of said compound to said trimeric TNFα.

Methods of detecting antibodies, and measuring the amount of binding of an antibody to a target, are well known in the art. Typically, antibodies can be labelled. Such labels include enzymes, biotin/streptavidin, fluorescent proteins and fluorescent dyes.

Binding of an antibody to a target may be measured, for example, by an immunoassay method. Immunoassays include Western Blotting, ELISA, immunofluorescence, immunohistochemistry and flow cytometry. Any appropriate technique may be used to measure binding of the antibody to the TNFα.

Binding of the detectable antibody to the sample from a subject who has been administered the compound is compared with binding of the antibody to a control sample. The control sample may be any appropriate sample. The control sample is typically a "negative control" which is representative of binding of the antibody to the trimeric TNFα in the absence of the compound. For example, the sample may be obtained from the patient prior to administration of the compound. The control may also be based on previously determined measurements e.g. from a number of samples from different subjects in the absence of compound. Measurements from about 5, 10, 20, 50 or 100 subjects may be used in determining the control value. The control may be an average value, or a range of all the values obtained.

The experimental conditions e.g. methods of detection are the same for the sample from a subject administered the compound, and for the control sample. The antibody is also the same in both cases.

Greater binding (increased binding) of the detectable antibody to the sample from the patient administered the compound compared with binding of the antibody to the control sample is indicative of target engagement of the compound to the trimeric TNFα. In other words, equivalent or lower binding (decreased binding) for the sample from the patient administered the compound relative to the control indicates that there is no target engagement of said compound. In other words, no significant difference in the two amounts indicates that there is no target engagement.

The skilled person can readily determine when there is increased binding relative to the control. For example when the control is a range of data, target engagement may be determined based on the spread of the data, the difference between the control data and the detected binding of the antibody in the sample in question, and calculated confidence levels. It is also possible to identify target engagement when the detected binding for the sample in question is higher than the maximum amount of binding detected in any negative control.

Target engagement may be detected if binding of the antibody is increased by about 30% or more relative to the highest amount in the control range. Target engagement may also be detected if binding of the antibody is increased by about 40% or more, or about 50% or more relative to the control range. The same applies when the control is an average value, or a single value based on a sample from the patient prior to administration of the compound. There is of course no upper limit to the percentage increase relative to the control.

An antibody of the invention may be used to screen for a compound that elicits a conformational change in trimeric TNFα, wherein said conformational change modulates the signalling of the requisite TNFα receptor on binding of the trimeric TNFα. In a non-limiting example, the modulation may be antagonism of TNFR1 signalling.

The antibodies of the present invention may be used in the treatment and/or prophylaxis of a pathological condition. Accordingly, provided is an antibody of the invention for use in a method of therapy practiced on the human or animal body. The invention also provides a method of therapy comprising the administration of an antibody of the invention to a subject. The antibody of the invention may be used in any therapeutic indication and/or pharmaceutical composition described herein.

Antibody Assays

As described herein, the present invention provides antibodies that selectively bind to at least one compound-trimer complex described herein relative to their binding to the compound alone or to the TNFα in the absence of the compound. These antibodies may be used to identify further compounds or classes of compounds having the same properties.

Monoclonal antibodies may be generated against TNFα using the standard techniques described herein. These anti-TNFα antibodies can then be screened for antibodies that bind to compound-trimer complexes of the invention, or for monoclonal antibodies for which binding to the TNFα is inhibited by compounds as described herein.

Alternatively, monoclonal antibodies can be generated against particular TNFα trimer-compound complexes. These antibodies can then be screened for monoclonal antibodies that selectively bind to the TNFα in the presence of the compound relative to their binding to the TNFα in the absence of the compound.

Once an antibody that selectively binds to at least one compound-trimer complex of the invention relative to its binding to the compound alone or to the TNFα in the absence of the compound has been generated, it can be used to screen for other compounds possessing the same activity as the test compounds. For example, compounds (1)-(7) as described herein can be used to screen for other compounds.

Accordingly, the invention provides an assay for identifying a compound of the invention comprising the steps of:
a) performing a binding assay to measure the binding affinity of a test compound-trimer complex to an antibody of the invention;
b) comparing the binding affinity as measured in step (a) with the binding affinity of a different compound-trimer complex known to bind with high affinity to the antibody referred to in step (a); and
c) selecting the compound present in the compound-trimer complex of step (a) if its measured binding affinity is acceptable when considered in the light of the comparison referred to in step (b).

As will be appreciated, the "different" compound-trimer complex referred to in step (b) above will generally be a complex containing the same TNFα trimer as the compound-trimer complex of step (a), but a different compound. The compound of step (b) may be any of compounds (1)-(7).

By "acceptable" in step (c) is meant that the binding affinity of the compound-trimer complex referred to in step (a) and the binding affinity of the different compound-trimer complex referred to in step (b) are at least comparable. The binding affinity of the compound-trimer complex referred to in step (a) may be at least equal to the binding affinity of the different compound-trimer complex referred to in step (b). The binding affinity may be even higher (i.e. a lower $K_D$ value) for the compound in step (a) compared with the compound in step (b). Selective binding of said antibody to said complex is measured relative to the binding of said antibody to the TNFα in the absence of the compound or to the compound in the absence of the TNFα.

The binding affinity of the compound-trimer complex referred to in step (a) will generally be superior to the binding affinity of the different compound-trimer complex referred to in step (b). The difference in the binding affinity of the compound-trimer complex referred to in step (a) relative to the binding affinity of the different compound-trimer complex referred to in step (b) will be within limits of 10-fold, 20-fold, 50-fold, 100-fold, 200-fold or 500-fold.

Libraries of compounds can be assayed using the antibodies of the invention. The library compounds can be incubated with said antibody in the presence and absence of TNFα. A compound that forms part of a compound-trimer complex that binds to an antibody of the invention only in the presence of both the TNFα and the compound is a likely candidate to have the same activity as the compounds described herein. The assays disclosed herein may then be used to verify whether the test compound is a compound as described herein.

One or more of the antibodies of the invention may be used in the assay. A generic antibody that is capable of binding to complexes of any compound of the invention with a particular TNFα may be used in the antibody assay of the invention.

A panel of multiple antibodies of the present invention that are specific for different compound-trimer complexes may be used in the antibody assay of the invention. The panel of antibodies may include at least 5, at least 10, at least 15, at least 20, at least 30, at least 40 or at least 50 antibodies (for example up to 75 antibodies).

The antibody assay of the present invention may be a high throughput assay that is capable of screening a large number of test compounds over a short space of time to identify compounds of the present invention.

The TNFα and its receptors may be purified or present in mixtures, such as in cultured cells, tissue samples, body fluids or culture medium. Assays may be developed that are qualitative or quantitative, with the latter being useful for determining the binding parameters (affinity constants and kinetics) of the test compound to trimeric forms of TNFα, and also of the binding parameters of the compound-trimer complex to the requisite TNF receptor.

The sample comprising the TNFα and the compound may further comprise a destabilising agent. Destabilising agents, also known as chaotropes, include low molar concentrations (e.g. 1M) of urea, guanidine or acetonitrile, high concentrations (e.g. 6M or higher) of these reagents will result in complete dissociation of the TNFα trimer and unfolding of the constituent TNFα monomeric subunits. The destabilising agent may be DMSO, typically at a concentration of 5%, 10% or higher.

The test compounds may have any or/all of the properties discussed above.

TNF Superfamily and their Receptors

There are 22 TNF superfamily members currently known: TNFα (TNFSF1A), TNFβ (TNFSF1B), CD40L (TNFSF5), BAFF (TNFSF13B/BlyS), APRIL (TNFSF13), OX40L (TNFSF4), RANKL (TNFSF11/TRANCE), TWEAK (TNFSF12), TRAIL (TNFSF10), TL1A (TNFSF15), LIGHT (TNFSF14), Lymphotoxin, Lymphotoxin β (TNFSF3), 4-1BBL (TNFSF9), CD27L (TNFSF7), CD30L (TNFSF8), EDA (Ectodysplasin), EDA-A1 (Ectodysplasin A1), EDA-A2 (Ectodysplasin A2), FASL (TNFSF6), NGF and GITRL (TNFSF18).

In the invention, the TNF superfamily member is TNFα. TNFα exists in both a soluble (TNFα$_s$) and membrane-bound form (TNFα$_m$). When TNFα referred to herein encompasses both the TNFα$_s$ and TNFα$_m$ forms. TNFα is typically in the TNFα$_s$ form. The TNFα$_s$ may comprise the sequence of SEQ ID NO: 35 or SEQ ID NO: 36, or a variant thereof (as described above).

The assays of the invention may be used to identify modulators of TNFα. Specifically, the assays of the invention may be used to identify compounds that bind to TNFα, particularly to trimeric forms of TNFα, and that stabilise these trimers in a conformation that is capable of binding to the requisite TNF receptor, and which modulate signalling through said receptor. The TNFα may be TNFα$_s$.

The compound described herein may be a modulator of at least TNFα. The TNFα is typically TNFα$_s$.

The compound-trimer complex of the invention includes the trimeric form of TNFα. The TNFα is typically TNFα$_s$.

Members of the TNF superfamily bind to, and initiate signalling through TNF receptors. There are currently 34 known TNF receptors: 4-1BB (TNFRSF9/CD137), NGF R (TNFRSF16), BAFF R (TNFRSF13C), Osteoprotegerin (TNFRSF11B), BCMA (TNFRSF17), OX40 (TNFRSF4), CD27 (TNFRSF7), RANK (TNFRSF11A), CD30 (TNFRSF8), RELT (TNFRSF19L), CD40 (TNFRSF5), TACI (TNFRSF13B), DcR3 (TNFRSF6B), TNFRH3 (TNFRSF26), DcTRAIL R1 (TNFRSF23), DcTRAIL R2 (TNFRSF22), TNF-R1 (TNFRSF1A), TNF-R2 (TNFRSF1B), DR3 (TNFRSF25), TRAIL R1 (TNFRSF10A), DR6 (TNFRSF21), TRAIL R2 (TNFRSF10B), EDAR, TRAIL R3 (TNFRSF10C), Fas (TNFRSF6/CD95), TRAIL R4 (TNFRSF10D), GITR (TNFRSF18), TROY (TNFRSF19), HVEM (TNFRSF14), TWEAK R (TNFRSF12A), TRAMP (TNFRSF25), Lymphotoxin β R (TNFRSF3) and XEDAR.

When TNF-R is referred to herein this encompasses both TNF-R1 and TNF-R2, including the extracellular domain (ECD) of TNF-R1 and TNF-R2. The assays of the invention may be used to identify compounds that modulate the signalling of TNFα through any requisite TNF receptor. The assays of the invention may be used to identify compounds that modulate the signalling of TNFα through TNF-R1 or TNF-R2. The TNF superfamily member may be TNFα and the TNF receptor may be TNF-R1. In an embodiment of the invention, the TNF superfamily member may be TNFα, and the TNF receptor may be TNF-R1. The assays of the invention may be used to identify compounds which act by specifically modulating the signalling of TNFα through TNF-R1. In particular, the compounds may act by modulating the signalling of TNFα through TNF-R1, but have no effect on signalling of TNFα through TNF-R2.

Therapeutic Indications

TNFα is the archetypal member of the TNF superfamily. TNFα is a pleiotropic cytokine that mediates immune regulation and inflammatory responses. In vivo, TNFα is also known to be involved in responses to bacterial, parasitic and viral infections. In particular, TNFα is known to have a role in rheumatoid arthritis (RA), inflammatory bowel diseases (including Crohn's disease), psoriasis, Alzheimer's disease (AD), Parkinson's disease (PD), pain, epilepsy, osteoporosis, asthma, sepsis, fever, Systemic lupus erythematosus (SLE) and Multiple Sclerosis (MS) and cancer. TNFα is also known to have a role in Amyotrophic Lateral Sclerosis (ALS), ischemic stroke, immune complex-mediated glomerulonephritis, lupus nephritis (LN), antineutrophil cytoplasmic antibodies (ANCA-) associated glomerulonephritis, minimal change disease, diabetic nephropathy (DN), acute kidney injury (AKI), obstructive uropathy, kidney allograft rejection, cisplatin-induced AKI and obstructive uropathy.

Other members of the TNF superfamily are known to be involved in autoimmune disease and immune deficiencies. In particular, members of the TNF superfamily are known to be involved in RA, SLE, cancer, MS, asthma, rhinitis, osteoporosis and multiple myeloma (MM). TL1A is known to play a role in organ transplant rejection.

A compound described herein may be used to treat, prevent or ameliorate any condition that can be treated, prevented or ameliorated by a conventional TNF superfamily member modulator. The compound may be used alone or in combination with a conventional TNF superfamily member modulator. Any condition that results, partially or wholly, from pathogenic signalling through a TNF receptor by a TNF superfamily member or from a deficiency in signalling through a TNF receptor by a TNF superfamily member may in principle be treated, prevented or ameliorated. Pathogenic signalling through a TNF receptor by a TNF superfamily member includes but is not limited to increased signalling through a TNF receptor over and above the normal physiological level of signalling, signalling through a TNF receptor which is initiated normally, but which fails to stop in response to normal physiological signals and signalling through a TNF receptor that is within the normal physiological range of magnitude, but which is initiated by non-physiological means. The invention relates to the treatment, prevention or amelioration of conditions mediated or influenced by TNFα.

The compounds that interact with TNFα are accordingly beneficial in the treatment and/or prevention of various human ailments. These include autoimmune and inflammatory disorders; neurological and neurodegenerative disorders; pain and nociceptive disorders; and cardiovascular disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, vasculitis, polymyositis, scleroderma, multiple sclerosis, ankylosing spondylitis, rheumatoid arthritis and Sjögren's syndrome. Autoimmune endocrine disorders include thyroiditis. Organ-specific autoimmune disorders include Addison's disease, haemolytic or pernicious anaemia, glomerulonephritis (including Goodpasture's syndrome), Graves' disease, idiopathic thrombocytopenic purpura, insulin-dependent diabetes mellitus, juvenile diabetes, uveitis, inflammatory bowel disease (including Crohn's disease and ulcerative colitis), pemphigus, atopic dermatitis, autoimmune hepatitis, primary biliary cirrhosis, autoimmune pneumonitis, autoimmune carditis, myasthenia gravis, spontaneous infertility, osteoporosis, asthma and muscular dystrophy (including Duchenne muscular dystrophy).

Neurological and neurodegenerative disorders include Alzheimer's disease, Parkinson's disease, Huntington's disease, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction).

A compound may be used to treat or prevent inflammatory disorders, CNS disorders, immune disorders and autoimmune diseases, pain, osteoporosis, fever and organ transplant rejection. A compound may be used to treat or prevent rheumatoid arthritis, inflammatory bowel diseases (including Crohn's disease), psoriasis, Alzheimer's disease, Parkinson's disease, epilepsy, asthma, sepsis, systemic lupus erythematosus, multiple sclerosis, asthma, rhinitis, cancer and osteoporosis. A compound may be used to treat or prevent rheumatoid arthritis (RA), non specific inflammatory arthritis, erosive bone disease, chondritis, cartilage degeneration and/or destruction, juvenile inflammatory arthritis, Still's Disease (juvenile and/or adult onset), juvenile idiopathic arthritis, juvenile idiopathic arthritis (both oligoarticular and polyarticular forms), inflammatory bowel diseases (including Crohn's disease, ulcerative colitis, indeterminate colitis, pouchitis), psoriasis, psoriatic arthopathy, ankylosing spondylitis, Sjogren's Disease, Alzheimer's disease (AD), Behcet's Disease, Parkinson's disease (PD), amyotrophic lateral sclerosis (ALS), ischemic stroke, pain, epilepsy, osteoporosis, osteopenia, anaemia of chronic disease, cachexia, diabetes, dyslipidemia, metabolic syndrome, asthma, chronic obstructive airways (or pulmonary) disease, sepsis, fever, respiratory distress syndrome, systemic lupus erythematosus (SLE), multiple sclerosis (MS) immune complex-mediated glomerulonephritis, lupus nephritis (LN), antineutrophil cytoplasmic antibodies (ANCA-) associated glomerulonephritis, minimal change disease, diabetic nephropathy (DN), acute kidney injury (AKI), obstructive uropathy, kidney allograft rejection, cisplatin-induced AKI and obstructive uropathy, eye diseases (including diabetic retinopathy, diabetic macular oedema, retinopathy of prematurity, age related macular degeneration, macular oedema, proliferative and/or non proliferative retinopathy, corneal vascularisation including neovascularization, retinal vein occlusion, various forms of uveitis and keratitis), thyroiditis, fibrosing disorders including various forms of hepatic fibrosis, various forms of pulmonary fibrosis, systemic sclerosis, scleroderma, cancer and cancer associated complications (including skeletal complications, cachexia and anaemia).

As discussed above, antibodies of the present invention may be used as target engagement biomarkers to assess the effectiveness of treatment with a compound or complex as described herein. In one embodiment, a sample taken from a subject treated with a compound or complex described herein may be contacted with an antibody of the invention. The antibody may then be used to determine the amount of TNFα-compound complex present within the sample. The amount of complex determined using the antibody may be related to the effectiveness of the treatment. For example, the more complex detected by the antibody of the invention, the more effective the treatment. The amount of complex determined using the antibody is directly proportional to the effectiveness of the treatment. For example, doubling the amount of complex determined using the antibody may be indicative of a doubling of the effectiveness of the treatment.

An antibody of the invention may be used to determine the amount of compound-trimer complex using any appropriate technique. Standard techniques are known in the art and are disclosed herein. For example, ELISA and Western blotting with an antibody of the invention may be used to determine the amount of compound-trimer complex.

The amount of the compound-trimer complex may be determined by measuring the mass of the compound-trimer complex, the concentration of the compound-trimer complex, and the molarity of the compound-trimer complex. This amount may be given in any appropriate units. For example, the concentration of the compound-trimer complex may be given in pg/ml, ng/ml or µg/ml. The mass of the compound-trimer complex may be given in pg, ng or µg.

The amount of the compound-trimer complex in a sample of interest may be compared with the level of the compound-trimer complex in another sample, such as a control sample, as described herein. In such a method, the actual amount of the compound-trimer complex, such as the mass, molar amount, concentration or molarity of the compound-trimer complex in the samples may be assessed. The amount of the compound-trimer complex may be compared with that in another sample without quantifying the mass, molar amount, concentration or molarity of the compound-trimer complex. Thus, the amount of the compound-trimer complex in a sample according to the invention may be assessed as a relative amount, such as a relative mass, relative molar amount, relative concentration or relative molarity of the compound-trimer complex based on a comparison between two or more samples.

Pharmaceutical Compositions, Dosages and Dosage Regimes

An antibody, compound or complex of the invention may be provided in a pharmaceutical composition. The pharmaceutical composition that will normally be sterile and will typically include a pharmaceutically acceptable carrier and/or adjuvant. A pharmaceutical composition of the present invention may additionally comprise a pharmaceutically acceptable adjuvant and/or carrier.

As used herein, "pharmaceutically acceptable carrier" includes any and all solvents, dispersion media, coatings, antibacterial and antifungal agents, isotonic and absorption delaying agents, and the like that are physiologically compatible. The carrier may be suitable for parenteral, e.g. intravenous, intramuscular, intradermal, intraocular, intraperitoneal, subcutaneous, spinal or other parenteral routes of administration, for example by injection or infusion. Alternatively, the carrier may be suitable for non-parenteral administration, such as a topical, epidermal or mucosal route of administration. The carrier may be suitable for oral administration. Depending on the route of administration, the modulator may be coated in a material to protect the compound from the action of acids and other natural conditions that may inactivate the compound.

The pharmaceutical compositions of the invention may include one or more pharmaceutically acceptable salts. A "pharmaceutically acceptable salt" refers to a salt that retains the desired biological activity of the parent compound and does not impart any undesired toxicological effects. Examples of such salts include acid addition salts and base addition salts.

Pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. In many cases, it will be desirable to include isotonic agents, for example, sugars, polyalcohols such as mannitol, sorbitol, or sodium chloride in the composition.

Therapeutic compositions typically must be sterile and stable under the conditions of manufacture and storage. The composition can be formulated as a solution, microemulsion, liposome, or other ordered structure suitable to high drug concentration.

Pharmaceutical compositions of the invention may comprise additional active ingredients.

Also within the scope of the present invention are kits comprising antibodies, compounds and/or complexes of the invention and instructions for use. The kit may further contain one or more additional reagents, such as an additional therapeutic or prophylactic agent as discussed above.

The compounds identified by the methods and/or antibodies of the invention and the antibodies of the present invention or formulations or compositions thereof may be administered for prophylactic and/or therapeutic treatments.

In therapeutic applications compounds are administered to a subject already suffering from a disorder or condition as described above, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as a "therapeutically effective amount".

In prophylactic applications, formulations are administered to a subject at risk of a disorder or condition as described above, in an amount sufficient to prevent or reduce the subsequent effects of the condition or one or more of its symptoms. An amount adequate to accomplish this is defined as a "prophylactically effective amount". Effective amounts for each purpose will depend on the severity of the disease or injury as well as the weight and general state of the subject.

A subject for administration may be a human or non-human animal. The term "non-human animal" includes all vertebrates, e.g., mammals and non-mammals, such as non-human primates, sheep, dogs, cats, horses, cows, chickens, amphibians, reptiles, etc. An embodiment of the invention is administration to humans.

A compound or pharmaceutical composition of the invention may be administered via one or more routes of administration using one or more of a variety of methods known in the art. As will be appreciated by the skilled artisan, the route and/or mode of administration will vary depending upon the desired results. Examples of routes of administration for compounds or pharmaceutical compositions of the invention include intravenous, intramuscular, intradermal, intraocular, intraperitoneal, subcutaneous, spinal or other parenteral routes of administration, for example by injection or infusion. The phrase "parenteral administration" as used herein means modes of administration other than enteral and topical administration, usually by injection. Alternatively, compound or pharmaceutical composition of the invention can be administered via a non-parenteral route, such as a topical, epidermal or mucosal route of administration. The compound or pharmaceutical composition of the invention may be for oral administration.

A suitable dosage of a compound or pharmaceutical composition of the invention may be determined by a skilled medical practitioner. Actual dosage levels of the active ingredients in the pharmaceutical compositions of the present invention may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A suitable dose may be, for example, in the range of from about 0.01 µg/kg to about 1000 mg/kg body weight, or from about 0.1 µg/kg to about 100 mg/kg body weight, of the patient to be treated. As a non-limiting example, a suitable dosage may be from about 1 µg/kg to about 10 mg/kg body weight per day or from about 10 µg/kg to about 5 mg/kg body weight per day.

Dosage regimens may be adjusted to provide the optimum desired response (e.g., a therapeutic response). For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Administration may be in single or multiple doses. Multiple doses may be administered via the same or different routes and to the same or different locations. Alternatively, doses can be via a sustained release formulation, in which case less frequent administration is required. Dosage and frequency may vary depending on the half-life of the antagonist in the patient and the duration of treatment desired.

As mentioned above, compounds or pharmaceutical composition of the invention may be co-administered with one or other more other therapeutic agents. For example, the other agent may be an analgesic, anesthetic, immunosuppressant or anti-inflammatory agent.

Combined administration of two or more agents may be achieved in a number of different ways. Both may be administered together in a single composition, or they may be administered in separate compositions as part of a combined therapy. For example, the one may be administered before, after or concurrently with the other.

The following examples are presented below so as to provide those of ordinary skill in the art with a complete disclosure and description of how to make and use the

EXAMPLES

Example 1—Synthesis of Compounds

Synthesis of compound (1) is disclosed in WO 2013/186229 (Example 44).

Synthesis of compound (2) is disclosed in WO 2013/186229 (Example 89).

Synthesis of compound (3) is disclosed in WO 2014/009295 (Example 129).

Synthesis of compound (4) is disclosed in WO 2014/009295 (Example 173).

Synthesis of compound (5) is disclosed in WO 2014/009295 (Example 319).

Synthesis of compound (6) is disclosed in WO 2013/186229 (Example 490).

Synthesis of compound (7) is disclosed in WO 2013/186229 (Example 156).

Example 2—Antibody Derivation

Following the immunisation of 5 Sprague Dawley rats with human TNFα in complex with the benzimidazole compound (1), immune B cells were cultured in 96-well plates to induce clonal expansion and antibody secretion (Tickle, S. et al., High throughput screening for high affinity antibodies Journal of Laboratory Automation 2009 14: 303-307). Culture supernatants were screened for IgG antibodies preferentially binding to human TNFα in complex with compound (1) (at a 50 fold molar excess), compared to apo human TNFα, in a homogeneous bead-based FMAT assay. Human TNFα (+/− compound (1)) was presented on bead surfaces (superavidin-coated Bangs Beads, catalogue number CP01N) by a capture system using a human TNF-Receptor I-Fc fusion protein (R&D Systems catalogue number 372-R1-050), bound with biotinylated anti-human Fc (Jackson catalogue number 109-066-098).

Antibodies which demonstrated preferential binding to the TNFα-compound (1) complex were termed 'conformation-selective' and were taken forward for cloning. The Fluorescent Foci method (U.S. Pat. No. 7,993,864/Europe EP1570267B1) was used to identify and isolate antigen-specific B cells from positive wells, and specific antibody variable region genes were recovered from single cells by reverse transcription (RT)-PCR.

The amino acid sequences of two representative antibodies, CA185_01974 and CA185_01979, which demonstrated conformation-selective binding to both human and mouse TNFα+compound are shown below:

```
CA185_01974.0 (VR0001837)
Light chain variable region (LCVR) (CDRs
underlined)
                                  SEQ ID NO: 7
DIQMTQSPASLPASPEEIVTITCQASQDIGNWLSWYQQKPGKSPQLLIYGA

TSLADGVPSRFSASRSGTQYSLKISRLQVEDFGIFYCLQGQSTPYTFGAGT

KLELK

Heavy chain variable region (HCVR) (CDRs
underlined)
                                  SEQ ID NO: 8
DVQLVESGGGLVQPGRSLKLSCAASGFTFSAYYMAWVRQAPTKGLEWVASI

NYDGANTFYRDSVKGRFTVSRDNARSSLYLQMDSLRSEDTATYYCTTEAYG

YNSNWFGYWGQGTLVTVSS

CA185_01979.0 (VR0001842)
Light chain variable region (LCVR) (CDRs
underlined)
                                  SEQ ID NO: 22
DIQMTQSPASLSASLEEIVTITCQASQDIGNWLSWYQQKPGKSPHLLIYGT

TSLADGVPSRFSGSRSGTQYSLKISGLQVADIGIYVCLQAYSTPFTFGSGT

KLEIK

Heavy chain variable region (HCVR) (CDRs
underlined)
                                  SEQ ID NO: 23
EVHLVESGPGLVKPSQSLSLTCSVTGYSITNSYWDWIRKFPGNKMEWMGYI

NYSGSTGYNPSLKSRISISRDTSNNQFFLQLNSITTEDTATYYCARGTYGY

NAYHFDYWGRGVMVTVSS
```

Example 3—Potential Epitope of the Derived Antibodies

Given the ability of the rat-derived antibodies to bind to both human and mouse TNFα in the presence of compounds, detailed analysis of rat, mouse and human amino acid sequences, together with X-ray crystal structures of TNFα, was undertaken to see if a likely epitope could be determined.

```
Rat UniProt P16599
                                            (SEQ ID NO: 32)
          10         20         30         40         50         60
MSTESMIRDV ELAEEALPKK MGGLQNSRRC LCLSLFSFLL VAGATTLFCL LNFGVIGPNK 70         80         90        100        110        120
EEKFPNGLPL ISSMAQTLTL RSSSQNSSDK PVAHVVANHQ AEEQLEWLSQ RANALLANGM 130        140        150        160        170        180
DLKDNQLVVP ADGLYLIYSQ VLFKGQGCPD YVLLTHTVSR FAISYQEKVS LLSAIKSPCP 190        200        210        220        230
KDTPEGAELK PWYEPMYLGG VFQLEKGDLL SAEVNLPKYL DITESGQVYF GVIAL Mouse UniProt P06804
                                            (SEQ ID NO: 33)
          10         20         30         40         50         60
MSTESMIRDV ELAEEALPQK MGGFQNSRRC LCLSLFSFLL VAGATTLFCL LNFGVIGPQR
```

-continued

```
         70         80         90        100        110        120
DEKFPNGLPL ISSMAQTLTL RSSSQNSSDK PVAHVVANHQ VEEQLEWLSQ RANALLANGM 130        140        150        160        170        180
DLKDNQLVVP ADGLYLVYSQ VLFKGQGCPD YVLLTHTVSR FAISYQEKVN LLSAVKSPCP 190        200        210        220        230
KDTPEGAELK PWYEPIYLGG VFQLEKGDQL SAEVNLPKYL DFAESGQVYF GVIAL
```

Human UniProt P01375

(SEQ ID NO: 34)
```
         10         20         30         40         50         60
MSTESMIRDV ELAEEALPKK TGGPQGSRRC LFLSLFSFLI VAGATTLFCL LHFGVIGPQR 70         80         90        100        110        120
EEFPRDLSLI SPLAQAVRSS SRTPSDKPVA HVVANPQAEG QLQWLNRRAN ALLANGVELR 130        140        150        160        170        180
DNQLVVPSEG LYLIYSQVLF KGQGCPSTHV LLTHTISRIA VSYQTKVNLL SAIKSPCQRE 190        200        210        220        230
TPEGAEAKPW YEPIYLGGVF QLEKGDRLSA EINRPDYLDF AESGQVYFGI IAL
```

From alignments and comparison of the rat, mouse and human TNFα UniProt sequences, examples of where the rat amino acid sequence differs from the human, and where the human and mouse sequences are identical in the mature, cleaved product include N168, I194, F220 and A221 (residues and numbering from the human sequence).

These residues are highlighted on the crystal structure of human TNFα (1TNF) (FIG. 1). It is possible that any of these amino acids are included in the epitope targeted by the antibodies CA185_01974 and CA185_01979.

Following cloning of the antibody variable regions into mouse IgG and mouse Fab (no-hinge) vectors, the conformation-selective nature of the binding of antibodies CA185_01974 and CA185_01979 was confirmed, using a variety of test compounds bound to TNFα, in HPLC, BIAcore, ELISA and cell-based assays.

A more comprehensive analysis of the epitope for CA185_01979 is presented in Examples 9 and 10 below.

Figure 2:
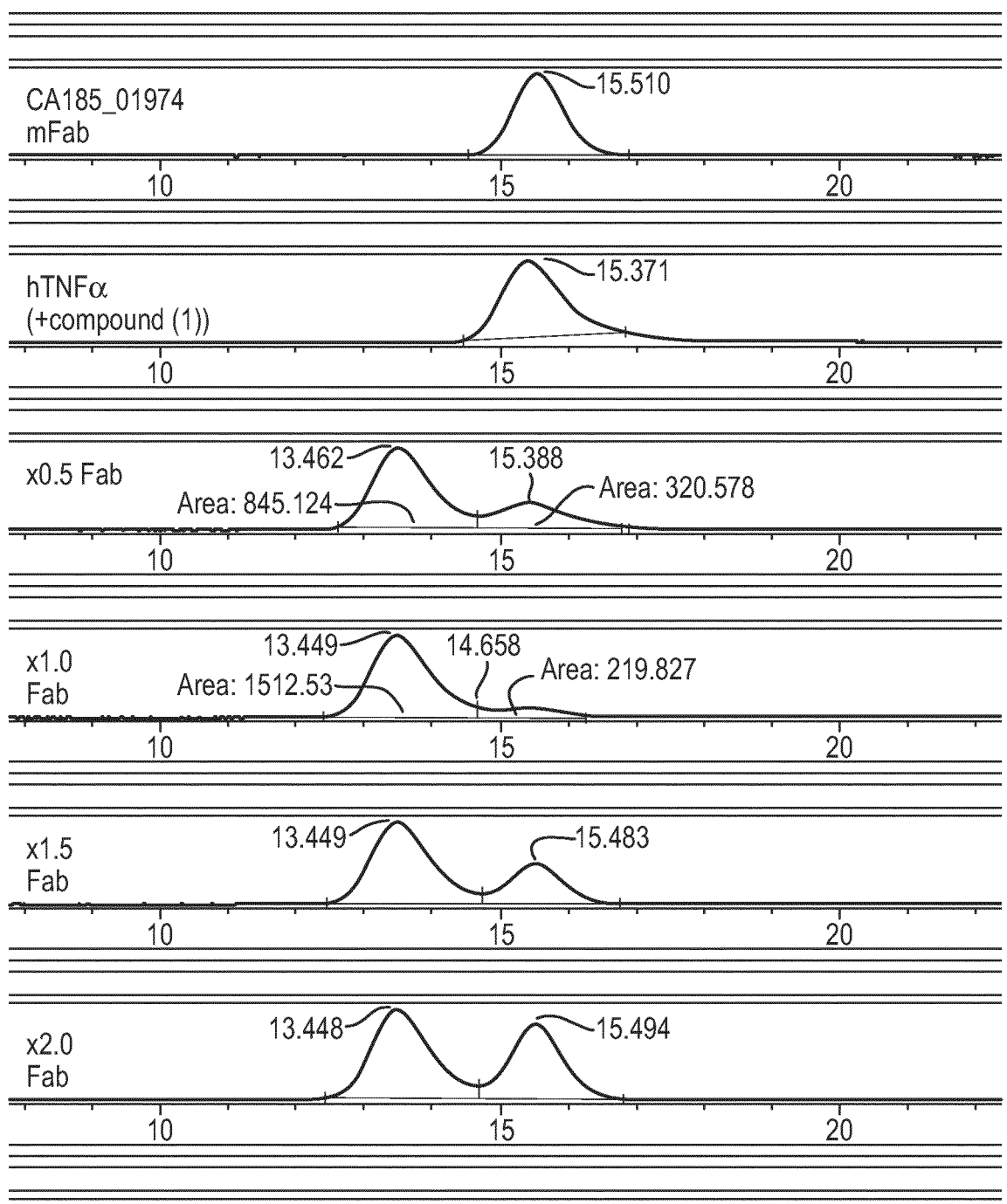

Example 4—High Performance Liquid Chromatography (HPLC) to Determine Antibody Characteristics Specific binding of mouse Fab fragments was demonstrated by complex formation between CA185_01974 and human TNFα complexed with compound (1) using size exclusion chromatography. Results are shown in FIG. 2. As shown in this Figure, with a 0.5× molar excess of Fab the predominant peak corresponds to bound Fab and trimer-compound complex (although there is a small peak showing the presence of some trimer-compound complex not bound to Fab). At a 1.0× molar excess of Fab there is single higher molecular weight peak corresponding to Fab bound to trimer-compound complex. At 1.5× and 2× molar excesses of Fab, there is a growing lower molecular peak corresponding to unbound Fab.

The stoichiometry was therefore determined to be 1 Fab: 1 TNFα trimer, with excess Fab appearing at 1.5× and 2× molar excess.

Figure 3:
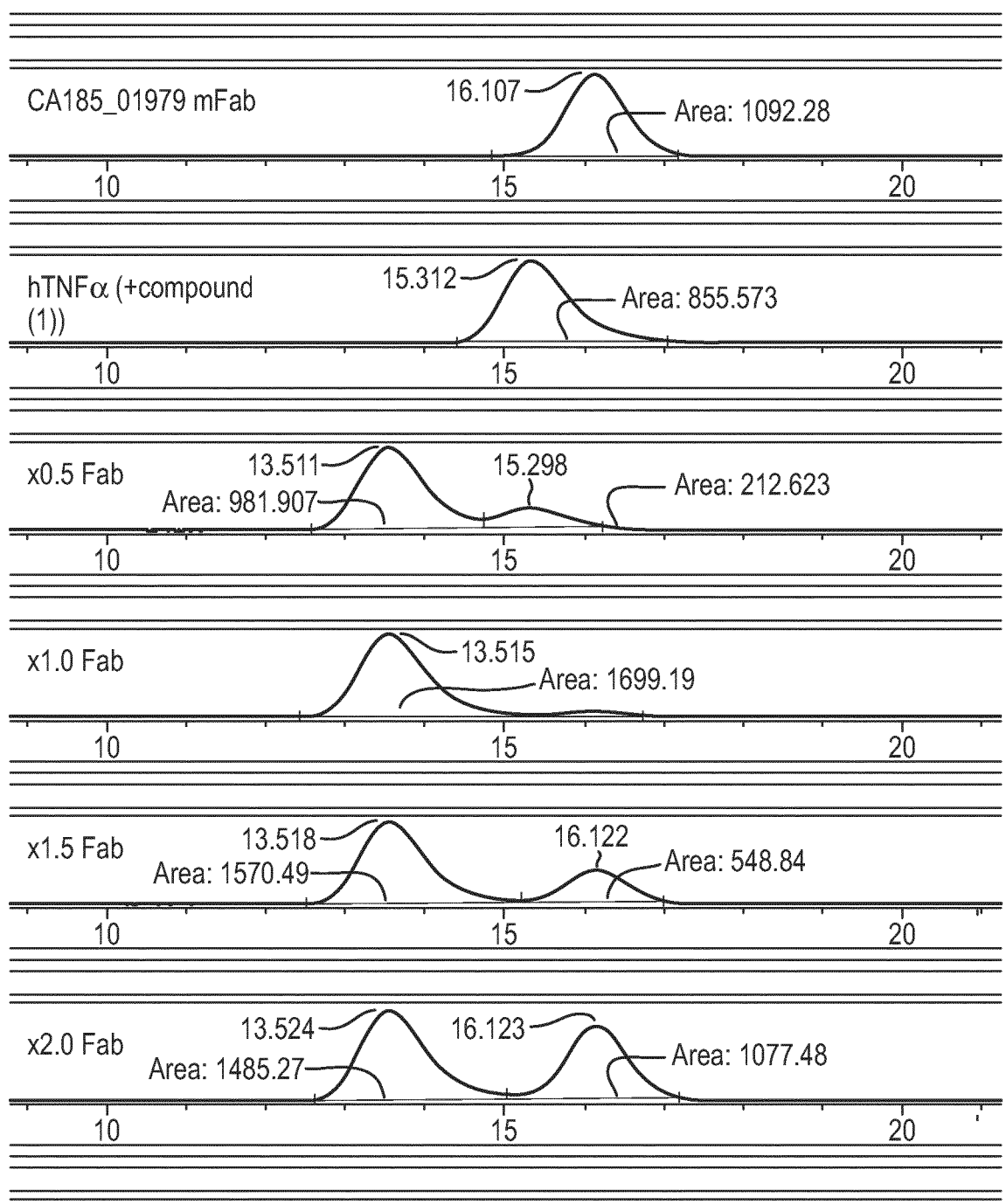

Binding of CA185_01979 to human TNFα complexed with compound (1) was also investigated using size exclusion chromatography. Results are shown in FIG. 3. As for CA185_01974, the stoichiometry was determined to be 1 Fab: 1 TNFα trimer, with excess Fab appearing at 1.5× and 2× molar excess.

Example 5—BIAcore Assays to Determine Antibody Characteristics

Surface plasmon resonance was performed at 25° C. using a BIAcore T200 (GE Healthcare). Anti-Mouse Fc (Jackson 115-006-071) was immobilised on a CM5 Sensor Chip (GE Healthcare) via amine coupling chemistry to a capture level of ~6000 response units. HBS-EP buffer (10 mM HEPES pH 7.4, 0.15 M NaCl, 3 mM EDTA, 0.05% (v/v) surfactant P20-GE Healthcare)+1% DMSO was used as the running buffer. A 10 μl injection of each IgG at 1 μg/ml was used for capture by the immobilised anti-mouse Fc to create the TNFα-binding surface. Human or mouse TNFα (in-house) at 50 nM was pre-incubated with 2 μM compound in HBS-EP+ (1% DMSO) for 5 hours.

A 3 minute injection of human or mouse TNFα+/−test compound was passed over each captured IgG at a flow rate of 30 μl/min. The surface was regenerated at a flow-rate of 10 μl/min by a 60 s injection of 40 mM HCl×2 and a 30 s 5 mM NaOH. Double referenced background subtracted binding curves were analysed using the T200 Evaluation software (version 1.0) following standard procedures. Kinetic parameters were determined from the fitting algorithm.

The kinetic binding data for human and mouse TNFα in the presence and absence of test compounds from two chemical series are shown in Tables 1 and 2 below.

TABLE 1

BIAcore data with human TNFα

| Antibody | Human TNFα | ka ($M^{-1}s^{-1}$) | kd ($s^{-1}$) | KD (M) |
| --- | --- | --- | --- | --- |
| CA185_01974 | +compound (2) | $4.2 \times 10^5$ | $3.9 \times 10^{-5}$ | $9.4 \times 10^{-11}$ |
| CA185_01974 | +compound 1 | $3.2 \times 10^5$ | $3.8 \times 10^{-5}$ | $1.2 \times 10^{-10}$ |
| CA185_01974 | apo | $6.6 \times 10^4$ | $1.3 \times 10^{-3}$ | $1.9 \times 10^{-8}$ |
| CA185_01979 | +compound (2) | $5.7 \times 10^5$ | $3.3 \times 10^{-5}$ | $5.8 \times 10^{-11}$ |
| CA185_01979 | +compound (1) | $4.7 \times 10^5$ | $1.6 \times 10^{-5}$ | $3.4 \times 10^{-11}$ |
| CA185_01979 | apo | $1.1 \times 10^5$ | $7.1 \times 10^{-4}$ | $6.7 \times 10^{-9}$ |

Both CA185_01974 and CA185_01979 demonstrated >2 log selective binding for compound-distorted human TNFα, with representative test compounds from two chemical series.

TABLE 2

BIAcore data with mouse TNFα

| Antibody | Mouse TNFα | ka (M$^{-1}$s$^{-1}$) | kd (s$^{-1}$) | KD (M) |
|---|---|---|---|---|
| CA185_01974 | +compound (2) | 6.7 × 10$^4$ | 4.8 × 10$^{-5}$ | 7.1 × 10$^{-10}$ |
| CA185_01974 | +compound (1) | 5.8 × 10$^4$ | 8.8 × 10$^{-5}$ | 1.5 × 10$^{-9}$ |
| CA185_01974 | apo | 4.2 × 10$^4$ | 4.9 × 10$^{-3}$ | 1.2 × 10$^{-7}$ |
| CA185_01979 | +compound (2) | 1.9 × 10$^5$ | 3.5 × 10$^{-5}$ | 1.9 × 10$^{-10}$ |
| CA185_01979 | +compound (1) | 1.6 × 10$^5$ | 6.3 × 10$^{-5}$ | 3.8 × 10$^{-10}$ |
| CA185_01979 | apo | 7.2 × 10$^4$ | 2.0 × 10$^{-3}$ | 2.7 × 10$^{-8}$ |

Both CA185_01974 and CA185_01979 demonstrated >1.5 and >2 log selective binding for compound-distorted mouse TNFα, with representative test compounds from two chemical series.

Example 6—ELISAs to Determine Antibody Characteristics

A sandwich ELISA was developed to measure the concentration of TNFα bound to compounds of the invention, using antibody CA185_01974.0 that specifically detects the conformation of TNFα when in complex with these compounds. Briefly, a microtitre plate was coated with CA185_01974.0 to immobilise TNFα in complex with a test compound. TNFα was incubated overnight at 2-8° C. with a 50× molar excess of the test compound. Following this overnight incubation, TNFα was serially diluted in neat human plasma depleted of endogenous TNFα, in the presence of heterophilic antibody blockers, and added to the coated plate. Curves were generated with a concentration range of 0.78 pg/ml-50 pg/ml TNFα. A biotinylated polyclonal anti TNFα antibody was used to detect bound TNFα, with streptavidin-peroxidase and TMB substrate to give a colorimetric signal. Sensitivity of the assay was increased with the use of tyramide signal amplification, using the ELAST kit from Perkin Elmer, as an additional step between streptavidin-peroxidase and the substrate.

An ELISA was also developed to measure total TNFα (free TNFα+TNFα in complex with a test compound) in parallel. For this assay the coating antibody was replaced with a commercial anti-TNFα polyclonal antibody (Invitrogen AHC3812). The sample incubation time was also increased to 3 hours. All other steps were identical to the conformation-specific assay. This enables the amount of TNFα in complex with a test compound to be calculated as a proportion of total TNFα.

Figure 4:
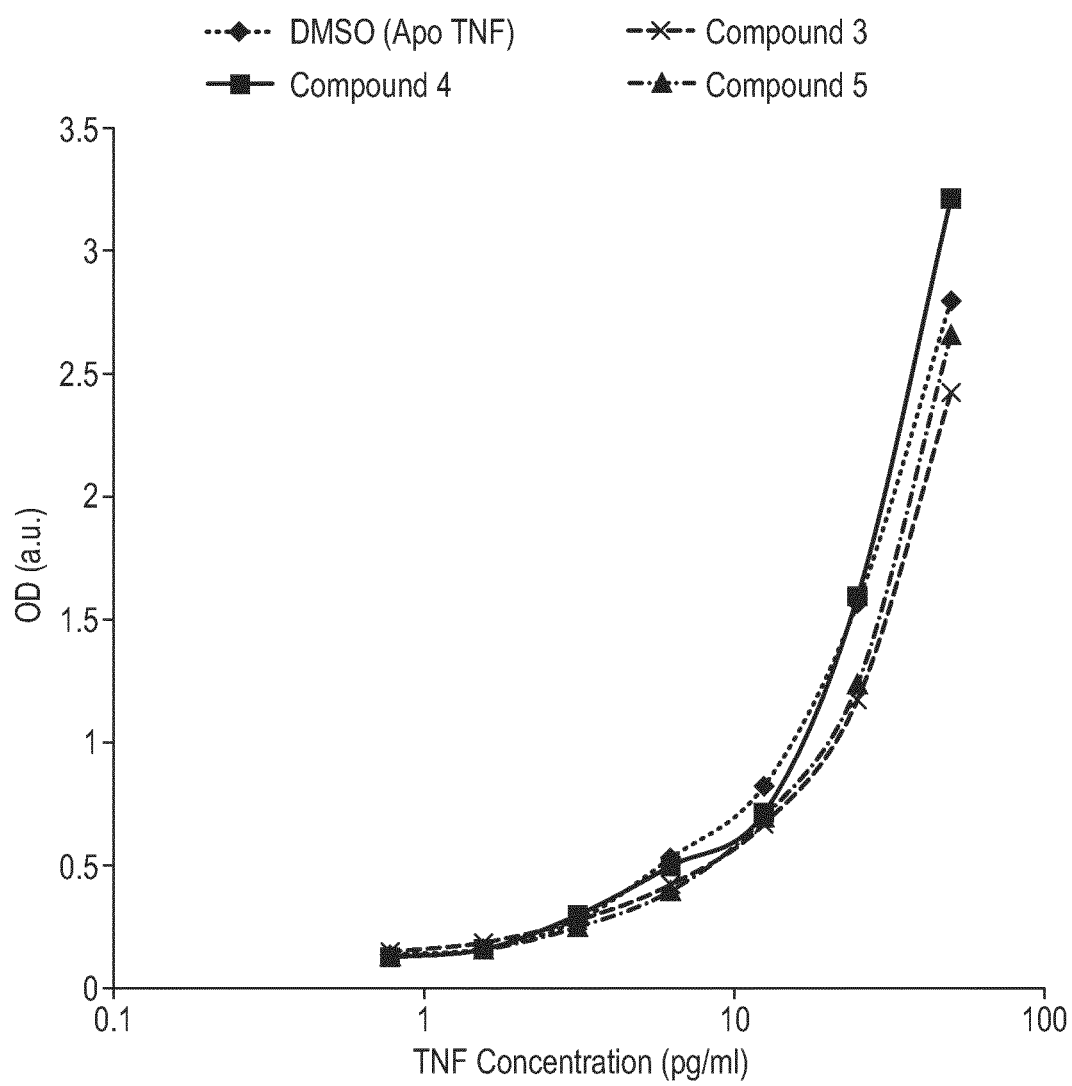

Results for the total TNFα ELISA with compounds (3), (4) and (5) are shown in FIG. 4.

Figure 5:
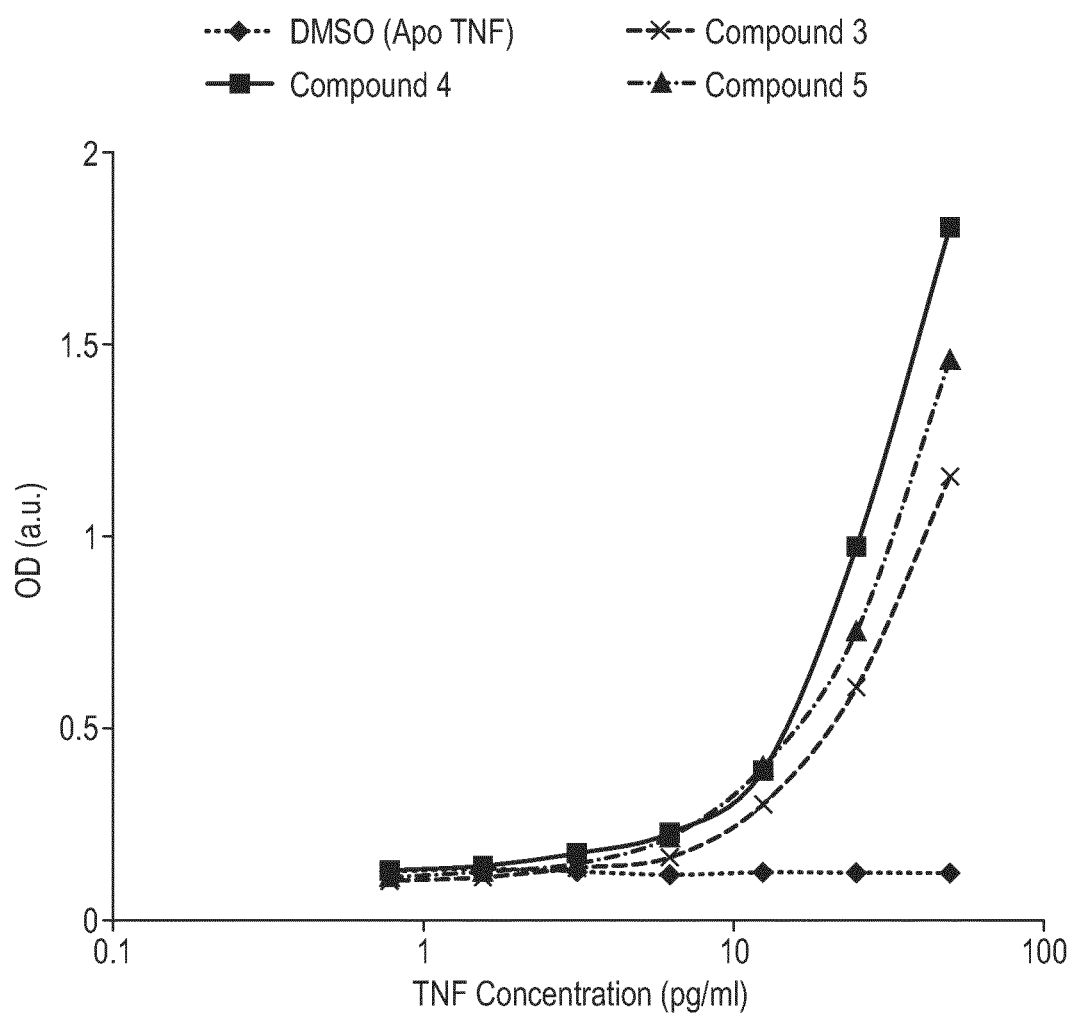

Results of the conformation specific TNFα ELISA with CA185_01974.0 and compounds (3), (4) and (5) are shown in FIG. 5. Apo TNFα gave no signal in this assay, demonstrating the specific nature of the binding of antibody CA185_01974 to compound-bound TNFα. The antibody was able to recognise TNFα bound by a variety of test compounds from different chemical series.

Example 7—Cell-Based Assays to Determine Antibody Characteristics

Recombinant antibodies were also tested for binding to compound-distorted TNFα in a FACS assay using human embryonic kidney (HEK) JumpIn cells, which overexpress TNF-RI after induction with doxycycline at 1 µg/ml for 2.5 hours. HEK cells were trypsinised and incubated for 2 h in medium to allow recovery of digested TNFRI levels. Human TNFα at 2 µg/mL was pre-incubated with 40 µM compound (1) or 0.4% DMSO for 1 h at 37° C. The pre-incubation mix was added to the cells for 1 h on ice (dilution 1:4, final concentrations: 0.5 µg/mL human-TNFα+/−10 compound (1) or 0.1% DMSO). Cells were washed, fixed (1.5% PFA) and stained with 1 or 10 µg/mL antibody for 1 h on ice. (Secondary antibody: anti-mouse-Alexa488), before analysis for receptor-bound TNFα.

Figure 6:
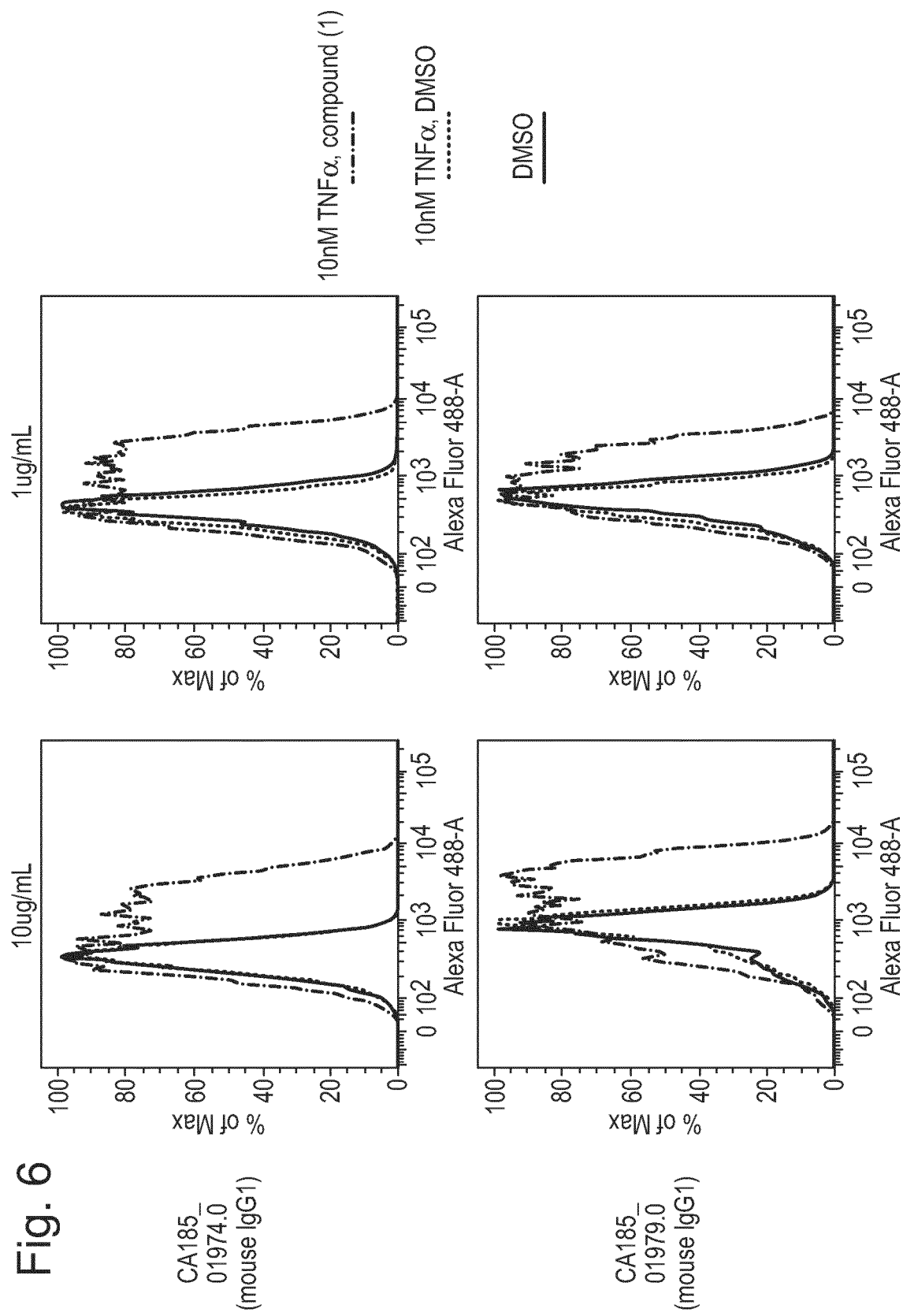

As shown in FIG. 6, FACS histogram plots of staining with CA185_01974 and CA185_01979 at 1 and 10 µg/ml demonstrate that the antibodies only recognise TNFα which has been pre-incubated with compound (1). There is no staining with the DMSO control.

In addition, specific binding of CA185_01974 and CA185-01979 Fab fragments was demonstrated with compound-distorted membrane-bound TNFα. An engineered NS0 cell line, which overexpresses membrane TNFα, due to knock-out of the TACE cleavage site was incubated with 0.001-10 µM compound (1) or 0.1% DMSO for 1 h at 37° C. Cells were washed, fixed and stained with antibody Fab fragments at 0.01 or 0.1 µg/ml for 1 hour on ice. (Secondary antibody was anti-mouse Fab-DyeLight488 from Jackson ImmunoResearch).

Figure 7:
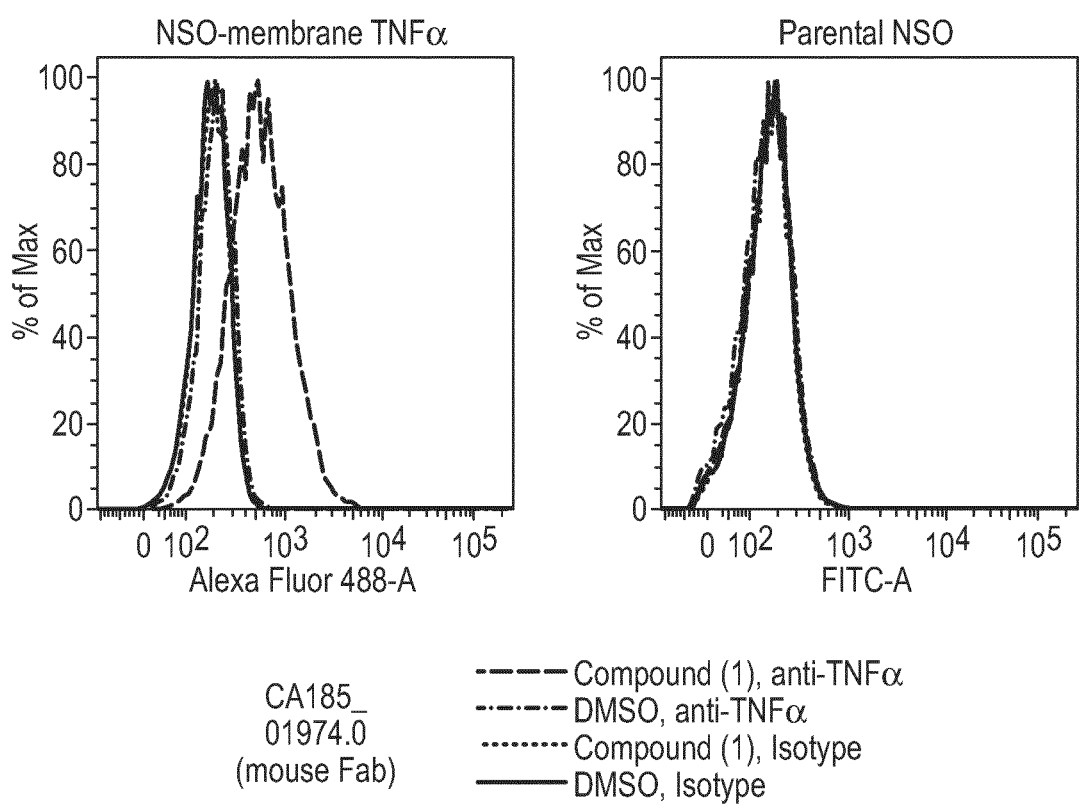

FACS histogram plots of staining with CA185_01974 (FIG. 7) and CA185_01979 Fab fragments demonstrate that the antibodies only recognise TNF which has been pre-incubated with compound (1). There is no staining with the DMSO controls.

Example 8—Antibody CA185_01974, Shows a 300-Fold Selectivity for Human TNF-Compound (4) Complex Compound (4) was incubated with human and cynomolgus TNF and titrated over mouse full length antibody CA185_01974 to determine an accurate affinity value. The experiment included the following controls: (i) human or cynomolgus TNF+DMSO over 1974; (ii) human or cynomolgus TNF+DMSO over no antibody; and (iii) human or cynomolgus TNF+compound (4) over no antibody. Each sample and control was carried out in duplicate and used four concentrations in each replicate.

As shown in FIGS. 8 and 9, background binding of hTNF+compound (4) and cTNF+compound (4) increased by 5-10 RU over the course of the assay. This is seen in the higher response of h/cTNF+compound (4) binding to CA185_01974 in the second duplicate. Binding of hTNF and cTNF in the absence of compound (4) was consistently very low.

Kinetics of hTNF+DMSO binding mouse full length IgG CA185_1974_P8 was very similar in this assay to previous single concentration analysis. Affinity of cynomolgus TNF for mouse full length IgG CA185_1974_P8 is similar, however the kinetics differ.

Table 3 gives the kinetics of each analyte binding to CA185_1974_P8. Table 4 gives the average values and the fold difference +/−compound (4) of TNF kinetics for CA185_1974_p8. FIG. 8 gives the sensograms of both duplicates of cTNF+/−compound (4). FIG. 9 gives the sensograms of both duplicates of hTNF+/−compound (4).

TABLE 3

Binding kinetics of hTNF and cTNF +/− compound (4) to the CA185_1974_P8 antibody

| Duplicate | Antibody | Analyte | ka (1/Ms) | kd (1/s) | KD (M) | KD (pM) |
|---|---|---|---|---|---|---|
| 1 | CA185_1974_P8 | cyno TNF | 1.03E+05 | 1.87E−03 | 1.83E−08 | 18270 |
| 2 | CA185_1974_P8 | cyno TNF | 1.25E+05 | 1.92E−03 | 1.54E−08 | 15350 |
| 1 | CA185_1974_P8 | cyno TNF + compound (4) | 1.84E+05 | 1.46E−05 | 7.91E−11 | 79.1 |
| 2 | CA185_1974_P8 | cyno TNF + compound (4) | 2.01E+05 | 2.06E−05 | 1.03E−10 | 103 |
| 1 | CA185_1974_P8 | human TNF | 8.02E+04 | 1.77E−03 | 2.21E−08 | 22100 |
| 2 | CA185_1974_P8 | human TNF | 1.05E+05 | 1.67E−03 | 1.59E−08 | 15900 |
| 1 | CA185_1974_P8 | human TNF + compound (4) | 3.06E+05 | 1.00E−05 | 3.27E−11 | 32.7 |
| 2 | CA185_1974_P8 | human TNF + compound (4) | 3.07E+05 | 2.73E−05 | 8.88E−11 | 88.8 |

TABLE 4

Average values and fold differences +/− compound (4) of hTNF and cTNF kinetics for CA185_1974_p8.

| | Average of duplicates | | | |
|---|---|---|---|---|
| | ka (1/Ms) | kd (1/s) | KD (M) | KD (pM) |
| cyno TNF | 1.14E+05 | 1.90E−03 | 1.68E−08 | 16810 |
| cyno TNF + compound (4) | 1.93E+05 | 1.76E−05 | 9.09E−11 | 90.92 |
| Fold difference | 1.69 | 107.81 | 184.89 | 184.89 |
| human TNF | 9.27E+04 | 1.72E−03 | 1.90E−08 | 19000 |
| human TNF + compound (4) | 3.06E+05 | 1.86E−05 | 6.08E−11 | 60.76 |
| Fold difference | 3.31 | 92.43 | 312.70 | 312.70 |

Example 9—Compounds and Complexes of Ma et al (2014) and Silvian et al (2011) have Different Characteristics to Those of the Present Invention As described on page 12458 of Ma et al. (2014) JBC 289:12457-12466, C87 was discovered through virtual screening by attempting to find molecules which fit the space occupied by a 7 amino-acid peptide from loop2/domain2 of TNFR1 in its interaction with the external surface of TNFβ. The C87 compound from Ma et al. and the BIO8898 compound from Silvian et al. (2011) ACS Chemical Biology 6:636-647 were tested by the present inventors.
Summary of Findings The Biacore observations described in Ma et al. for C87 could not be repeated.

No evidence of TNF specific inhibition in cells was observed.

Additionally C87 was not observed to bind by mass spectrometry, which is sensitive to millimolar affinities.

Extensive crystallography trials only produced apo-TNF (TNF without compound).

In the fluorescence polarisation (FP) assay, C87 showed no significant inhibition above the interference level of the compound with the fluorescent read-out.

Thermofluor, which measures stabilisation of the thermal melting temperature of TNFα, did show a small stabilisation for C87.

In summary, no evidence was found that C87 binds in the centre of the trimer. The overwhelming majority of the data suggested no direct interaction with TNFα. BIO8898 was also found not to bind to TNFα.
Cells—TNF Induced HEK NFKB Reporter Gene Assay C87 was pre-incubated with TNFα for 1 hour prior to the addition to HEK-293 cells stably transfected with SEAP under the control of NFκB. An appropriate counter-screen was also tested in order to detect non-TNF related (off target) activity. The assay was incubated overnight before inhibition was measured compared to 100% blocking by a control compound. The maximum C87 concentration was 10,000 nM, with a 3-fold serial dilution.

No inhibitory effect could be detected that could not be attributed to off-target activity.
Biacore TNF was immobilised using an avi-tag linker and C87 was passed over the chip. In one experiment, a dose response of C87 from a highest concentration of 10 μM was performed. No binding was observed.

In a second experiment, the flow rate of C87 passing over the chip was reduced. A small shift was observed but overall binding was negligible.

The binding of C87 to TNF described in Ma et al was likely to be super-stoichiometric based on the RU value on the Y-axis. At standard TNF density on the chip this value was in the region of thirty times higher than expected for simple 1:1 binding.

In another experiment, BIO8898 was tested against the immobilised soluble form of CD40L and the soluble form of TNFα by SPR on a Biacore 4000 machine. A geomean IC50 of 17 μM was determined for binding against CD40L whereas no binding was detected at a concentration of up to 100 μM for TNFα in this assay.
Mass Spectrometry There was no evidence of C87 binding to human TNFα (20 μM) at a concentration of 400 μM. A species of lower molecular weight (~473 Da appears to bind at less than 5% occupancy). C87 has a molecular weight of 503 Da. Based on the occupancy at a concentration of 400 μM, an affinity of the low molecular weight species in excess of 1 mM is predicted.
Crystallography Overall a large effort was put into crystallising C87 with TNFα, including testing conditions that routinely work with compounds described in the present application. This comprised setting up a large number of crystallization trials at different ligand concentrations, different protein concentrations, and different soaking times. A few crystals were observed that, on analysis, proved to be salt or TNF with no compound.
Fluorescent Polarization (FP)

C87 was preincubated with TNFα for 1 hour prior to assay against the fluorescent compound (probe). Competition with the fluorescent compound either directly (binding at the same site) or indirectly (disrupting TNF) is detected by a reduction in FP.

Extrapolation of the inhibition curve produced an IC50 of about 100 μM. Fluorescence quenching was, however, observed at the highest concentrations of inhibitor which, when subtracted, resulted in negligible inhibition of C87 in this assay.

Thermofluor

Thermofluor measures the change of melting temperature (Tm) of TNFα due to compound either stabilising or disrupting the protein. A stabilization effect of 3.8° C. was observed at a concentration of 500 μM C87, suggesting the possibility of weak binding, which may not be specific.

Example 10—hTNFα and Fab1974 Complex Structure

1) Protein Expression and Purification

The soluble form of human TNFα (CID2043, UniProt P01375, residues 77-233) was expressed as a fusion protein in E. coli and had the final sequence:

(SEQ ID NO: 35)
SVRSSSRTPSDKPVAHVVANPQAEGQLQWLNRRANALLANGVELRDNQLVV

PSEGLYLIYSQVLFKGQGCPSTHVLLTHTISRIAVSYQTKVNLLSAIKSPC

QRETPEGAEAKPWYEPIYLGGVFQLEKGDRLSAEINRPDYLDFAESGQVYF

GIIAL

The initial "S" of SEQ ID NO: 35 is a cloning artefact and not part of the native sequence of the TNF. The residue numbering of SEQ ID NO: 35 therefore starts from V i.e. V1, R2, S3 etc. SEQ ID NO: 36 represents SEQ ID NO: 35, but without this initial "S" residue i.e.

(SEQ ID NO: 36)
VRSSSRTPSDKPVAHVVANPQAEGQLQWLNRRANALLANGVELRDNQLVVP

SEGLYLIYSQVLFKGQGCPSTHVLLTHTISRIAVSYQTKVNLLSAIKSPCQ

RETPEGAEAKPWYEPIYLGGVFQLEKGDRLSAEINRPDYLDFAESGQVYFG

IIAL

Cells were pre-cultured at 37° C. in rich media, induced with the addition of 0.1% arabinose and allowed to express overnight at 25° C. in vector pEMB54. This vector introduces a cleavable N-terminal His6Smt-tag. The cells were lysed and purified by Ni-NTA chelate chromatography. The fusion protein was eluted with buffer containing imidazole and cleaved by the addition of protease. The final cleaved TNFα protein was purified by a subtractive Ni chelate chromatography step to remove the fusion tag and further purified by size exclusion chromatography to remove the remaining impurities. The final TNFα product was typically concentrated to 20.0 mg/ml and flash frozen in liquid nitrogen.

The extracellular domain of human TNFR1 (CID5602, UniProt P19438, residues 42-184) with N54D and C182S mutations was expressed as a secreted protein in baculovirus infected insect cells and has the final sequence:

(SEQ ID NO: 37)
GSVCPQGKYIHPQDNSICCTKCHKGTYLYNDCPGPGQDTDCRECESGSFTA

SENHLRHCLSCSKCRKEMGQVEISSCTVDRDTVCGCRKNQYRHYWSENLFQ

CFNCSLCLNGTVHLSCQEKQNTVCTCHAGFFLRENECVSSSN

The initial "G" of SEQ ID NO: 37 is a cloning artefact and not part of the native sequence of the TNFR1. The residue numbering of SEQ ID NO: 37 therefore starts from S i.e. 51, V2, C3 etc. SEQ ID NO: 38 represents SEQ ID NO: 37, but without this initial "G" residue i.e.

(SEQ ID NO: 38)
SVCPQGKYIHPQDNSICCTKCHKGTYLYNDCPGPGQDTDCRECESGSFTAS

ENHLRHCLSCSKCRKEMGQVEISSCTVDRDTVCGCRKNQYRHYWSENLFQC

FNCSLCLNGTVHLSCQEKQNTVCTCHAGFFLRENECVSSSN

The fusion protein plasmid was cloned into the pEMB50 expression vector, which encodes a cleavable N-terminal secretion signal and His-tagged fusion protein. Virus was generated using the baculovirus expression system. Infected insect cells secreted the fusion protein into the media. The fusion protein was purified by Ni-NTA chelate chromatography and eluted from the Ni column using an imidazole gradient. The eluted protein was cleaved with protease to release the N-terminal His-fusion tag. The cleaved TNFR1 was subsequently purified by a subtractive Ni chelate chromatography step and further purified by size exclusion chromatography. The final TNFR1 product was typically concentrated to 10.0 mg/ml and flash frozen in liquid nitrogen.

To form the complex, 333 μl of purified human TNFα at 300 mM was mixed with 4,567 μl of SEC buffer (10 mM HEPES, pH 7.5, 150 mM NaCl) and 100 μL of compound (2) (10 mM in DMSO, approximately 10 molar excess) and incubated at 4° C. overnight. The following day, the complex was formed by adding 4080 μl of SEC buffer to 700 μl TNFR1, 5,000 μl of TNFα/UCB1478733 mix, and 220 μl Fab1974 at 500 mM; Total volume of the reaction was 10 ml with a final molar ratio of 3 TNFα monomers (equivalent to 1 trimer): 2.5 TNFR1 receptors: 1.2 Fab. The ternary complex (cytokine, ligand, receptor, and Fab) was incubated for 1 hour at 4° C. The sample was then concentrated to 1.5 ml and was loaded in a single injection on Superdex 200 16/600 size exclusion column (120 ml) that was pre-equilibrated with 10 mM HEPES pH 7.5, 150 mM NaCl. Peak fractions of the ternary complex were selected and concentrated to 13.7 mg/ml and immediately used in crystallization trials.

2) Crystallization

The ternary complex was crystallized by sitting drop vapor diffusion by mixing 0.5 μl of complex with 0.5 μl of Wizard III/IV: 0.1M HEPES, pH7.0, 10% PEG6,000 (condition B8) over 80 μl of the same crystallization solution. Crystals were harvested for data collection approximately 2 months after initial set up. They were cryo-protected in glycerol performed in 5-10-15% steps, then frozen directly in liquid nitrogen for data collection on Jun. 8, 2016 at Advanced Photon Source at Argonne National Laboratory, Life Sciences Collaborative Access Team (LS-CAT), beamline 21-ID-F.

3) Structure Determination

The structure of the human TNFα (CID2043), human TNFR1 (CID5602), and Fab1974 complex with ligand compound (2) was solved by molecular replacement using Phenix.Phaser with input models based upon previously determined structure of human TNFα, human TNFR1, Fab1979 bound with UCB1478733 and a separately determined structure of the isolated Fab1974. Data were integrated in XDS and scaled using XSCALE 1. Initial structure determination and refinement used data to 3.00 Å resolution from a single crystal. Iterative manual model building using Coot 3 and in Phenix.Refine 2 continued until R and Rfree reached R=0.201, Rfree=0.259. Model quality was validated using Coot and MolProbity 4. Final data processing and refinement statistics are listed in Table 1.

4) References

1. Kabsch, W., 2010. Xds. Acta Crystallographica Section D: Biological Crystallography, 66(2), pp. 125-132.
2. Adams, P. D., Afonine, P. V., Bunkóczi, G., Chen, V. B., Davis, I. W., Echols, N., Headd, J. J., Hung, L. W., Kapral, G. J., Grosse-Kunstleve, R. W. and McCoy, A. J., 2010. PHENIX: a comprehensive Python-based system for macromolecular structure solution. Acta Crystallographica Section D: Biological Crystallography, 66(2), pp. 213-221.
3. Emsley, P., Lohkamp, B., Scott, W. G. and Cowtan, K., 2010. Features and development of Coot. Acta Crystallographica Section D: Biological Crystallography, 66(4), pp. 486-501.
4. Chen, V. B., Arendall, W. B., Headd, J. J., Keedy, D. A., Immormino, R. M., Kapral, G. J., Murray, L. W., Richardson, J. S. and Richardson, D. C., 2010. MolProbity: all-atom structure validation for macromolecular crystallography. Acta Crystallographica Section D: Biological Crystallography, 66(1), pp. 12-21.

Data Collection and Refinement Statistics.

| Parameter | Overall (Highest Shell) |
| --- | --- |
| Data collection | Dataset 1 |
| Crystal ID | 272787b8 |
| Beamline | APS 21-ID-F |
| Protein | Human TNFα, Human TNFR1, Fab1974 |
| Ligand | Compound (2) |
| Collection date | Jun. 8$^{th}$, 2016 |
| Oscillation width (°) | 1.0 |
| Frames | 150 |
| Exposure (sec) | 1.5 |
| Distance (mm) | 410 |
| Wavelength (Å) | 0.97872 |
| Data processing | Overall (Highest shell) |
| Space Group | P 4$_1$ 2$_1$ 2 |
| Unit cell (Å, °) | a = b = 99.51, c = 311.35; α = β = γ = 90 |
| Resolution (Å) | 50.00-3.00 (3.08-3.00) |
| I/σ | 14.61 (2.27) |
| Completeness (%) | 99.90 (99.97) |
| Rpim | 0.049 (0.38) |
| R$_{merge}$ (%) | 16.4 (127.9) |
| Reflections (unique) | 32,358 (3,171) |
| Multiplicity | 12.1 (12.4) |

| Parameter | Overall (Highest Shell) |
| --- | --- |
| Refinement statistics | |
| Resolution (Å) | 47.39-3.00 (3.11-3.00) |
| R$_{work}$/R$_{free}$ overall | 22.29/25.56 (33.43/37.58) |
| No. atoms | |
| Protein | 8396 |
| Ligand | 109 |
| Water | 20 |
| ADP (Å$^2$) | |
| Protein | 69.69 |
| Ligand | 64.03 |
| Water | 47.65 |
| r.m.s. deviations | |
| Bond lengths (Å) | 0.04 |
| Bond angles (°) | 0.96 |
| Ramachandran outliers (%) | 0.09 |
| Ramachandran favored (%) | 97.24 |
| Molprobity score | 1.30; 100$^{th}$ percentile* (N = 3130, 3.00 Å ± 0.25 Å) |
| Refined by: | David Fox III |
| Peer Reviewed by: | Deborah G. Conrady |

*100th percentile is the best among structures of comparable resolution; 0th percentile is the worst.

6) Structure Discussion and Figures

Figure 11:
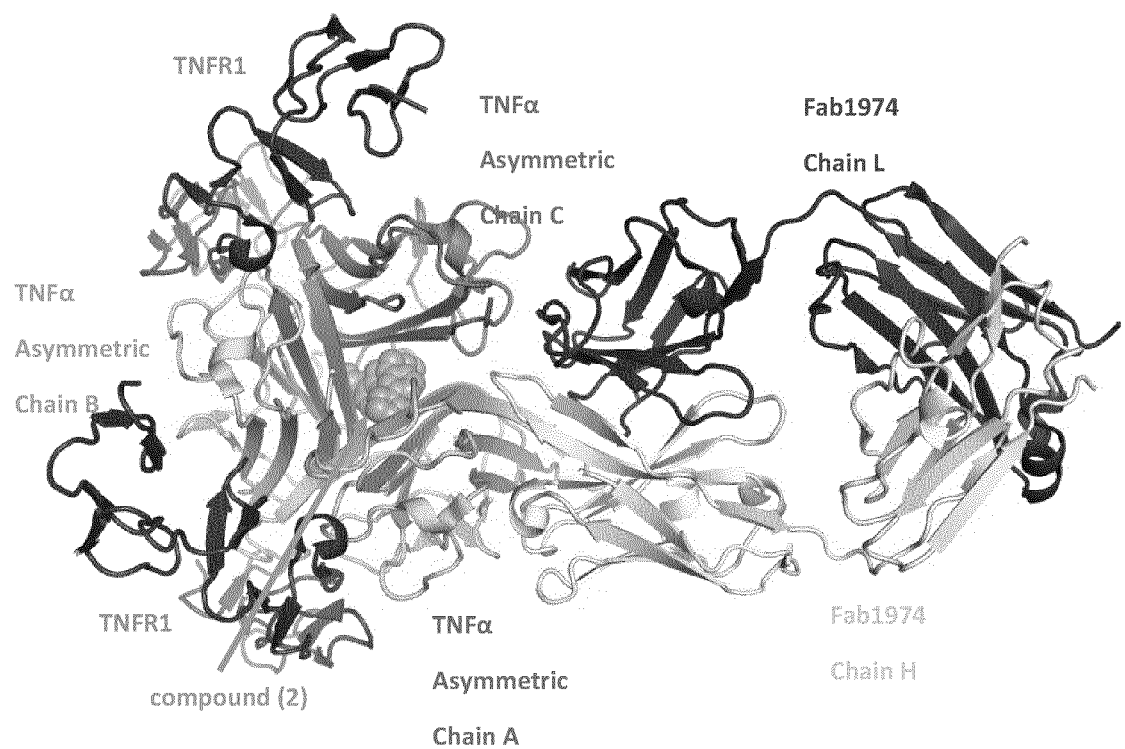

FIG. 11 shows the structure of the Fab1974 bound to a complex of human TNFα asymmetric trimer, compound (2), and 2 human TNFR1 receptors.

The main contact between TNFα and the Fab is via the heavy chain and the displaced TNFα monomer A. Heavy chain CDRs 2 and 3 form a contact with the outer face of monomer A and CDR3 protrudes deeply into the open cleft of the distorted A/C receptor binding site. The positioning of CDR3 in this cleft results in the only contact between the CA1974 heavy chain and TNFα monomer C where pi stacking occurs between Tyr103 of CDR3 and Tyr115 of monomer C.

The light chain of CA1974 also forms a substantial contact with TNFα, bridging the distorted A/C receptor binding cleft. The light chain CDR2 contacts with monomer C exclusively, towards the bottom of the cleft. Only two residues of CDR1 contact TNFα, one binding monomer C and the other monomer A, on the inner faces of the cleft. Light chain CDR3 associates solely with monomer A, interacting with residues towards the top of the cleft.

Figure 12:
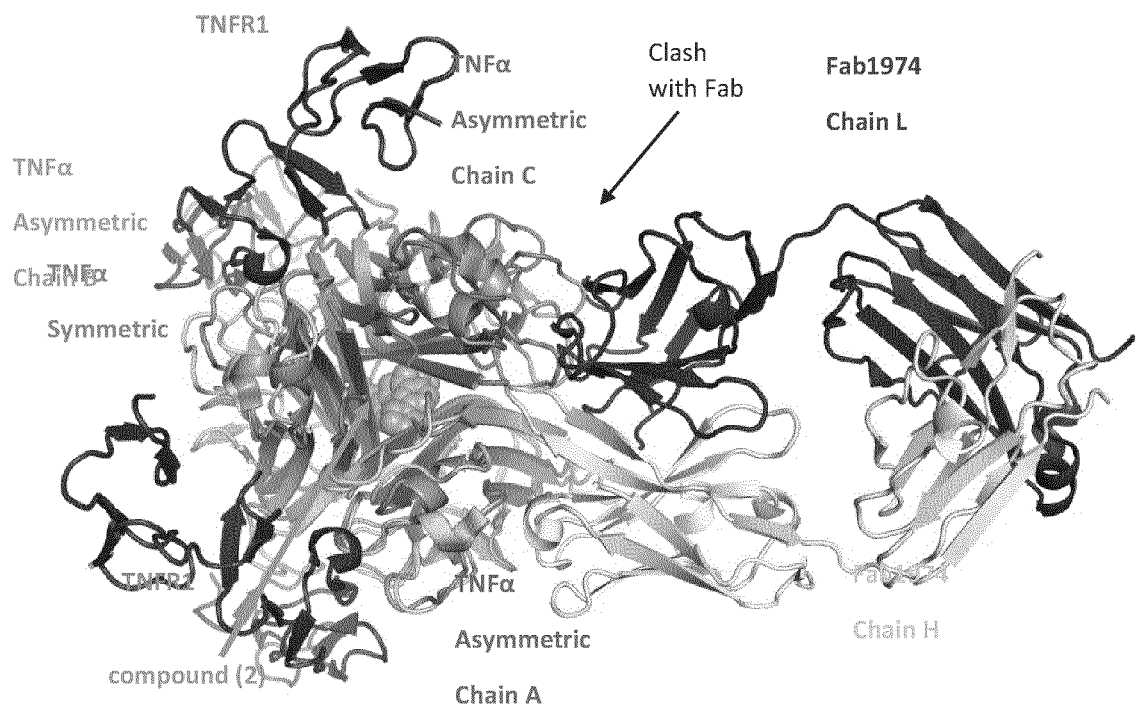

FIG. 12 shows the same structure as FIG. 11, but with a symmetric trimer (i.e. an undistorted trimer in the absence of ligand) modelled in computationally. With this symmetric trimer, the A chain of the trimer retains the interaction with the Fab fragment. However, there is a steric clash between the Fab fragment and the C chain of the trimer.

Example 11—Identification of Epitope Residues

The program NCONT (part of the CCP4 crystallography suite) was used to identify residues between the Fab1974 and the TNF asymmetric trimer, within a distance of 4.0 Å. Any atom in TNFα from a residue within that distance was identified as an epitope residue. Defining an epitope as atoms of the antigen which are within 4.0 Å of antibody atoms is routine in the art (see for example Andersen et al (2006), Protein Science, 15, 2258-2567).

Figure 13:
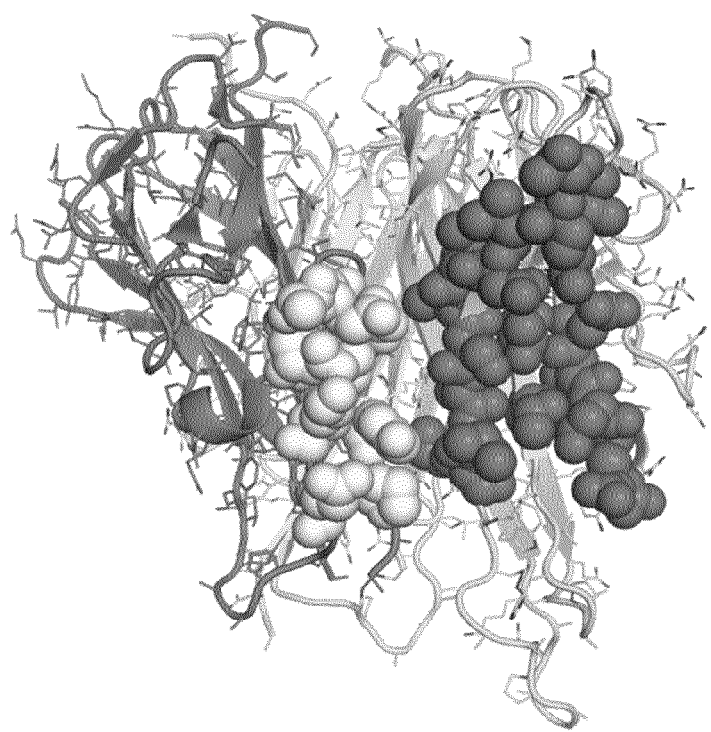

Results of this experimentally determined epitope are presented in FIG. 13. Residues on the A chain of TNFα identified in this way were T77, T79, I83, T89, K90, V91, N92, L93, L94, S95, A96, I97, K98, E135, I136, N137 and R138. Residues on the C chain of TNFα identified in this way were L63, K65, Q67, P113, Y115, D143, A145, E146 and Q149. Residue numbering is based on SEQ ID NO: 36 (the soluble human TNFα sequence lacking the "S" cloning artefact).

The following additional A chain residues (also potentially forming part of a wider epitope) within a 5.0 Å proximity were identified: Q27, Q47, S81, Q88, Y119, R131 and S133. The following additional C chain residue (also potentially forming part of a wider epitope) within a 5.0 Å proximity was identified: P117. Again, residue numbering is based on SEQ ID NO: 36. These 4.0 and 5.0 Å residues are summarised in the table below, together with the residues on Fab 1974:

| TNF-A (4 Å) | TNF-C (4 Å) | Fab1974-L (4 Å) | Fab1974-H (4 Å) | TNF-A (5 Å) | TNF-C (5 Å) | Fab1974-L (5 Å) | Fab1974-H (5 Å) |
|---|---|---|---|---|---|---|---|
| T77 | L63 | N31 | T28 | Q27 | L63 | G30 | T28 |
| T79 | K65 | W32 | S30 | Q47 | K65 | N31 | S30 |
| I83 | Q67 | Y49 | A31 | T77 | Q67 | W32 | A31 |
| T89 | P113 | T52 | Y33 | T79 | P113 | Y49 | Y33 |
| K90 | Y115 | S53 | N52 | S81 | Y115 | T52 | N52 |
| V91 | D143 | R66 | Y53 | I83 | P117 | S53 | Y53 |
| N92 | A145 | G91 | F59 | Q88 | D143 | L54 | D54 |
| L93 | E146 | Q92 | Y101 | T89 | A145 | R66 | N57 |
| L94 | Q149 | S93 | G102 | K90 | E146 | G91 | F59 |
| S95 | | T94 | Y103 | V91 | Q149 | Q92 | E99 |
| A96 | | Y96 | N104 | N92 | | S93 | Y101 |
| I97 | | | N106 | L93 | | T94 | G102 |
| K98 | | | | L94 | | Y96 | Y103 |
| E135 | | | | S95 | | | N104 |
| I136 | | | | A96 | | | S105 |
| N137 | | | | I97 | | | N106 |
| R138 | | | | K98 | | | |
| | | | | Y119 | | | |
| | | | | R131 | | | |
| | | | | S133 | | | |
| | | | | E135 | | | |
| | | | | I136 | | | |
| | | | | N137 | | | |
| | | | | R138 | | | |

Example 12—Assessment of 1974 as a Target Occupancy Reagent

The ability of CA1974 to detect a range of different recombinant human TNFα concentrations pre-incubated with saturating levels of small molecule was tested. Pre-incubation of TNFα with excess compound was achieved by mixing 10 μs/ml TNFα with either 1% (v/v) DMSO or 10 μM compound (2) in 0.1% (w/v) BSA/PBS, resulting in an approximately 50-fold molar excess of small molecule inhibitor over TNFα.

Following overnight incubation the complex was diluted to a range of concentrations in human plasma that had been depleted of endogenous TNFα by immunoprecipitation using an in-house anti-TNFα monoclonal antibody. Small molecule-bound TNFα was measured using a sandwich ELISA. A 96 well ELISA plate (Nunc) was coated with 0.1 μg/ml CA1974 in PBS overnight at 4° C. After washing three times in wash buffer (0.05% (v/v) Tween-20/PBS) the plate was blocked in 2% (w/v) BSA/PBS for at least 1 h at RT. 100 μl of each sample was loaded to the blocked ELISA plate and incubated for 30 mins at RT with shaking at 200 rpm. The plate was washed 3 times in wash buffer before adding 100 μl per well of biotinylated anti-TNFα detection antibody (BAF210, R&D Systems), at a concentration of 0.1 μg/ml in 1% (w/v) BSA/wash buffer, for 1 h at RT with shaking at 200 rpm. Following 3 washes, 100 μl per well of 100 ng/ml Streptavidin-horse radish peroxidase (SA-HRP, Sigma) in 1% BSA/wash buffer was added and incubated for 45 mins at RT with shaking at 200 rpm. The plate was washed 3 times in wash buffer before including a biotin-tyramide (B-T) amplification step to provide additional amplification, using the ELAST system from Perkin Elmer. B-T solution was diluted 1 in 100 in ELAST buffer, 100 μl added per well and the plate incubated for exactly 15 mins at RT with shaking at 200 rpm before washing 4 times in wash buffer. An incubation with ELAST SA-HRP was performed, followed by 4 washes and the addition of 100 μl TMB (two component, KPL) per well. When appropriate colour change had been reached, the reaction was stopped by the addition of 100 μl per well of 2.5 M sulphuric acid.

Absorbance at 450 nm was measured using a Multiskan EX plate reader with Ascent Software version 2.6 (Thermo).

To determine the concentration at which TNFα+excess small molecule inhibitor could be detected above apo TNFα background, 3 standard deviations of the TNFα+DMSO OD results was added to the mean of these values. All TNFα+ small molecule spike results greater than this value were considered to be significantly different to apo TNFα, with a probability of at least 0.999.

Figure 14:
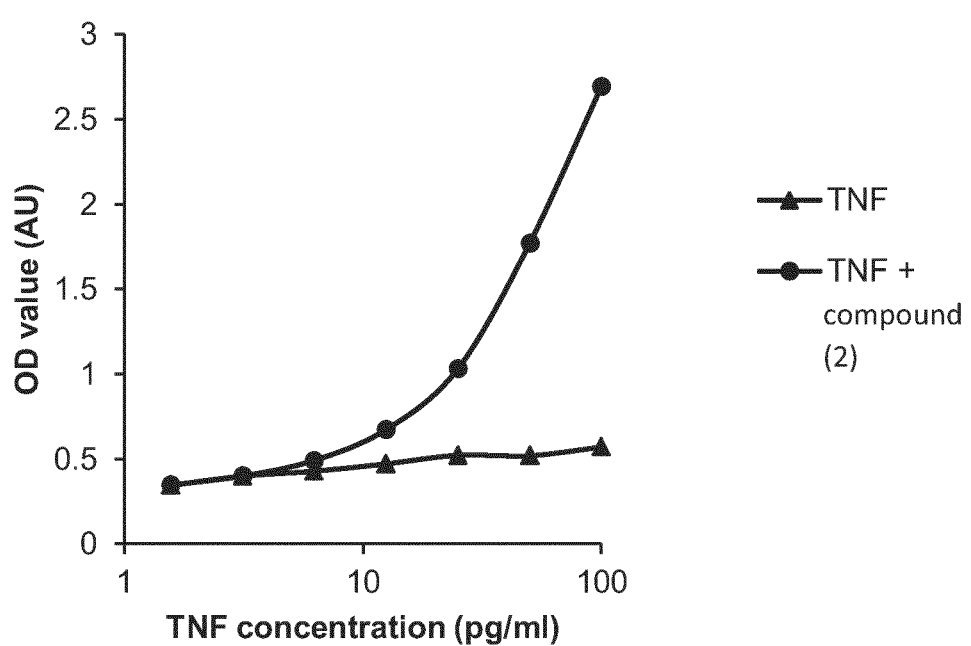

As can be seen FIG. 14, TNFα-small molecule complex could be detected at 25 pg/ml and above in neat plasma (with probability of at least 0.999) and there was no background cross-reactivity observed with apo TNFα. This demonstrates that CA1974 may be a useful reagent for the measurement of target occupancy in complex biological samples.

Example 13—Single Cycle Kinetics of Compound (1) Binding to Human TNFα Directly Immobilised or Via Capture with CA1974

For single cycle kinetics profiling of compound (1) to either directly immobilised TNFα or CA1974-captured TNFα surface plasmon resonance was performed at 25° C.

using a BIAcore T200 (GE Healthcare). Human TNFα was tethered onto flow-channel (Fc)2 (2000 RU). CA1974 IgG (>10,000 response units) was tethered onto Fc3,4 and Fc1 blank immobilisation on a CMS Sensor Chip (GE Healthcare) via amine coupling chemistry. The surface was allowed to stabilise in HBS-P buffer (10 mM HEPES, pH 7.4, 0.15 M NaCl, 0.0005% (v/v) surfactant P20-GE Healthcare)+5% DMSO was used as the running buffer. Human TNFα was flowed over Fc4 to a capture level of ~2,000 RU. Compound (1) was flowed over all four flow cells in series (1.875 μM, 3.75 μM, 7.5 μM and 30 μM) at 100 μl/min. Double referenced background-subtracted binding curves were produced using the T200 Evaluation software (version 1.0) following standard procedures. Results are presented in FIG. 15.

As indicated, kinetics change from "slow on-slow off" with directly immobilised apo-TNF to "fast on-fast off" when captured via the conformation-selective antibody CA1974. This indicates that the antibody is able to stabilise an alternative, presumably open conformation which might facilitate the identification of new chemical matter which, under normal circumstances, is entropically disadvantaged.

Interestingly, despite structural models revealing major side chain clashes with the symmetric form of apo TNFα (FIG. 12), both Biacore and SE-HPLC experiments suggested that CA1974 is able to interact with apo TNFα. The affinity of the interaction was typically >100-fold lower than that observed with the TNFα-small molecule complex. SE-HPLC suggested that CA1974 interacts with a small fraction (21%) of apo TNFα and produces a complex that has elution characteristics consistent with a 1:1 (Fab: apo TNFα trimer) complex. Taken together, these observations support the hypothesis that apo TNFα naturally adopts an "open" conformation that allows antibody recognition rather than the antibody binding to a partial epitope on the symmetric molecule. The lower amount of complex that is present in the SE-HPLC experiment compared to the Fab-TNFα-small molecule complex and the lower observed affinity for apo TNFα could imply that this "open" conformation is sampled naturally but exists only transiently and that this form of the apo TNFα is much less energetically stable than the small molecule-stabilised form and hence the antibody interaction is compromised. These findings support the conclusions made in previous molecular dynamic simulation studies and DEER experiments with spin-labelled TNFα which predicts 6% of trimers at any one time adopt a naturally-sampled asymmetric open state. The presence of CA1974 in the SEC HPLC experiment likely draws the equilibrium of conformational sampling towards the open state, increasing the percentage of asymmetric trimer.

This highlights how antibodies, which define rarely sampled conformations of target proteins, may facilitate small molecule fragment screening by enabling the binding of otherwise entropically disadvantaged compounds (FIG. 15) or act as a 'sensor' to detect new chemical matter that is able to stabilise predefined inactive conformations. Conversely, small molecules which stabilise rarely sampled conformations of target proteins, may augment the generation of antibodies recognising induced neo-epitopes.

```
Sequence listing
(LCDR1 of 1974)
                                                          SEQ ID NO: 1
QASQDIGN (LCDR2 of 1974)
                                                          SEQ ID NO: 2
GATSLAD (LCDR3 of 1974)
                                                          SEQ ID NO: 3
LQGQSTPYT (HCDR1 of 1974)
                                                          SEQ ID NO: 4
AYYMA (HCDR2 of 1974)
                                                          SEQ ID NO: 5
ASINYDGANTFYRDSVKG (HCDR3 of 1974)
                                                          SEQ ID NO: 6
EAYGYNSNWFGY (LCVR of 1974)
                                                          SEQ ID NO: 7
DIQMTQSPASLPASPEEIVTITCQASQDIGNWLSWYQQKPGKSPQLLIYGATSLADGVPSRFSASRSGT

QYSLKISRLQVEDFGIFYCLQGQSTPYTFGAGTKLELK (HCVR of 1974)
                                                          SEQ ID NO: 8
DVQLVESGGGLVQPGRSLKLSCAASGFTFSAYYMAWVRQAPTKGLEWVASINYDGANTFYRDSVKGRFT

VSRDNARSSLYLQMDSLRSEDTATYYCTTEAYGYNSNWFGYWGQGTLVTVSS (LCVR DNA of 1974)
                                                          SEQ ID NO: 9
GACATCCAGATGACCCAGTCTCCTGCCTCCCTGCCTGCATCCCCGGAAGAAATTGTCACCATCACATGC

CAGGCAAGCCAGGACATTGGTAATTGGTTATCATGGTATCAGGAGAAACCAGGGAAATCGCCTCAGCTC
```

-continued

CTGATCTATGGTGCAACCAGCTTGGCAGATGGGGTCCCATCAAGGTTCAGCGCCAGTAGATCTGGCACA

CAGTACTCTCTTAAGATCAGGAGACTGCAGGTTGAAGATTTTGGAATCTTTTACTGTCTACAGGGTCAA

AGTACTCCGTACACGTTTGGAGCTGGGACCAAGCTGGAACTGAAA (HCVR DNA of 1974)
SEQ ID NO: 10

GACGTGCAGCTGGTGGAATCTGGAGGAGGCTTAGTGCAGCCTGGAAGGTCCCTGAAACTCTCCTGTGCA

GCCTCAGGATTCACTTTCAGTGCCTATTACATGGCCTGGGTCCGCCAGGCTCCAACGAAGGGTCTGGAG

TGGGTCGCATCCATTAATTATGATGGTGCTAACACTTTCTATCGCGACTCCGTGAAGGGCCGATTCACT

GTCTCCAGAGATAATGCAAGAAGGAGCCTATACCTACAAATGGACAGTCTGAGGTCTGAGGACACGGCC

ACTTATTACTGTACAACAGAGGCTTACGGATATAACTCAAATTGGTTTGGTTACTGGGGCCAAGGCACT

CTGGTCACTGTCTCGAGC (1974 LC kappa full)
SEQ ID NO: 11

DIQMTQSPASLPASPEEIVTITCQASQDIGNWLSWYQQKPGKSPQLLIYGATSLADGVPSRFSASRSGT

QYSLKISRLQVEDFGIFYCLQGQSTPYTFGAGTKLELKRTDAAPTVSIFPPSSEQLTSGGASVVCFLNN

FYPKDINVKWKIDGSERQNGVLNSWTDQDSKDSTYSMSSTLTLTKDEYERHNSYTCEATHKTSTSPIVK

SFNRNEC (1974 HC mIgG1 full)
SEQ ID NO: 12

DVQLVESGGGLVQPGRSLKLSCAASGFTFSAYYMAWVRQAPTKGLEWVASINYDGANTFYRDSVKGRFT

VSRDNARSSLYLQMDSLRSEDTATYYCTTEAYGYNSNWFGYWGQGTLVTVSSAKTTPPSVYPLAPGSAA

QTNSMVTLGCLVKGYFPEPVTVTWNSGSLSSGVHTFPAVLQSDLYTLSSSVTVPSSTWPSETVTCNVAH

PASSTKVDKKIVPRDCGCKPCICTVPEVSSVFIFPPKPKDVLTITLTPKVTCVVVDISKDDPEVQFSWF

VDDVEVHTAQTQPREEQFNSTFRSVSELPIMHQDWLNGKEFKCRVNSAAFPAPIEKTISKTKGRPKAPQ

VYTIPPPKEQMAKDKVSLTCMITDFFPEDITVEWQWNGQPAENYKNTQPIMDTDGSYFVYSKLNVQKSN

WEAGNTFTCSVLHEGLHNHHTEKSLSHSPGK (1974 HC mFabno hinge full)
SEQ ID NO: 13

DVQLVESGGGLVQPGRSLKLSCAASGFTFSAYYMAWVRQAPTKGLEWVASINYDGANTFYRDSVKGRFT

VSRDNARSSLYLQMDSLRSEDTATYYCTTEAYGYNSNWFGYWGQGTLVTVSSAKTTPPSVYPLAPGSAA

QTNSMVTLGCLVKGYFPEPVTVTWNSGSLSSGVHTFPAVLQSDLYTLSSSVTVPSSTWPSETVTCNVAH

PASSTKVDKKIVPRDC (1974 LC DNA kappa full)
SEQ ID NO: 14

GACATCCAGATGACCCAGTCTCCTGCCTCCCTGCCTGCATCCCCGGAAGAAATTGTCACCATCACATGC

CAGGCAAGCCAGGACATTGGTAATTGGTTATCATGGTATCAGCAGAAACCAGGGAAATCGCCTCAGCTC

CTGATCTATGGTGCAACCAGCTTGGCAGATGGGGTCCCATCAAGGTTCAGCGCCAGTAGATCTGGCACA

CAGTACTCTCTTAAGATCAGCAGACTGCAGGTTGAAGATTTTGGAATCTTTTACTGTCTACAGGGTCAA

AGTACTCCGTACACGTTTGGAGCTGGGACCAAGCTGGAACTGAAACGTACGGATGCTGCACCAACTGTA

TCCATCTTCCCACCATCCAGTGAGCAGTTAACATCTGGAGGTGCCTCAGTCGTGTGCTTCTTGAACAAC

TTCTACCCCAAAGACATCAATGTCAAGTGGAAGATTGATGGCAGTGAACGACAAAATGGCGTCCTGAAC

AGTTGGACTGATCAGGACAGCAAAGACAGCACCTACAGCATGAGCAGCACCCTCACGTTGACCAAGGAC

GAGTATGAACGACATAACAGCTATACCTGTGAGGCCACTCACAAGACATCAACTTCACCCATTGTCAAG

AGCTTCAACAGGAATGAGTGT (1974 HC DNA mIgG1 full)

SEQ ID NO: 15

```
GACGTGCAGCTGGTGGAATCTGGAGGAGGCTTAGTGCAGCCTGGAAGGTCCCTGAAACTCTCCTGTGCA
GCCTCAGGATTCACTTTCAGTGCCTATTACATGGCCTGGGTCCGCCAGGCTCCAACGAAGGGTCTGGAG
TGGGTCGCATCCATTAATTATGATGGTGCTAACACTTTCTATCGCGACTCCGTGAAGGGCCGATTCACT
GTCTCCAGAGATAATGCAAGAAGCAGCCTATACCTACAAATGGACAGTCTGAGGTCTGAGGACACGGCC
ACTTATTACTGTACAACAGAGGCTTACGGATATAACTCAAATTGGTTTGGTTACTGGGGCCAAGGCACT
CTGGTCACTGTCTCGAGTGCCAAAACGACACCCCCATCTGTCTATCCACTGGCCCCTGGATCTGCTGCC
CAAACTAACTCCATGGTGACCCTGGGATGCCTGGTCAAGGGCTATTTCCCTGAGCCAGTGACAGTGACC
TGGAACTCTGGATCCCTGTCCAGCGGTGTGCACACCTTCCCAGCTGTCCTGCAGTCTGACCTCTACACT
CTGAGCAGCTCAGTGACTGTCCCCTCCAGCACCTGGCCCAGCGAGACCGTCACCTGCAACGTTGCCCAC
CCGGCCAGCAGCACCAAGGTGGACAAGAAAATTGTGCCCAGGGATTGTGGTTGTAAGCCTTGCATATGT
ACAGTCCCAGAAGTATCATCTGTCTTCATCTTCCCCCCAAAGCCCAAGGATGTGCTCACCATTACTCTG
ACTCCTAAGGTCACGTGTGTTGTGGTAGACATCAGCAAGGATGATCCCGAGGTCCAGTTCAGCTGGTTT
GTAGATGATGTGGAGGTGCACACAGCTCAGACGCAACCCCGGGAGGAGCAGTTCAACAGCACTTTCCGC
TCAGTCAGTGAACTTCCCATCATGCACCAGGACTGGCTCAATGGCAAGGAGTTCAAATGCAGGGTCAAC
AGTGCAGCTTTCCCTGCCCCCATCGAGAAAACCATCTCCAAAACCAAAGGCAGACCGAAGGCTCCACAG
GTGTACACCATTCCACCTCCCAAGGAGCAGATGGCCAAGGATAAAGTCAGTCTGACCTGCATGATAACA
GACTTCTTCCCTGAAGACATTACTGTGGAGTGGCAGTGGAATGGGCAGCCAGCGGAGAACTACAAGAAC
ACTCAGCCCATCATGGACACAGATGGCTCTTACTTCGTCTACAGCAAGCTCAATGTGCAGAAGAGCAAC
TGGGAGGCAGGAAATACTTTCACCTGCTCTGTGTTACATGAGGGCCTGCACAACCACCATACTGAGAAG
AGCCTCTCCCACTCTCCTGGTAAA
```

(1974 HC DNA mFabno hinge full)

SEQ ID NO: 16

```
GACGTGCAGCTGGTGGAATCTGGAGGAGGCTTAGTGCAGCCTGGAAGGTCCCTGAAACTCTCCTGTGCA
GCCTCAGGATTCACTTTCAGTGCCTATTACATGGCCTGGGTCCGCCAGGCTCCAACGAAGGGTCTGGAG
TGGGTCGCATCCATTAATTATGATGGTGCTAACACTTTCTATCGCGACTCCGTGAAGGGCCGATTCACT
GTCTCCAGAGATAATGCAAGAAGCAGCCTATACCTACAAATGGACAGTCTGAGGTCTGAGGACACGGCC
ACTTATTACTGTACAACAGAGGCTTACGGATATAACTCAAATTGGTTTGGTTACTGGGGCCAAGGCACT
CTGGTCACTGTCTCGAGTGCCAAAACGACACCCCCATCTGTCTATCCACTGGCCCCTGGATCTGCTGCC
CAAACTAACTCCATGGTGACCCTGGGATGCCTGGTCAAGGGCTATTTCCCTGAGCCAGTGACAGTGACC
TGGAACTCTGGATCCCTGTCCAGCGGTGTGCACACCTTCCCGGCTGTCCTGCAATCTGACCTCTACACT
CTGAGCAGCTCAGTGACTGTCCCCTCCAGCACCTGGCCCAGCGAGACCGTCACCTGCAACGTTGCCCAC
CCGGCCAGCAGCACCAAGGTGGACAAGAAAATTGTGCCCAGGGATTGT
```

(LCDR2 of 1979)

SEQ ID NO: 17

GTTSLAD (LCDR3 of 1979)

SEQ ID NO: 18

LQAYSTPFTF (HCDR1 of 1979)

SEQ ID NO: 19

NSYWD (HCDR2 of 1979)

SEQ ID NO: 20

YINYSGSTGYNPSLKS (HCDR3 of 1979)
SEQ ID NO: 21
GTYGYNAYHFDY (LCVR of 1979)
SEQ ID NO: 22
DIQMTQSPASLSASLEEIVTITCQASQDIGNWLSWYQQKPGKSPHLLIYGTTSLADGVPSRFSGSRSGT
QYSLKISGLQVADIGIYVCLQAYSTPFTFGSGTKLEIK (HCVR of 1979)
SEQ ID NO: 23
EVHLVESGPGLVKPSQSLSLTCSVTGYSITNSYWDWIRKFPGNKMEWMGYINYSGSTGYNPSLKSRISI
SRDTSNNQFFLQLNSITTEDTATYYCARGTYGYNAYHFDYWGRGVMVTVSS (LCVR DNA of 1979)
SEQ ID NO: 24
GACATCCAAATGACACAGTCTCCTGCCTCCCTGTCTGCATCTCTGGAAGAAATTGTCACCATTACATGC
CAGGCAAGCCAGGACATTGGTAATTGGTTATCATGGTATCAGCAGAAACCAGGGAAATCTCCTCACCTC
CTGATCTATGGTACCACCAGCTTGGCAGATGGGGTCCCATCAAGGTTCAGCGGCAGTAGATCTGGTACA
CAGTATTCTCTTAAGATCAGCGGACTACAGGTTGCAGATATTGGAATCTATGTCTGTCTACAGGCTTAT
AGTACTCCATTCACGTTCGGCTCAGGGACAAAGCTGGAAATAAAA (HCVR DNA of 1979)
SEQ ID NO: 25
GAGGTGCACCTGGTGGAGTCTGGACCTGGCCTTGTGAAACCCTCACAGTCACTCTCCCTCACCTGTTCT
GTCACTGGTTACTCCATCACTAATAGTTACTGGGACTGGATCCGGAAGTTCCCAGGAAATAAAATGGAG
TGGATGGGATACATAAACTACAGTGGTAGCACTGGCTACAACCCATCTCTCAAAAGTCGAATCTCCATT
AGTAGAGACACATCGAACAATCAGTTCTTCCTGCAGCTGAACTCTATAACTACTGAGGACACAGCCACA
TATTACTGTGCACGAGGGACCTATGGGTATAACGCCTACCACTTTGATTACTGGGGCCGAGGAGTCATG
GTCACAGTCTCGAGC (1979 LC Kappa full)
SEQ ID NO: 26
DIQMTQSPASLSASLEEIVTITCQASQDIGNWLSWYQQKPGKSPHLLIYGTTSLADGVPSRFSGSRSGT
QYSLKISGLQVADIGIYVCLQAYSTPFTFGSGTKLEIKRTDAAPTVSIFPPSSEQLTSGGASVVCFLNN
FYPKDINVKWKIDGSERQNGVLNSWTDQDSKDSTYSMSSTLTLTKDEYERHNSYTCEATHKTSTSPIVK
SFNRNEC (1979 HC mIgG1 full)
SEQ ID NO: 27
EVHLVESGPGLVKPSQSLSLTCSVTGYSITNSYWDWIRKFPGNKMEWMGYINYSGSTGYNPSLKSRISI
SRDTSNNQFFLQLNSITTEDTATYYCARGTYGYNAYHFDYWGRGVMVTVSSAKTTPPSVYPLAPGSAAQ
TNSMVTLGCLVKGYFPEPVTVTWNSGSLSSGVHTFPAVLQSDLYTLSSSVTVPSSTWPSETVTCNVAHP
ASSTKVDKKIVPRDCGCKPCICTVPEVSSVFIFPPKPKDVLTITLTPKVTCVVVDISKDDPEVQFSWFV
DDVEVHTAQTQPREEQFNSTFRSVSELPIMHQDWLNGKEFKCRVNSAAFPAPIEKTISKTKGRPKAPQV
YTIPPPKEQMAKDKVSLTCMITDFFPEDITVEWQWNGQPAENYKNTQPIMDTDGSYFVYSKLNVQKSNW
EAGNTFTCSVLHEGLHNHHTEKSLSHSPGK (1979 HC mFabno hinge full)
SEQ ID NO: 28
EVHLVESGPGLVKPSQSLSLTCSVTGYSITNSYWDWIRKFPGNKMEWMGYINYSGSTGYNPSLKSRISI
SRDTSNNQFFLQLNSITTEDTATYYCARGTYGYNAYHFDYWGRGVMVTVSSAKTTPPSVYPLAPGSAAQ
TNSMVTLGCLVKGYFPEPVTVTWNSGSLSSGVHTFPAVLQSDLYTLSSSVTVPSSTWPSETVTCNVAHP
ASSTKVDKKIVPRDC -continued (1979 LC DNA Kappa full)
SEQ ID NO: 29
GACATCCAAATGACACAGTCTCCTGCCTCCCTGTCTGCATCTCTGGAAGAAATTGTCACCATTACATGC

CAGGCAAGCCAGGACATTGGTAATTGGTTATCATGGTATCAGCAGAAACCAGGGAAATCTCCTCACCTC

CTGATCTATGGTACCACCAGCTTGGCAGATGGGGTCCCATCAAGGTTCAGCGGCAGTAGATCTGGTACA

CAGTATTCTCTTAAGATCAGCGGACTACAGGTTGCAGATATTGGAATCTATGTCTGTCTACAGGCTTAT

AGTACTCCATTCACGTTCGGCTCAGGGACAAAGCTGGAAATAAAACGTACGGATGCTGCACCAACTGTA

TCCATCTTCCCACCATCCAGTGAGCAGTTAACATCTGGAGGTGCCTCAGTCGTGTGCTTCTTGAACAAC

TTCTACCCCAAAGACATCAATGTCAAGTGGAAGATTGATGGCAGTGAACGACAAAATGGCGTCCTGAAC

AGTTGGACTGATCAGGACAGCAAAGACAGCACCTACAGCATGAGCAGCACCCTCACGTTGACCAAGGAC

GAGTATGAACGACATAACAGCTATACCTGTGAGGCCACTCACAAGACATCAACTTCACCCATTGTCAAG

AGCTTCAACAGGAATGAGTGT (1979 HC DNA mIgG1 full)
SEQ ID NO: 30
GAGGTGCACCTGGTGGAGTCTGGACCTGGCCTTGTGAAACCCTCACAGTCACTCTCCCTCACCTGTTCT

GTCACTGGTTACTCCATCACTAATAGTTACTGGGACTGGATCCGGAAGTTCCCAGGAAATAAAATGGAG

TGGATGGGATACATAAACTACAGTGGTAGCACTGGCTACAACCCATCTCTCAAAAGTCGAATCTCCATT

AGTAGAGACACATCGAACAATCAGTTCTTCCTGCAGCTGAACTCTATAACTACTGAGGACACAGCCACA

TATTACTGTGCACGAGGGACCTATGGGTATAACGCCTACCACTTTGATTACTGGGGCCGAGGAGTCATG

GTCACAGTCTCGAGTGCCAAAACGACACCCCCATCTGTCTATCCACTGGCCCCTGGATCTGCTGCCCAA

ACTAACTCCATGGTGACCCTGGGATGCCTGGTCAAGGGCTATTTCCCTGAGCCAGTGACAGTGACCTGG

AACTCTGGATCCCTGTCCAGCGGTGTGCACACCTTCCCAGCTGTCCTGCAGTCTGACCTCTACACTCTG

AGCAGCTCAGTGACTGTCCCCTCCAGCACCTGGCCCAGCGAGACCGTCACCTGCAACGTTGCCCACCCG

GCCAGCAGCACCAAGGTGGACAAGAAAATTGTGCCCAGGGATTGTGGTTGTAAGCCTTGCATATGTACA

GTCCCAGAAGTATCATCTGTCTTCATCTTCCCCCCAAAGCCCAAGGATGTGCTCACCATTACTCTGACT

CCTAAGGTCACGTGTGTTGTGGTAGACATCAGCAAGGATGATCCCGAGGTCCAGTTCAGCTGGTTTGTA

GATGATGTGGAGGTGCACACAGCTCAGACGCAACCCCGGGAGGAGCAGTTCAACAGCACTTTCCGCTCA

GTCAGTGAACTTCCCATCATGCACCAGGACTGGCTCAATGGCAAGGAGTTCAAATGCAGGGTCAACAGT

GCAGCTTTCCCTGCCCCCATCGAGAAAACCATCTCCAAAACCAAAGGCAGACCGAAGGCTCCACAGGTG

TACACCATTCCACCTCCCAAGGAGCAGATGGCCAAGGATAAAGTCAGTCTGACCTGCATGATAACAGAC

TTCTTCCCTGAAGACATTACTGTGGAGTGGCAGTGGAATGGGCAGCCAGCGGAGAACTACAAGAACACT

CAGCCCATCATGGACACAGATGGCTCTTACTTCGTCTACAGCAAGCTCAATGTGCAGAAGAGCAACTGG

GAGGCAGGAAATACTTTCACCTGCTCTGTGTTACATGAGGGCCTGCACAACCACCATACTGAGAAGAGC

CTCTCCCACTCTCCTGGTAAA (1979 HC DNA mFabno hinge full)
SEQ ID NO: 31
GAGGTGCACCTGGTGGAGTCTGGACCTGGCCTTGTGAAACCCTCACAGTCACTCTCCCTCACCTGTTCT

GTCACTGGTTACTCCATCACTAATAGTTACTGGGACTGGATCCGGAAGTTCCCAGGAAATAAAATGGAG

TGGATGGGATACATAAACTACAGTGGTAGCACTGGCTACAACCCATCTCTCAAAAGTCGAATCTCCATT

AGTAGAGACACATCGAACAATCAGTTCTTCCTGCAGCTGAACTCTATAACTACTGAGGACACAGCCACA

TATTACTGTGCACGAGGGACCTATGGGTATAACGCCTACCACTTTGATTACTGGGGCCGAGGAGTCATG

GTCACAGTCTCGAGTGCCAAAACGACACCCCCATCTGTCTATCCACTGGCCCCTGGATCTGCTGCCCAA

ACTAACTCCATGGTGACCCTGGGATGCCTGGTCAAGGGCTATTTCCCTGAGCCAGTGACAGTGACCTGG

AACTCTGGATCCCTGTCCAGCGGTGTGCACACCTTCCCGGCTGTCCTGCAATCTGACCTCTACACTCTG

-continued

```
AGCAGCTCAGTGACTGTCCCCTCCAGCACCTGGCCCAGCGAGACCGTCACCTGCAACGTTGCCCACCCG

GCCAGCAGCACCAAGGTGGACAAGAAAATTGTGCCCAGGGATTGT
```

Rat TNFα

SEQ ID NO: 32

```
MSTESMIRDVELAEEALPKKMGGLQNSRRCLCLSLFSFLLVAGATTLFCLLNFGVIGPNKEEKFPNGLP

LISSMAQTLTLRSSSQNSSDKPVAHVVANHQAEEQLEWLSQRANALLANGMDLKDNQLVVPADGLYLIY

SQVLFKGQGCPDYVLLTHTVSRFAISYQEKVSLLSAIKSPCPKDTPEGAELKPWYEPMYLGGVFQLEKG

DLLSAEVNLPKYLDITESGQVYFGVIAL
```

Mouse TNFα

SEQ ID NO: 33

```
MSTESMIRDVELAEEALPQKMGGFQNSRRCLCLSLFSFLLVAGATTLFCLLNFGVIGPQRDEKFPNGLP

LISSMAQTLTLRSSSQNSSDKPVAHVVANHQVEEQLEWLSQRANALLANGMDLKDNQLVVPADGLYLVY

SQVLFKGQGCPDYVLLTHTVSRFAISYQEKVNLLSAVKSPCPKDTPEGAELKPWYEPIYLGGVFQLEKG

DQLSAEVNLPKYLDFAESGQVYFGVIAL
```

Human TNFα

SEQ ID NO: 34

```
MSTESMIRDVELAEEALPKKTGGPQGSRRCLFLSLFSFLIVAGATTLFCLLHFGVIGPQREEFPRDLSL

ISPLAQAVRSSSRTPSDKPVAHVVANPQAEGQLQWLNRRANALLANGVELRDNQLVVPSEGLYLIYSQV

LFKGQGCPSTHVLLTHTISRIAVSYQTKVNLLSAIKSPCQRETPEGAEAKPWYEPIYLGGVFQLEKGDR

LSAEINRPDYLDFAESGQVYFGIIAL
```

Soluble form of human TNFα

SEQ ID NO: 35

```
SVRSSSRTPSDKPVAHVVANPQAEGQLQWLNRRANALLANGVELRDNQLVVPSEGLYLIYSQVLFKGQG

CPSTHVLLTHTISRIAVSYQTKVNLLSAIKSPCQRETPEGAEAKPWYEPIYLGGVFQLEKGDRLSAEIN

RPDYLDFAESGQVYFGIIAL
```

Soluble form of human TNFα but excluding the initial
"S" of SEQ ID NO: 35, which is a cloning artefact

SEQ ID NO: 36

```
VRSSSRTPSDKPVAHVVANPQAEGQLQWLNRRANALLANGVELRDNQLVVPSEGLYLIYSQVLFKGQGC

PSTHVLLTHTISRIAVSYQTKVNLLSAIKSPCQRETPEGAEAKPWYEPIYLGGVFQLEKGDRLSAEINR

PDYLDFAESGQVYFGIIAL
```

Extracellular domain of human TNFR1 with N54D and
C182S mutations (including initial "G", which is a cloning artefact)

SEQ ID NO: 37

```
GSVCPQGKYIHPQDNSICCTKCHKGTYLYNDCPGPGQDTDCRECESGSFTASENHLRHCLSCSKCRKEM

GQVEISSCTVDRDTVCGCRKNQYRHYWSENLFQCFNCSLCLNGTVHLSCQEKQNTVCTCHAGFFLRENE

CVSSSN
```

Extracellular domain of human TNFR1 with N54D and
C182S mutations (excluding initial "G", which is a cloning artefact)

SEQ ID NO: 38

```
SVCPQGKYIHPQDNSICCTKCHKGTYLYNDCPGPGQDTDCRECESGSFTASENHLRHCLSCSKCRKEMG

QVEISSCTVDRDTVCGCRKNQYRHYWSENLFQCFNCSLCLNGTVHLSCQEKQNTVCTCHAGFFLRENEC

VSSSN
```

---

The invention claimed is:

1. An antibody comprising:
   a HCDR1 selected from SEQ ID NOs: 4 and 19;
   a HCDR2 selected from SEQ ID NOs: 5 and 20; and
   a HCDR3 selected from SEQ ID NOs: 6 and 21; and
   a LCDR1 of SEQ ID NO: 1;
   a LCDR2 selected from SEQ ID NOs: 2 and 17; and
   a LCDR3 selected from SEQ ID NOs: 3 and 18.

2. An antibody according to claim 1, which
   (a) is a humanised antibody; or
   (b) is a Fab, modified Fab, Fab', modified Fab', F(ab')₂, Fv, single domain antibody or an scFv.

3. An antibody according to claim 1, which binds a complex of trimeric TNFα and any one of compounds (1)-(7):

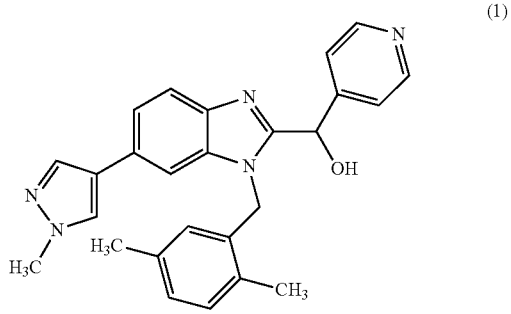

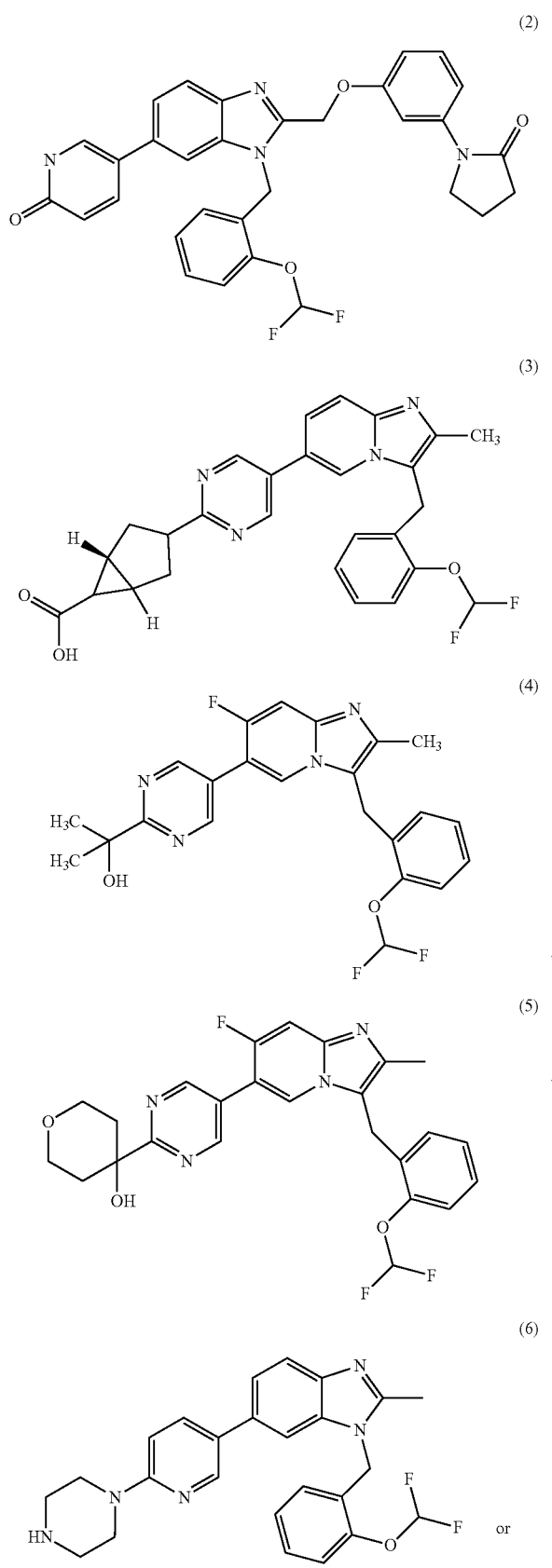

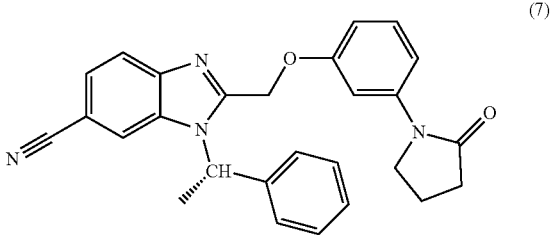

and which optionally has an affinity ($K_{D\text{-}ab}$) of 1 nM or less for the trimer-compound complex; or an affinity of 200 pM or less.

4. The antibody of claim 1, wherein the antibody comprises at least one HCDR selected from SEQ ID NOS:4-6 and at least one LCDR selected from SEQ ID NOS: 1-3.

5. The antibody of claim 1, wherein the antibody comprises at least one HCDR selected from SEQ ID NOS:19-21 and at least one LCDR selected from SEQ ID NOS: 1, 17 and 18.

6. The antibody of claim 1, wherein the antibody comprises at least two HCDRs selected from SEQ ID NOS:4-6 and at least two LCDRs selected from SEQ ID NOS: 1-3.

7. The antibody of claim 1, wherein the antibody comprises at least two HCDRs selected from SEQ ID NOS:19-21 and at least two LCDRs selected from SEQ ID NOS: 1, 17 and 18.

8. The antibody of claim 1, wherein the antibody comprises SEQ ID NO:4 for HCDR1, SEQ ID NO:5 for HCDR2 and SEQ ID NO:6 for HCDR3 and SEQ ID NO:1 for LCDR1, SEQ ID NO:2 for LCDR2 and SEQ ID NO:3 for LCDR3.

9. The antibody of claim 1, wherein the antibody comprises SEQ ID NO:19 for HCDR1, SEQ ID NO:20 for HCDR2 and SEQ ID NO:21 for HCDR3, and SEQ ID NO:1 for LCDR1, SEQ ID NO:17 for LCDR2 and SEQ ID NO:18 for LCDR3.

10. An antibody comprising (a) a heavy chain variable region (HCVR) comprising SEQ ID NO:8 or 23, or (b) HCDR regions of SEQ ID NO:8 or 23 and remainder of the heavy chain variable region comprises more than 90% identity to SEQ ID NO:8 or 23; and (c) a light chain variable region (LCVR) comprising SEQ ID NO:7 or 22, or (d) LCDR regions of SEQ ID NO:7 or 22 and remainder of the light chain variable region comprises more than 90% identity to SEQ ID NO:7 or 22.

11. The antibody of claim 10, wherein the antibody comprises an HCVR comprising SEQ ID NO:8 or HCDR regions of SEQ ID NO:8 and remainder of the heavy chain variable region comprises more than 90% identity to SEQ ID NO:8, and an LCVR comprising SEQ ID NO:7 or LCDR regions of SEQ ID NO:7 and remainder of the light chain variable region comprises more than 90% identity to SEQ ID NO:7.

12. The antibody of claim 10, wherein the antibody comprises an HCVR comprising SEQ ID NO:23 or HCDR regions of SEQ ID NO:23 and remainder of the heavy chain variable region comprises more than 90% identity to SEQ ID NO:23, and an LCVR comprising SEQ ID NO:22 or LCDR regions of SEQ ID NO:22 and remainder of the light chain variable region comprises more than 90% identity to SEQ ID NO:22.

13. An antibody comprising (a) a heavy chain comprising SEQ ID NO:12 or 13, or (b) HCDR regions of SEQ ID NO:12 or 13 and remainder of the heavy chain comprises more than 90% identity to SEQ ID NO:12 or 13; and
  (c) a light chain comprising SEQ ID NO:11, or (d) LCDR regions of SEQ ID NO:11 and remainder of the light chain variable region comprises more than 90% identity to SEQ ID NO:11.

14. An antibody comprising (a) a heavy chain comprising SEQ ID NO:27 or 28, or (b) HCDR regions of SEQ ID NO:27 or 28 and remainder of the heavy chain comprises more than 90% identity to SEQ ID NO:27 or 28; and
  (c) a light chain comprising SEQ ID NO:26, or (d) LCDR regions of SEQ ID NO:26 and remainder of the light chain variable region comprises more than 90% identity to SEQ ID NO:26.

* * * * *